(12) United States Patent
Brekke et al.

(10) Patent No.: US 10,478,689 B2
(45) Date of Patent: Nov. 19, 2019

(54) METHOD, SYSTEM, AND APPARATUS FOR ANALYZING A SPORTING APPARATUS

(71) Applicant: Sumitomo Rubber Industries, Ltd., Kobe (JP)

(72) Inventors: Dustin J. Brekke, Fountain Valley, CA (US); Jay Vogler, Huntington Beach, CA (US); Patrick Ripp, Seal Beach, CA (US); Mitchell Samson, Newport Beach, CA (US); Jeff D. Brunski, Los Angeles, CA (US); Brian D. Schielke, Los Angeles, CA (US); Scott A. Carlyle, Costa Mesa, CA (US); Phillip C. Seagram, Long Beach, CA (US); Christopher J. Beck, Costa Mesa, CA (US); Eli Miller, Costa Mesa, CA (US); Kirk D. Bacon, Long Beach, CA (US); Jacob N. Lambeth, Irvine, CA (US)

(73) Assignee: Sumitomo Rubber Industries, Ltd., Hyogo (JP)

( * ) Notice: Subject to any disclaimer, the term of this patent is extended or adjusted under 35 U.S.C. 154(b) by 212 days.

(21) Appl. No.: 15/477,790

(22) Filed: Apr. 3, 2017

(65) Prior Publication Data
US 2017/0274256 A1   Sep. 28, 2017

Related U.S. Application Data

(63) Continuation-in-part of application No. 14/848,083, filed on Sep. 8, 2015, now Pat. No. 10,080,941.
(Continued)

(51) Int. Cl.
*A63B 69/00* (2006.01)
*A63B 60/42* (2015.01)
(Continued)

(52) U.S. Cl.
CPC .......... *A63B 60/42* (2015.10); *A63B 24/0006* (2013.01); *A63B 60/46* (2015.10);
(Continued)

(58) Field of Classification Search
USPC ....... 473/131, 219, 221–224, 233, 234, 289, 473/407, 409
See application file for complete search history.

(56) References Cited

U.S. PATENT DOCUMENTS

| 7,021,140 B2 | 4/2006 | Perkins |
| 7,024,351 B2 | 4/2006 | Wang |
(Continued)

OTHER PUBLICATIONS http://www.zepp.com/golf/club-sensor-setup/Zepp Golf Swing Analysis and Trainer System. Zepp USA, Inc. 2015.

*Primary Examiner* — Nini F Legesse
(74) *Attorney, Agent, or Firm* — Stetina Brunda Garred & Brucker

(57) ABSTRACT

A method for use in a system implementing a reference golf club, one or more sensors associated with the reference golf club, and a computing device. Using the computing device, the method comprises receiving from the one or more sensors swing data relating to a swing of the reference golf club, analyzing the swing data to determine recommended shaft parameter values for each of a plurality of shaft parameters using an algorithm, accessing a shaft database comprising actual shaft parameter values for each of the plurality of shaft parameters for each of a plurality of shafts, determining at least one shaft from the plurality of shafts based, at least in part, on a comparison between the recommended shaft parameter values and the actual shaft parameter values, transmitting information relating to the at least one shaft; and displaying the information on a display of the computing device.

20 Claims, 19 Drawing Sheets

Related U.S. Application Data

(60) Provisional application No. 62/188,393, filed on Jul. 2, 2015.

(51) Int. Cl.
*A63B 24/00* (2006.01)
*A63B 60/46* (2015.01)
*A63B 71/06* (2006.01)
*G01S 19/19* (2010.01)
*G06F 19/00* (2018.01)
*G06K 9/00* (2006.01)

(52) U.S. Cl.
CPC .......... *A63B 71/0622* (2013.01); *G01S 19/19* (2013.01); *G06F 19/3481* (2013.01); *G06K 9/00342* (2013.01); *G06K 9/00523* (2013.01); *A63B 2024/0012* (2013.01); *A63B 2220/30* (2013.01); *A63B 2220/44* (2013.01); *A63B 2220/833* (2013.01)

(56) References Cited

U.S. PATENT DOCUMENTS

| | | | |
|---|---|---|---|
| 7,234,351 B2 | 6/2007 | Perkins | |
| 7,766,757 B2 | 8/2010 | Brooks et al. | |
| 7,887,440 B2 * | 2/2011 | Wright | A63B 24/0003 473/409 |
| 8,257,191 B2 | 9/2012 | Stites et al. | |
| 8,337,335 B2 | 12/2012 | Dugan | |
| 8,587,114 B2 | 10/2013 | Papadourakis | |
| 8,616,989 B2 * | 12/2013 | Bentley | A61B 5/1122 473/215 |
| 8,696,482 B1 | 4/2014 | Pedenko et al. | |
| 8,715,096 B2 | 5/2014 | Cherbini | |
| 8,781,610 B2 | 7/2014 | Han | |
| 8,864,598 B2 * | 10/2014 | Worobets | G06F 17/40 473/219 |
| 8,989,441 B2 | 3/2015 | Han et al. | |
| 9,375,624 B2 * | 6/2016 | Boyd | A63B 69/36 |
| 10,080,941 B2 * | 9/2018 | Brekke | A63B 60/46 |
| 2002/0077189 A1 | 6/2002 | Tuer | |
| 2003/0207718 A1 | 11/2003 | Perlmutter | |
| 2005/0277483 A1 * | 12/2005 | Peterson | A63B 53/0466 473/282 |
| 2007/0270214 A1 | 11/2007 | Bentley | |
| 2010/0151956 A1 | 6/2010 | Swartz et al. | |
| 2012/0295726 A1 | 11/2012 | Cherbini | |
| 2013/0267335 A1 | 10/2013 | Boyd | |
| 2015/0018130 A1 * | 1/2015 | Johnson | G06K 9/00342 473/409 |

\* cited by examiner

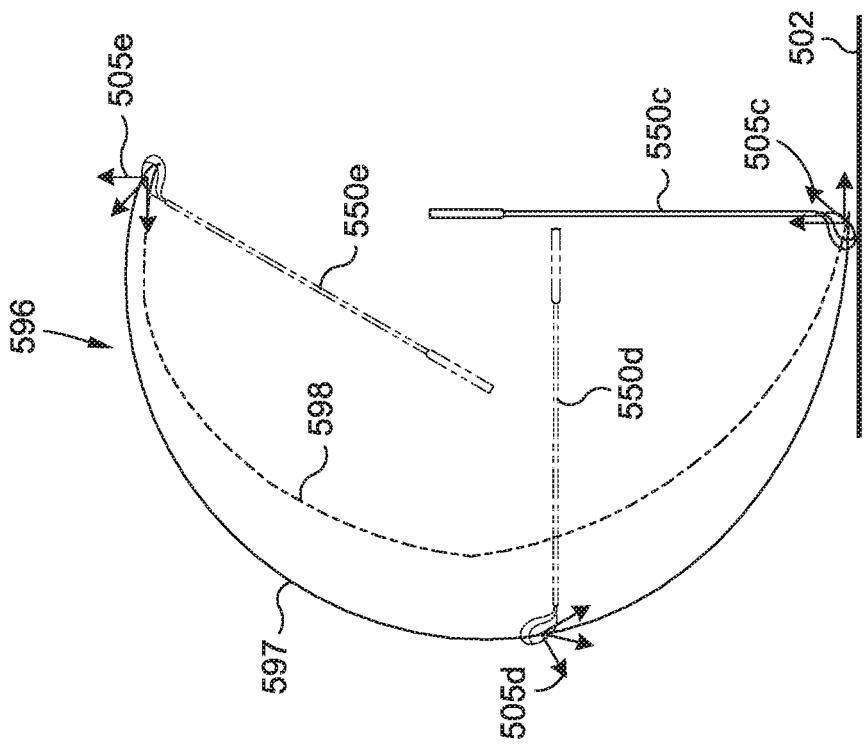
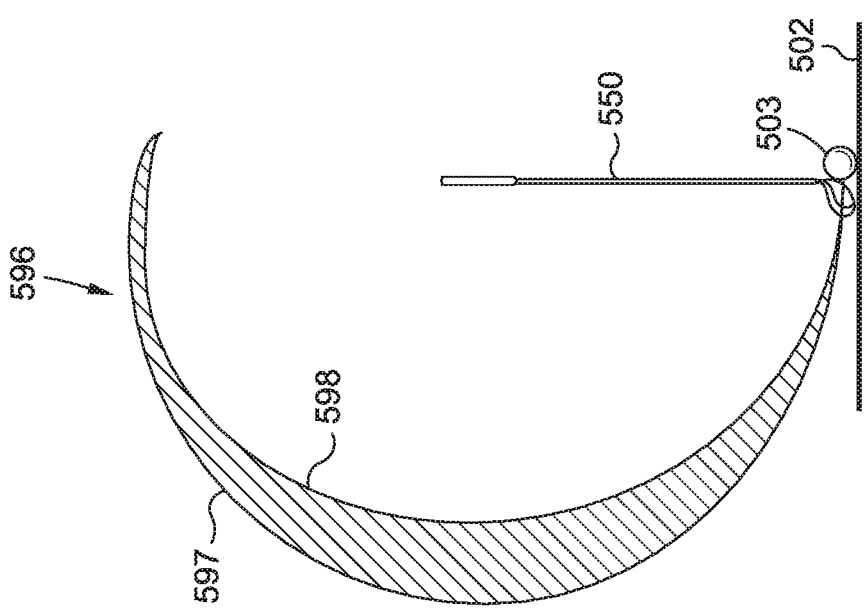

METHOD, SYSTEM, AND APPARATUS FOR ANALYZING A SPORTING APPARATUS

CROSS REFERENCE TO RELATED APPLICATIONS

The present application is a continuation-in-part of U.S. patent application Ser. No. 14/848,083, filed on Sep. 8, 2015, which claims the benefit of U.S. Provisional Patent Application Ser. No. 62/188,393 filed Jul. 2, 2015, the disclosures of which are hereby incorporated by reference in their entirety.

BACKGROUND

Golf club fitting has been around since the early stages of the golf game. Early systems utilized manual measurements of golf clubs and players to determine the proper fit for each player. However, with the need for more advanced and accurate fitting methods and systems, sports enthusiasts have turned to technical innovations in an effort to improve their game, including the use of monitoring devices used to determine and display information specific to the enthusiast, such as a golfer's swing path. Golfers and golf club equipment manufacturers have been increasingly relying upon sensors and monitors to evaluate a golfer's swing. Sensors and monitors may track conditions, such as club head speed, attack angle, launch angle, golf ball spin rate and spin direction, and so on. And sellers of golf club equipment, including outlets that specialize in golf club fitting, increasingly rely on such sensors and monitors to assist a prospective purchaser in selecting golf clubs that best match their particular golf swing characteristics.

One such monitoring device that is commercially available is the "SB2" sensor, available from Swingbyte, LLC (previously Swingbyte, Inc.) of Chicago, Ill. Such sensors, as described in U.S. Pat. No. 8,696,482, incorporated herein by reference, are typically removeably attached to the shaft of a golf club, for example with a clamping mechanism, or fixed to the shaft, for example, with an adhesive. As is now known by virtue of co-pending U.S. patent application Ser. No. 14/564,933, filed Dec. 9, 2015, assigned to the assignee of the present application, hereby incorporated by reference, monitoring devices may also be placed within sporting apparatus, such as the head, shaft, and/or grip of golf clubs.

Such monitoring devices capture and analyze golf swing (or other sporting apparatus motion) data by attaching the monitoring device to a golf club either below the grip or on the cap, or by integrating the sensor into the shaft or head. After hitting a shot or swinging the golf club (or other sporting apparatus), players and instructors can view an interactive, three-dimensional animation of the swing, along with key metrics, such as club head speed, path, plane, and various angles at impact. Such monitoring devices may use a transmitter to send processed linear and angular movement data that defines a sporting apparatus swing, e.g., a golf club swing, to a receiver on a mobile device, such as a smart phone, tablet computer, or laptop computer. A computer application running on the mobile device may receive the processed data, process the data further and display a graphical representation of the entire swing with comprehensive statistics associated with the swing.

Yet, even with the implementation of sensors such as those discussed above, and the wide use of digital measurements in fitting golf clubs, fitting methods that utilize parameters of the swing of the golfer as measured by a sensor attached to a golf club have yet to be widely accepted and implemented.

SUMMARY

The following presents a general summary of aspects of the disclosure in order to provide a basic understanding thereof. This summary is not an extensive overview of the disclosure. It is not intended to identify key or critical elements of the disclosure or to delineate the scope of the disclosure. The following summary merely presents some concepts of the disclosure in a general form as a prelude to the more detailed description provided below.

In one implementation of the present disclosure, a computing device is disclosed comprising: a computer readable memory configured to store instructions; and a processor configured to execute the instructions to: receive data generated in response to a motion of a sporting apparatus, the data including a first data relating to a first characteristic of the motion of the sporting apparatus; analyze the data to determine a skill value; determine a recommended sporting apparatus from a group of at least two sporting apparatuses based on the skill value; and transmit information relating to the recommended sporting apparatus, wherein the first data is based on a comparison between at least two different directional segments of a path created by a first location on the sporting apparatus during the motion of the sporting apparatus.

In another implementation, a computing device is disclosed comprising: a display; a computer readable memory configured to store instructions; and a processor configured to execute the instructions to: receive data generated in response to a motion of a sporting apparatus, the data including a first data relating to a first characteristic of the motion of the sporting apparatus, the first characteristic including a first attribute of a backswing of a swing path of a location on the sporting apparatus and a second attribute of a downswing segment of the swing path of the location on the sporting apparatus; analyze the data to determine a skill value by comparing the first attribute and the second attribute; and transmit the skill value to the display.

In yet another implementation, a method for determining a recommended sporting apparatus is disclosed, the method comprising: receiving data generated in response to a motion of a sporting apparatus, the data including a first data relating to a first characteristic of the motion of the sporting apparatus, the first characteristic including a first attribute of a first directional segment of a swing path of a location on the sporting apparatus and a second attribute of a directional segment of the swing path created by the first location on the sporting apparatus; analyzing the data to determine a skill value by comparing the first attribute and the second attribute; determining a recommended sporting apparatus from a group of at least two sporting apparatuses based on the skill value; and transmitting information relating to the recommended sporting apparatus.

In another implementation of the present disclosure, a system is disclosed, the system comprising: a reference golf club; a sensor engaged with the reference golf club; and a computing device, the computing device comprising: a computer readable memory configured to store instructions; and a processor configured to execute the instructions to: receive data generated by the sensor in response to a motion of the reference golf club, the data including a first data relating to a first characteristic of the motion of the reference golf club, the first characteristic based on at least two different directional segments of a swing path created by a first location on the reference golf club during the motion of the reference golf club; analyze the data to determine a skill value; determine a recommended golf club from a group of at least two golf clubs based on the skill value; and transmit information relating to the recommended golf club.

BRIEF DESCRIPTION OF THE DRAWINGS

The present disclosure is illustrated by way of example and not limited in the accompanying figures, in which like reference numerals indicate similar elements throughout, and in which:

FIGS. 5A-5F illustrate various representations of swing parameters associated with a golf club swing, according to one implementation of the present disclosure.

DETAILED DESCRIPTION

Figure 1:
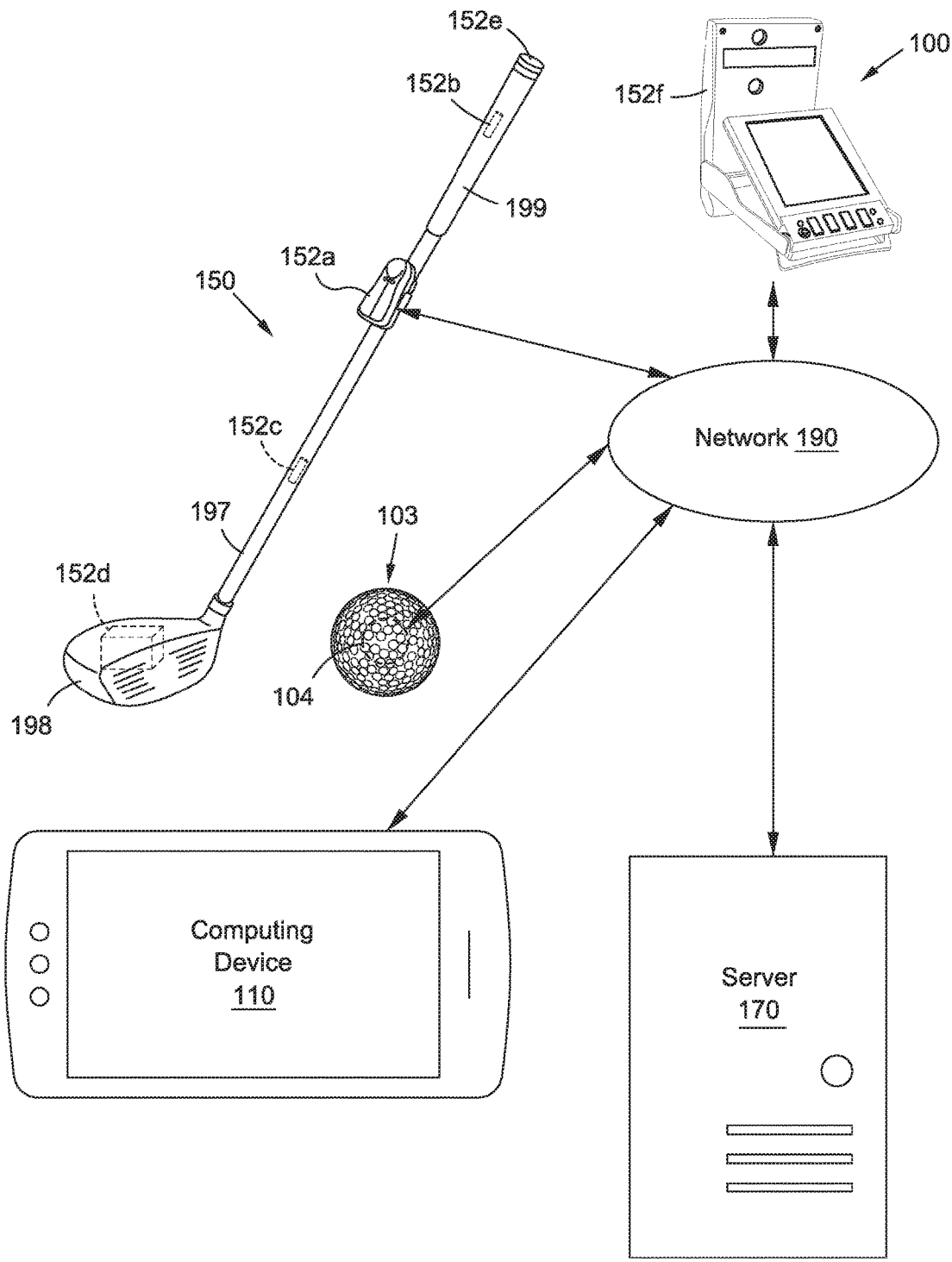
FIG. 1 is an illustration of a system for analyzing a sporting apparatus, according to one implementation of the present disclosure.

It should be noted that for simplicity and clarity the specification is directed toward the use of golf clubs, such as reference golf club 150 of FIG. 1, for example. However, the specification is not intended to be limited to only implementations including golf clubs. As such, the use of the term golf club (and implementations thereof) throughout the specification is intended to include substitution with any suitable sporting apparatus (and like implementations thereof), including baseball bats, softball bats, cricket bats, hockey sticks, tennis rackets, squash rackets, racquetball rackets, badminton rackets, lacrosse sticks, a boxing glove, and further includes sports apparel, and devices such as video game controllers intended to mimic such sporting apparatus. In addition, sporting apparatuses that may impact or be associated with an impact with a device are also included within suitable sporting apparatuses that may be used in lieu of a golf club in the specification. For example, a shoe configured to kick a soccer ball or football, or apparel, such as a golf glove, body suit, watch, or helmet, that a user might wear when causing an impact, are all included within the term sporting apparatus.

Referring to FIG. 1, FIG. 1 is an illustration of a system for analyzing a sporting apparatus, according to one implementation of the present disclosure. FIG. 1 includes reference golf club 150, golf ball 103, sensor 152a, sensor 152b, sensor 152c, and sensor 152d, and sensor 152e (hereinafter referred to collectively as sensors 152), network 190, server 170, and computing device 110. Reference golf club 150 includes golf club head 198, golf club grip 199, and golf club shaft 197. The golf ball 103 includes ball sensor 104. Each of the sensors 152, network 190, server 170, reference golf club 150, and computing device 110 will described in more detail with reference to FIG. 2A-FIG. 7.

The reference golf club 150 includes any type of golf club, including a driver, an iron, a wedge, or a putter, for example. Preferably, reference golf club 150 includes the type of golf club being analyzed by a system 100. For example, if a user of the reference golf club 150 is utilizing the system 100 to analyze his/her swing during use of a driver, then reference golf club 150 is preferably also a driver in order to generate more accurate results.

The network 190 enables communication between sensors 152, computing device 110, and server 170. Although network 190 is illustrated as being a single network, the illustration of FIG. 1 is not intended to limit the scope of the disclosure. As such, the network 190 may include any number of networks in communication with each other, and/or any number of separate networks not in communication.

The computing device 110 is configured to receive and/or transmit data over the network 190 from and/or to sensors 152 and/or server 170. The computing device 110 may be a desktop computer, a laptop computer, a tablet computer, a mobile device, a wearable device, such as a watch, or any other suitable device capable of receiving and/or transmitting data and operating a software program, for example, as described in U.S. application Ser. No. 14/694,568, filed Apr. 23, 2015, assigned to the assignee of the present application, and incorporated in its entirety by reference herein. Although the computing device 110 is illustrated as being a single computing device, the illustration of FIG. 1 is not meant to limit the scope of the disclosure. In some implementations, there may be any number of computing devices in communication with each other and/or the network 190.

The server 170 is configured to receive and/or transmit data over the network 190 from and/or to the sensors 152 and/or the computing device 110. Although the server 170 is illustrated as being a single server, the illustration of FIG. 1 is not meant to limit the scope of the disclosure. Thus, the server 170 may include any number of servers in communication with each other and/or the network 190.

The sensors 152 are configured to generate and record data relating to characteristics of motion of the reference golf club 150 during a motion of the reference golf club 150, such as a full swing including a backswing and a downswing of the reference golf club 150. The sensors 152 may be associated with the reference golf club 150 in a variety of ways, including attached externally to the shaft 197, for example, such as sensor 152a, embedded within the shaft 197, such as sensor 152c, embedded within the grip 199 portion of the shaft 197, such as sensor 152b, inserted into the butt end of the grip, such as sensor 152e, or embedded within the club head 198, such as sensor 152d, for example, as illustrated and described in U.S. application Ser. No. 14/488,140, filed Sep. 16, 2014, assigned to the applicant of the present application, and incorporated in its entirety by reference herein. In addition, the sensors 152 may be plugged into the butt end of the shaft 197, such as sensor 152e. In some implementations, at least one of the sensors 152 may be detached and separated from (e.g., external to) the reference golf club 150, such as that of sensor 152f, and may record swing data using cameras and motion detectors, for example. Commercially available examples of sensor 152f are the Foresight Sports™ GC2 Smart Camera System and the Trackman 4 by Trackman™ Golf. Although various different locations for the sensors 152 are illustrated in FIG. 1, the specification is not intended to be limited to the illustrations of FIG. 1. For example, the sensors 152 may be embedded within, or attached to, the golf club 150 at any location. In addition, any number of sensors 152 may be included in and/or on the reference golf club 150, or external and detached from the reference golf club 150. For example, in some implementations, only one of the sensors 152 may be utilized, while in other implementations, multiple sensors 152 may be utilized to generate data at different locations on the golf club 150.

The sensors 152 may each include a dedicated housing for protecting the components of the sensors 152, or alternatively, the sensors 152 may utilize the interior walls or surface(s) of the reference golf club 150 as a housing.

The sensors 152 may be attached to or inserted within the shaft and/or the club head of the reference golf club 250 using clamping mechanisms, adhesive, plugs, mechanical fasteners, or another suitable method capable of holding the sensors 152 in place during a full swing of the reference golf club 150.

The ball sensor 104 may function similarly to the sensors 152 except for the ball sensor 104 is located within the golf ball 103. The ball sensor 104 therefore may measure impact conditions such as launch angle, spin rates, deformation, and other data relating to the golf ball 103. In addition, the ball sensor 104 may measure the distance the golf ball 103 travels after impact, including carry distance and roll distance, and may also track the location of the ball on the course, using GPS, for example. The ball sensor 104 may transmit the data collected over the network 190, and may include similar circuitry and components as the sensors 152, which will be described in greater detail with reference to the sensor 252 in FIG. 2A and FIG. 2B.

Figure 2A:
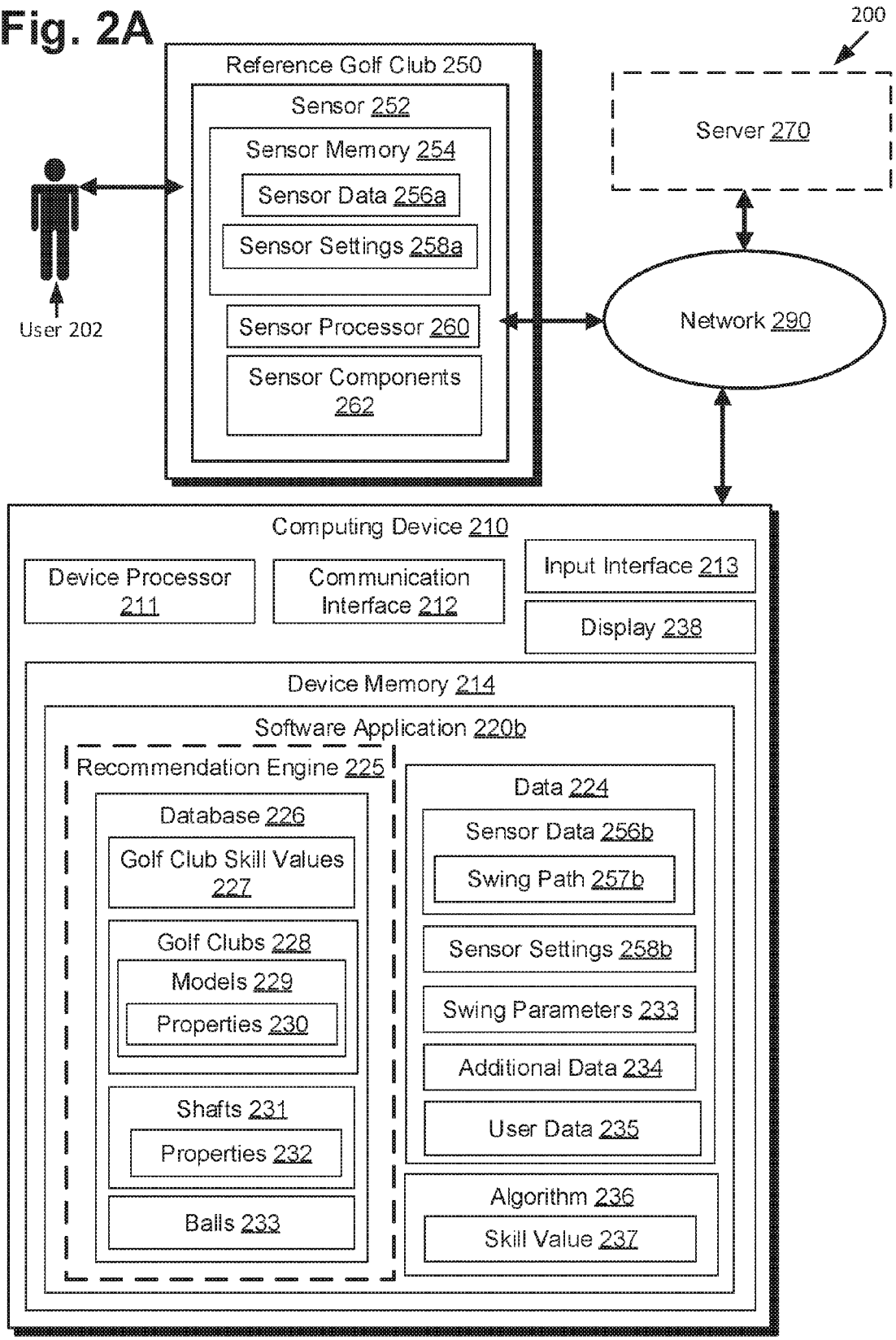
FIG. 2A is an illustration of a system for analyzing a sporting apparatus, according to one implementation of the present disclosure.

Now referring to FIG. 2A, FIG. 2A is an illustration of a system for analyzing a sporting apparatus, according to one implementation of the present disclosure. System 200 of FIG. 2A includes user 202, reference golf club 250, sensor 252, server 270, network 290, and computing device 210. The sensor 252 includes the sensor memory 254 configured to store sensor data 256a and sensor settings 258a, sensor processor 260, and sensor components 262. The computing device 210 includes device processor 211, communication interface 212, input interface 213, display 238, and device memory 214. The device memory 214 is configured to store software application 220b which includes recommendation engine 225, data 224, and algorithm 236. The recommendation engine 225 includes database 226 which includes golf club skill values 227, golf clubs information 228 which includes identification of model 228, properties 230, and component information, including for shafts 231 which includes properties 232, and balls 233. The data 224 includes sensor data 256b which includes swing path 257b, sensor settings 258b, swing parameters 233, additional data 234, and user data 235. The algorithm 236 includes skill value 237.

As used herein, the sensor data 256 may also be referred to as swing data.

It should be noted that the reference golf club 250, the sensor 252, the server 270, the network 290, and the computing device 210 correspond respectively to the reference golf club 150, the sensors 152, the server 170, the network 190, and the computing device 110 of FIG. 1.

System 200 includes network 290 that is configured to allow communication between the sensor 252, the server 270, the computing device 210, and any other devices in communication with the network 290. The network 290 may include any medium that facilitates transfer of a program code from one place to another, including, for example, implementations where the software is transmitted from the server 270, a website, the computing device 210, the sensor 252, or another remote source. The network 290 may utilize coaxial cable, fiber optic cable, twisted pair, digital subscriber line (DSL), or wireless technologies such as infrared, radio, which includes Bluetooth™ and ZigBee™, and microwave. The network 290 may be a local area network (LAN) or a wide area network (WAN). When system 200 is used in a LAN networking environment, the computing device 210, the server 270, and the sensor 252 are connected to the LAN through a network interface or adapter. When used in a WAN networking environment, the computing device 210, the server 270, and the sensor 252 may include a modem or other means for establishing communications over the WAN, such as the Internet.

In some implementations, the network 290 may be connected to any number of the sensors 252 such that the server 270 and/or the computing device 210 receive the data 224 from each of the sensors 252. As a result, the software application 220b can be dynamically updated using new information from each of the sensors 252, i.e., has the capability of learning. For example, the recommended golf clubs 228, shafts 231, and balls 233 may be compared to real-life or digital data, i.e., validation data, that either validate or invalidate the results of the recommendation engine 225. In such an example, if the golf club recommended actually does not provide the user 202 with the most carry distance, for example, this information (i.e., an indication of an incorrect recommendation) can be input back into the database 226 to dynamically update the associated golf club skill values 227 and/or swing parameters 233 associated with the recommended golf club to match the skill value 237 and/or swing parameters 233 of the user 202 during the swing of the reference golf club 250. As a result, the feedback can be used to dynamically update the algorithm 236 such that more accurate recommendations are made by the recommendation engine 225.

The system 200 further includes the server 270 which will be described in further detail below with reference to FIG. 2B. It should be noted that the server 270 is illustrated with dashed lines to indicate that the server 270 may not be necessary in all implementations. For example, in implementations where the computing device 210 is capable of handling the data storage requirements of the software application 220b, the server 270 may not be necessary.

The system 200 further includes the sensor 252 configured to record sensor data 256a before, during, and after a motion of the reference golf club 250. The sensor 252 is configured to be capable of recording three dimensional motion of the reference golf club 250. The sensor 252 may be a sensor similar to that of the Swingbyte "SB2" sensor described above, or may be any sensor capable of recording the motion of the reference golf club 250. In addition, the sensor 252 may be located in a golf ball, such as the sensor 104 in the golf ball 103 of FIG. 1.

The sensor 252 includes the sensor memory 254 and the sensor processor 260. The sensor processor 260 is configured to execute computer-readable instructions that are stored in the sensor memory 254. The instructions may be, for instance, instructions for gathering sensor data 256a according to the sensor settings 258a, and may further include instructions for utilizing the sensor components 262, including, for example, a three-axis accelerometer, a three-axis gyroscope, and a three-axis magnetometer. The sensor processor 260 may access the sensor memory 254 by way of a system bus, for example. The sensor 252 also includes a communication interface, similar to that of the communication interface 212 of the computing device 210, configured to allow external devices, such as the server 270 and the computing device 210, to communicate with the sensor 252 and also allow the sensor 252 to communicate with the external devices. For example, in some implementations, the sensor 252 may receive instructions for execution by the sensor processor 260 from an external device.

Various functions of the sensor memory 254 may be implemented in hardware, software, or any combination thereof. If implemented in software, the functions may be stored as one or more instructions or code and transmitted over a computer-readable medium. A computer-readable storage media may include any available storage media that can be accessed by a computer, and more specifically by a processor, such as the sensor processor 260. By way of example, and without limitation, computer-readable storage media can comprise RAM, ROM, EEPROM, CD-ROM, or other optical disk storage, magnetic disk storage or other magnetic storage devices, or any other medium that can be used to carry or store desired program code in the form of instructions or data structures that can be accessed by a computer, e.g., sensor processor 260. In some implementations, the sensor 252 may use a flash memory to store the data and instructions.

The sensor components 262 may include a battery, and a battery charging connection, such as a USB or mini-USB port, for example. The sensor components 262 may further include a Global Positioning System (GPS) device, a clock, and other suitable devices necessary to capture the sensor data 256a needed for system 200. For example, the GPS device within the sensor 252 may be used to assist in tracking the weather conditions, turf conditions, altitude conditions, or other information that may factor into the motion-gathered sensor data 256a of the reference golf club 250.

The sensor components 262 may include a circuit board onto which one or more subcomponents, such as microprocessors, transmitters, accelerometers, resistors, capacitors, etc., may be mounted, arranged and connected.

The sensor components 262 may include other features similar to inertial measurement units (IMU), inertial navigation systems (INS), and attitude heading and reference systems (AHRS), which enable measurements in nine degrees of freedom. These features may include accelerometers, gyroscopes, and/or magnetometers.

The sensor components 262 may further include a three-axis accelerometer. The accelerometer measures the proper acceleration of the reference golf club 250 during a motion of the reference golf club 250. Due to the three-axis measurements, the accelerometer can measure proper acceleration as a vector quantity and can be used to sense orientation, coordinate acceleration, vibration, and shock of the reference golf club 250.

The sensor components 262 may also include a three-axis gyroscope. The gyroscope is primarily used to measure and maintain orientation of the reference golf club 250 throughout a motion of the reference golf club 250. The three-axis gyroscope also measures angular momentum.

The sensor components 262 may further include a three-axis magnetometer. The magnetometer is used to let the user 202 set a target line for the motion of the reference golf club 250. This is important because each user, including the user 202, has a variation in how they address the golf ball and in their natural degree of slice or hook. Thus, at address, the user 202 chooses a target line, and the actual swing can be compared to that target line for analysis. Magnetometers are also used to help determine the orientation of the sensor 252 during a motion of the reference golf club 250, such as during a swing of the reference golf club. It should be noted that other devices and/or features may be utilized by the sensor 252 to accomplish the same accounting for variations and orientation as provided by the magnetometer, such as the gyroscope mentioned above.

Each of the sensor components 262 described above may function similarly to the accelerometer, gyroscope, and magnetometer described in U.S. Pat. No. 8,696,482, hereby incorporated by reference. All of the data collected by the sensor components 262 may be stored in the sensor data 256a. In addition, each of the sensor components 262 may collect the sensor data 256a based on the sensor settings 258a stored in the sensor memory 254, as will be discussed in further detail below.

The sensor memory 254 includes the sensor data 256a. The sensor data 256a includes all of the data collected by the sensor components 262 of the sensor 252 before, during, and after motion of the reference golf club 250, such as after a full or partial swing of the reference golf club 250. For example, and without limitation, the sensor data 256a, and/or parameters derived from the sensor data 256a, may include the velocity of any location on the reference golf club 250, including at the sensor 252 location during the motion of the reference golf club 250, the top of the backswing location measured by the point where the reference golf club 250 reverses direction, the location of the reference golf club 150 at address, the torque, the calculated launch direction and velocity of a golf ball struck by the reference golf club 250 based on the impact data calculated by a golf club attached sensor or a golf ball attached sensor, the angle of attack of the golf club head, the club face loft and lie angles measured at address and at impact, the deviation from the address swing plane throughout the swing of the reference golf club 250, the point of release of the wrist of the user 202 during the downswing, the swing tempo/club head velocity at all points throughout the swing, and the shaft deflection based on the reference golf club 250 specifications included in the sensor settings 258a and the calculated torque. In addition, any data measured from the sensors as outlined in U.S. Pat. No. 8,696,482, are hereby incorporated by reference.

The sensor memory 254 further includes the sensor settings 258a. The sensor settings 258a includes data relating to the reference golf club 250 such as the model identification of the golf club or any component thereof, club length, the shaft length, the shaft flex profile, the club type, the volume of the club head, the loft of the club head, the location of the sensor 252 on the golf club, and other data necessary to enable the sensor 252 to capture the sensor data 256a accurately. The sensor settings in some implementations are stored within the sensor at the factory. In some implementations, such information may input by a user or otherwise subsequent to manufacture. In some embodiments, the sensor is provided such setting information by engagement with an electronically readable identification element associated with the reference club, e.g. a barcode, RFID chip, electronically engageable port, or the like. The sensor settings 258a factor into the sensor data 256a directly. For example, in an implementation where the sensor 252 is attached to the shaft of the reference golf club 250, the location of the sensor 252, the length of the shaft, and the club head properties of the reference golf club 250 factor directly into a calculation of other locations of the golf club head at address because the information is used to extrapolate the sensor 252 measurements from the sensor's actual location in space to another location on the club head.

In such an example, the sensor 252 may be configured to enable projection of a 3D vector onto the geometric center of the club face, for example, from a sensor attachment location remote from the geometric center (e.g. a location on the shaft) and determine and record the orientation, velocity, and location data of a 3D vector throughout a swing of the reference golf club 250. In order to determine the location of the geometric center of the face of the club head, the sensor 252 utilizes the sensor settings 258a including the sensor 252 location on the reference golf club 250, the length of the shaft, the orientation of the club head with respect to the sensor 252, and other necessary sensor settings 258a.

In some implementations, the sensor settings 258a may be generic such that any reference golf club 250 can be used to calculate the sensor data 256a. However, more accurate results are captured when the sensor settings 258a include the data of the actual reference golf club 250 being used in capturing the sensor data 256a.

In addition, the sensor settings 258a may include data relating to the user 202 such as the height, age, weight, gender, or golf handicap of the user 202. As such, the sensor settings 258a relating to the user 202 may also be factored into the calculation of the sensor data 256a.

In an implementation where the sensor 252 is located within a golf ball, such as golf ball 103 of FIG. 1, the sensor settings 258 may include the material properties, aerodynamic properties, mass, size, shape, and other information pertaining to the golf ball.

In addition, the computing device 210 and/or the server 270 may transmit additional or updated sensor settings 258a to the sensor 252. The additional or updated sensor settings 258a may include the user data 235 and the additional data 234. For example, the sensor settings 258a may be dynamically updated for each user 202 and location of use of the reference golf club 250, in order to record more accurate and real-time data. As discussed above, the sensor settings 258a are utilized in generating the sensor data 256a, so as the sensor settings 258a are updated, so too is the sensor data 256a.

The system 200 includes the computing device 210 configured to communicate with the sensor 252 and the server 270 over the network 290. The computing device 210 may include a computer, a mobile device, a tablet computer, a wearable device including processing capabilities such as a smart watch, or any other device capable of receiving and/or analyzing data received from the sensor 252.

The computing device 210 includes the device memory 214 and the device processor 211. The device processor 211 is configured to execute computer-readable instructions that are stored in the device memory 214. The instructions may be, for instance, instructions for receiving, transmitting, or analyzing sensor data 256a/256b. The device processor 211 may access the device memory 214 by way of a system bus, for example. The computing device 210 also includes a communication interface 212 configured to allow external devices, such as the server 270 and the sensor 252, to communicate with the computing device 210 and also allow the computing device 210 to communicate with the external devices over the network 290. For example, in some implementations, the computing device 210 may receive data and or instructions for execution by the device processor 211 from an external device.

Various functions of the device memory 214 may be implemented in hardware, software, or any combination thereof. If implemented in software, the functions may be stored as one or more instructions or code and transmitted over a computer-readable medium. A computer-readable storage media may include any available storage media that can be accessed by a computer, and more specifically by a processor, such as the device processor 211. By way of example, and without limitation, computer-readable storage media can comprise RAM, ROM, EEPROM, CD-ROM, or other optical disk storage, magnetic disk storage or other magnetic storage devices, or any other medium that can be used to carry or store desired program code in the form of instructions or data structures that can be accessed by a computer, e.g., device processor 211. In some implementations, the computing device 210 may use a flash memory to store the data and instructions.

The computing device 210 further includes input interface 213. Input interface 213 may include a keyboard, a mouse, a microphone, a display, a joystick, a game pad, a satellite disk, a scanner, or other input devices. These and other input devices are often connected to the device processor 211 through a serial port interface that is coupled to the system bus, but may be connected by other interfaces, such as a parallel port, game port, or universal serial bus (USB), for example.

The computing device 210 further includes a display 238. The display 238 may be a monitor or other type of display device also connected to a system bus via an interface, such as a video adapter. The display 238 may include a plasma, light emitting diode (LED), organic LED, liquid crystal display (LCD), or other suitable display technology. In some implementations, such as where the computing device 210 is a mobile device or a tablet computer, the display 238 may be a touch screen device capable of receiving inputs from a user, such as user 202, via the display 238. In such an implementation, the display 238 also functions as a component of the input interface 213.

The display 238 is configured to display the displayable information of the software application 220b, which may include the data 224, the skill value 237, and any information output from the recommendation engine 225, including recommended golf clubs, shafts, and balls. As such, the software application 220b is configured to transmit the displayable information to the display 238 for visualization and interaction by a user of the computing device 210.

The computing device 210 further includes the software application 220b. The software application 220b is configured to analyze data received from the sensor in order to determine the skill value 237 utilizing the algorithm 236 and to determine the recommended golf clubs 228, shafts 231, and balls 233 utilizing the recommendation engine 225. The software application 220b may be configured to provide feedback about the swing of the user 202, such as by providing the user 202 with a skill value 237 or displaying the swing path 257b and features of the swing path 257b of the user 202 on the display 238 for the user 202 to visualize and interpret. In addition, the software application 220b may be configured to provide a recommended golf club, shaft, or ball from the database 226 based on the analyzed data 224 received from the sensor 252. The software application 220b may be an application designed for a mobile device, a tablet, a computer, or a wearable device, for example, or the software application 220b may be accessed using a web browser on the computing device 210.

In implementations where the software application 220b is accessed using a web browser, the recommendation engine 225 may be stored externally to the computing device 210, such as on the server 270, and accessed by the computing device 210 over the network 290. In implementations where the software application 220b is an application designed for a mobile device, a tablet, or a computer, the software application 220b may include all of the information, algorithms, etc. necessary for the software application 220b to function, thus eliminating the need for the server 270. However, some implementations may utilize both the server 270 and the computing device 210 when operating the software application 220b, whether the software application 220b is accessed via a web browser or configured as an application for a mobile device, a tablet, or a computer, for example.

The software application 220b includes the data 224. It should be noted that the sensor data 256b and the sensor settings 258b correspond respectively to sensor data 256a and sensor settings 258a of sensor 252. Software application 220b is configured to receive the sensor data 256b and the sensor settings 256b from sensor 252 over the network 290, such as a Bluetooth™ network, for example.

The software application 220b is configured to analyze the data 224. For example, after the computing device 210 receives the sensor data 256b from the sensor 252, the software application 220b analyzes the sensor data 256b to determine the swing path 257b of the reference golf club 250 during a swing by the user 202. The sensor data 256b may include three-axis orientation, three-axis velocity, three-axis acceleration, and three-axis location of the club head of the reference golf club 250 during the swing, and after analyzing the sensor data 256b, the software application 220b models a three-dimensional (3D) swing path 257b. The 3D swing path 257b may be again analyzed in determining a length ratio, for example, where the length ratio may be, for example, the distance a location on the club head travels during a backswing as compared to the distance the location on the club head travels during a downswing. In some implementations, the 3D swing path 257b may also be displayed on the display 238 and configured for manipulation by a user of the computing device 210. The swing path 257b will be described in greater detail below.

The data 224 also includes the sensor settings 258b. The software application 220b is also configured to utilize the sensor settings 258b in analyzing the data 224. Although the sensor 252 may utilize the sensor settings 258b in calculating the sensor data 256a, as discussed above, the software application 220b may also utilize the sensor settings 258b in further analyzing of the data 224.

The data 224 further includes the swing parameters 233. The swing parameters 233 include a plurality of different parameters of the swing of the reference golf club 250, and/or characteristics of a motion of the reference golf club 250, based on the sensor data 256b received from the sensor 252. The swing parameters 233 are utilized in generating the algorithm 236 and ultimately the skill value 237, which is utilized by the recommendation engine 225.

As used herein, the term "release" is defined as the release of the wrists by the user 202 during the downswing of the reference golf club 250 in order to position the club face for impact. For practical purposes herein, release is assumed to occur at a point in time during the downswing (i.e., the release point) when the longitudinal axis of the shaft of the reference golf club 250 is substantially parallel with the ground plane, herein referred to as the ¾ point in the swing.

As used herein, the term "swing path" is defined as the path created by a location on the reference golf club 250 during a motion of the reference golf club 250, such as a swing of the reference golf club 250. For example, the swing path 257 may be the path created by the club head of the reference golf club 250 during a full swing. In such an example, the club head creates a 3D path of the backswing and the downswing, where the path includes the orientation, velocity, and position of the club head throughout the full swing. This may be accomplished by recording the orientation, velocity, and location data of a 3D vector having a projected location on the geometric center of the face of the club head, for example. Although the sensor 252 may be mounted on the shaft, in the grip, etc., the sensor 252 utilizes the sensor settings 258a to determine the location of the geometric center of the face of the club head of the reference golf club 250 and records the sensor data 256a from that location. Each of plural locations on the reference golf club 250 may correspond respectively to each of plural swing paths. Of course, location data may be projected onto other locations of the golf club, e.g., the golf club center of gravity, the golf club head center of gravity, or the golf club head geometric center. However, projection onto the geometric center of the face of the club head is preferred as it is indicative of the location of impact with a golf a ball.

It should be noted that FIGS. 5A-5E are incorporated below into the description of the swing parameters 233. FIGS. 5A-5E illustrate various representations of the swing parameters 233 and each include the swing path 596, the backswing segment 597, the downswing segment 598, the golf ball 503, the ground plane 502, and the reference golf club 550. It should be noted that the reference golf club 550 corresponds respectively to the reference golf club 250 of FIGS. 2A-2B.

Figure 5B:
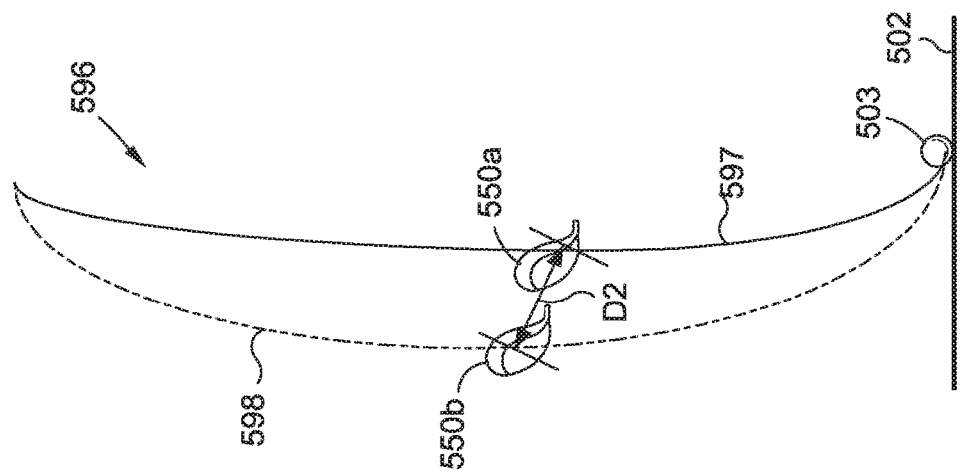
Figure 5A:
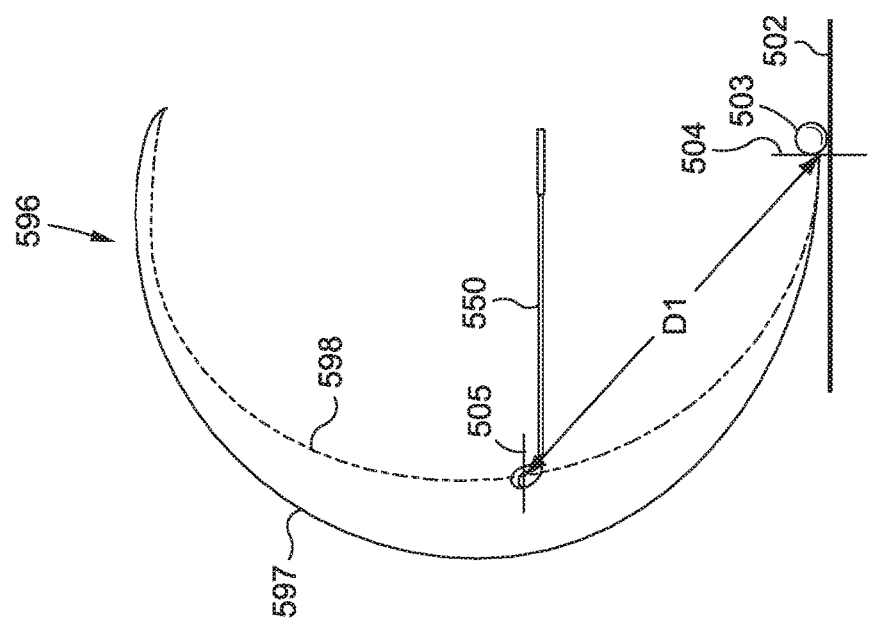

The swing parameters 233 include "distance to impact." As used herein, distance to impact is defined as the distance of a location on the reference golf club 550, e.g. the striking face, from its corresponding location when the golf club is in the original address position during the downswing and measured at the position of the golf club when at the release point. FIG. 5A illustrates one representation of the distance to impact, and includes the reference golf club 550 at the release point, i.e., the ¾ point of the swing path 596, which occurs when the longitudinal axis of the reference golf club 550 is parallel with the ground plane 502 during the downswing segment 598. As illustrated in FIG. 5A, the distance to impact may be defined as the distance D1, measured from the location on the reference golf club 550 at the original address position 504 to the location on the reference golf club 550 at the release point 505. In some implementations, the distance D1 may be measured as the straight line distance in 3D space between the release point 505 and the original address position 504. In other implementations, the distance D1 may be measured as the straight line distance as projected onto a two-dimensional (2D) plane. The swing path 596 may be considered from various vantage points, and thus, it is contemplated that the distance to impact measurement may be projected onto one of several virtual planes. For example, the distance to impact may be measured based on the swing path 596 projected onto a vertical 2D plane extending perpendicular to the face of the club head of the reference golf club 550 when the club head is at address.

However, the distance to impact measurement is not intended to be limited to a straight line measurement, but may, in some implementations, be measured as the distance along the downswing segment 598 of the swing path 596 in 3D space or as projected onto a 2D plane, similar to the 2D planes described above.

The swing parameters 233 further include "release ratio." As used herein, the release ratio is a comparison between the amount of time from the beginning of the downswing to the release point compared to amount of time during the downswing from the release point to impact.

The swing parameters 233 also include "swing path width." As used herein, the swing path width is defined as the maximum distance between the backswing and the downswing segments of the swing path measured perpendicular to the arc of the downswing. Similar parameters may be considered having interchangeable practical use with swing path width as may be described below in more detail. For example, a lateral swing path width may be considered to have similar informational value as swing path width, but measured as the maximum distance between the backswing and the downswing in a virtual horizontal plane (i.e., parallel to the virtual ground plane), limited to the region of the swing in which points on the downswing are laterally spaced from corresponding points on the backswing.

Another similar parameter that, for practical purposes herein, may be considered to be interchangeably functional with swing path width is a projected swing path width. Projected swing path width as used herein denotes a distance measured based on the swing path projection onto a two-dimensional (2D) plane. The swing path may be considered from various vantage points, and thus, it is contemplated that a swing path width may be projected onto one of several virtual planes. For example, with reference to the position of the golf club when oriented in an initial address position, the swing path width may be measured based on the swing path projected onto a vertical 2D plane extending parallel to the face of the club head of the reference golf club 250 when the club head is at address. FIG. 5B illustrates one representation of the projected swing path width measurement. The swing path 596 in FIG. 5B is projected onto the plane of the paper, where the plane of the paper extends parallel to the club face of the reference golf club 550 when the reference golf club 550 is at the original address position. FIG. 5B includes the reference golf club 550 at the ¼ point of the swing path 596 on the backswing segment 597 as reference golf club 550a, and further includes the reference golf club 550 at the ¾ point of the swing path 596 on the downswing segment 598 as reference golf club 550b. As such, the distance D2 is a measurement of the distance between a location on the reference golf club 550, such as at the geometric center of the face, at the ¼ point and at the ¾ point of the swing. It should be noted that the ¼ point of the swing is the point in the backswing when the longitudinal axis of the reference golf club 250 is parallel with ground plane 502.

However, in some embodiments, the swing path width may be measured based on the maximum distance between the backswing and the downswing segments of the swing path in 3D space, where each distance measurement is taken along a straight line extending perpendicular to the arc of the downswing).

The swing parameters 233 also include "swing path area." As used herein, the swing path area is defined as the area between the backswing and the downswing segments of the swing path. The swing path area may be measured based on the swing path projection onto a two-dimensional (2D) plane. For example, the swing path area may be measured based on the swing path projected onto a 2D vertical plane extending perpendicular to the face of the club head of the reference golf club 550 when the club head is oriented in an initial address position. Referring to FIG. 5C, FIG. 5C illustrates one representation of the swing path area measurement. As such, the swing path area is the area between the backswing segment 597 and the downswing segment 598 of the swing path 596, denoted by solid parallel lines in FIG. 5C.

The swing parameters 233 include "angular velocities." As used herein, the angular velocities is defined as the maximum angular velocity during the downswing of the reference golf club 550 about an axis extending parallel to the ground plane and through the club face of the reference golf club 550 when the club head is at the original address position.

The swing parameters 233 further include "maximum velocity." As used herein, the maximum velocity (of a location on a reference golf club, e.g., golf club 550) is defined as the maximum velocity achieved by a designated location on the reference golf club 550 during the swing. Maximum velocity may be considered, for example, at the geometric center of the face of the club head. For all practical purposes herein, it is contemplated that various recitations of "maximum velocity" below may also be considered substitutable with similar measurement values. For example, such recitations of "maximum velocity," as may be variously provided below in association with swing analysis systems, processes and/or apparatuses, are contemplated to be substitutable with a swing velocity value taken at a controlled, predetermined absolute location relative to a reference point (e.g., the geometric center of the striking face of the club head in an initial address position), relative to one or more locations regarding the geometric extent of the swing, and/or at an absolute or relative predetermined point in time during the swing.

Referring to FIG. 5D, FIG. 5D illustrates a non-limiting representation of various points in the swing where velocity may be measured in order to determine a maximum velocity.

For example, swing velocity values (associated with a specified location on a reference golf club, e.g., golf club 550) may be taken at a location on the reference golf club 550 at the ¼ (illustrated by reference golf club 550d), ½ (represented by reference golf club 550e), ¾, or impact (represented by reference golf club 550c) points of the swing. FIG. 5D further includes three-axis velocity vectors 505c, 505d, and 505e corresponding respectively to the reference golf club 550c, 550d, and 550e at various points in the swing. The three-axis velocity vectors are included to illustrate that the velocity of the location on the reference golf club 550 is measured about three axes at all points during the swing, and the magnitude of the velocity vectors at every point during the swing may be calculated to find the maximum velocity of the swing. In other embodiments, swing velocity values (associated with a specified location on the reference golf club 550) may be taken at a point in time relative to the swing duration, such as the time of impact.

The swing parameters 233 also include "velocity ratio." As used herein, the velocity ratio (of a specified spatial point along a specified swing path of a specified location on a reference golf club, e.g., golf club 250) utilizes the maximum velocity defined above, and is defined as the percentage of the maximum velocity of a measured swing velocity of the specified location on the reference golf club 250 at the specified point in the specified swing path. For example, the velocity ratio may be considered for the velocity of the center of the face of the club head at impact compared to the maximum velocity of the center of the face of the club head during a swing by the user 202. In another example, the velocity ratio may be considered for the velocity of the center of the face of the club head at the ¾ swing point compared to the maximum velocity of the center of the face of the club head during a swing by the user 202.

The swing parameters 233 further include "maximum club head speed." As used herein, club head speed (of a location on the reference golf club 250) is defined as the linear speed of a designated location on the club head of the reference golf club 250 during a swing. For example, assuming the designated location is the geometric center of the striking face of the reference golf club, the maximum club head speed is the maximum linear speed of the geometric center of the striking face during the downswing segment of a swing of the reference golf club 250.

The swing parameters 233 further include "attack angle." As used herein, attack angle is defined as an angle at which a geometric center of a face of a club head of the reference golf club 250 is moving at a point of impact with a golf ball or virtual golf ball measured with respect to, and in a plane perpendicular to, the ground plane. The positive angle of attack is when the club head strikes the ball moving upwards, and negative is when the club head is moving downwards when striking the ball.

The swing parameters 233 further include "impact lie." As used herein, the impact lie is the lie angle at impact. The lie angle is defined as the angle formed between the shaft axis and the sole of the reference golf club 250. The impact lie is defined as the angle formed between the shaft axis and the sole of the reference golf club 250 at impact. The impact lie is dependent on the swing of the golfer. In some implementations, when utilizing a sensor 252 of the type similar to sensor 152a-152e, the impact lie may not be a direct calculation from the sensor data 256 but may require combining initial lie, described below, the lie added, where the lie added is the value of the change in lie between initial lie and the lie angle at impact, and subtracting the club lie angle. This calculation is expressed below:

Impact Lie=Initial Lie+Lie Added−Club Lie

In other implementations, the impact lie 256 may be a direct calculation from the sensor data 256.

The swing parameters 233 further include "initial lie." As used herein, the initial lie is the lie angle before the swing. The lie angle is defined above with reference to impact lie.

The swing parameters 233 further include "dynamic lie." As used herein, dynamic lie is defined as the angle formed between the shaft axis and the ground plane at impact minus the angle formed between the shaft axis and the ground plane at setup (before the swing).

Figure 5F:
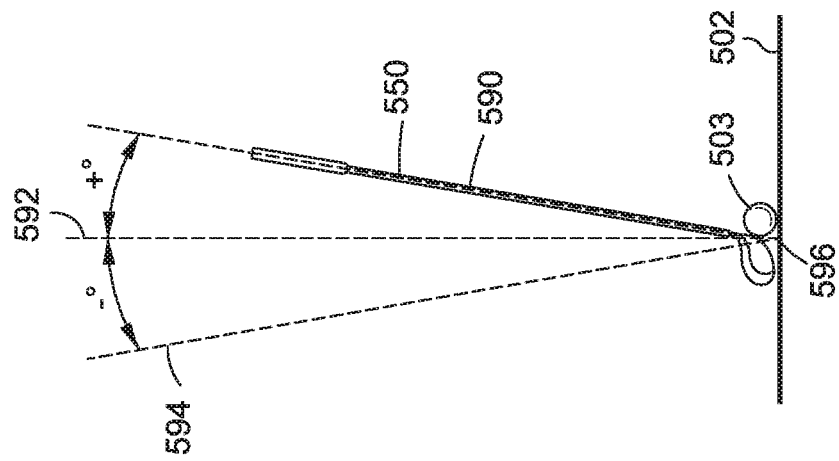

The swing parameters 233 further include "shaft lean." As used herein, the shaft lean is defined is as the angle formed between the shaft axis and a vertical line at impact, where the shaft axis and the vertical line extend from the same endpoint at the ground plane. Referring to FIG. 5F, the reference golf club 550 has a shaft axis 590 extending through a ground point 596. FIG. 5F also includes a vertical line 592 extending through the ground point 596, and negative degree line 594 extending through the ground point 596. The shaft lean in this image is the angle formed between the vertical line 592 and the shaft axis 590, indicated by a +°. The +° indicates that the shaft lean is a positive shaft lean, measured in degrees from the vertical line 592. The negative degree line 594 is included for purposes of illustrating what a negative shaft lean would look like, if the shaft axis 590 were aligned with the negative degree line 594. If the shaft axis 590 were aligned with the negative degree line 594, the shaft lean would be a negative shaft lean, indicated by the −°. The shaft lean is always measured in reference to the vertical line 592, and the shaft axis 590 and the vertical line 592 always must extend from the same ground point 596.

The swing parameters 233 further include "impact face angle." As used herein, the impact face angle is the face angle at impact. The face angle is defined as the angle between the target line and a line perpendicular to the plane of the striking face and extending from the geometric center of the striking face. The standard assumption for face angle is zero, meaning the plane of the striking face is perpendicular to the target line and thus the line perpendicular to the plane of the striking face is collinear with the target line. A positive face angle means the striking face is opened up, and thus the line perpendicular to the plane of the striking face points right of the target line. A negative face angle means the striking face is closed, and thus the line perpendicular to the plane of the striking face points left of the target line.

Figure 5E:
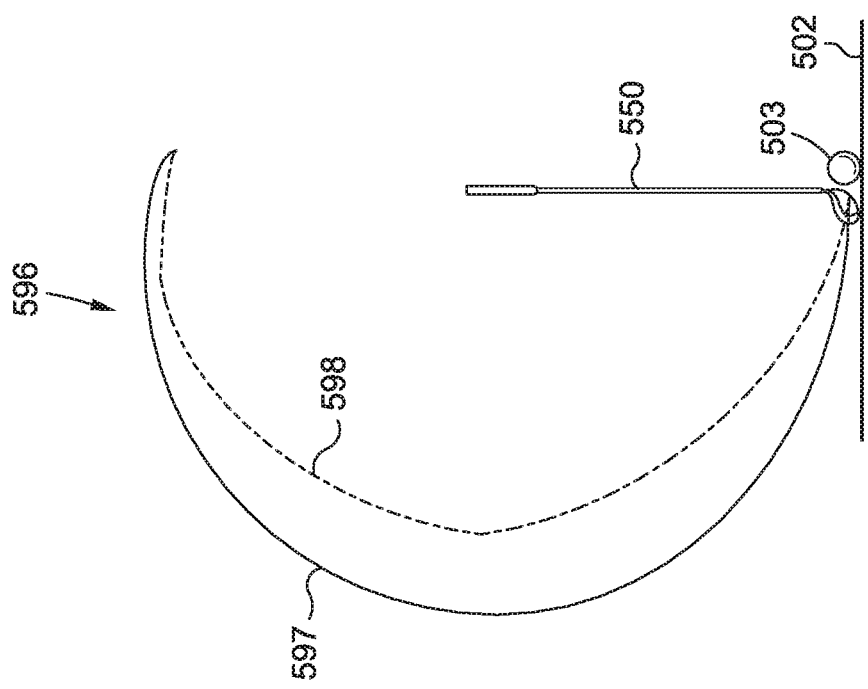

The swing parameters 233 include one or more comparisons between length aspects of the swing path. FIG. 5E illustrates a representation of a swing path. In some embodiments, the swing parameters 233 include a comparison between the respective lengths of at least two different directional components of the swing path 596 created by a location on the reference golf club 550 during the swing of the reference golf club 550. For example, and more specifically, the comparison may be between the length of the backswing segment 597 created by the geometric center of the face of the club head as compared to the length of the downswing segment 598 created by the center of face of the club head during the swing of the reference golf club 550. In addition or alternatively, the comparisons may include a comparison between the lengths of two different portions of the backswing segment 597 or two different portions of the downswing segment 598. In yet another example, the comparison may be between the length of a portion of the backswing segment 597 compared to a length of a portion of the downswing segment 598, and vice versa. Comparisons may also be measured based on the swing path projection onto a two-dimensional (2D) plane extending with respect to a reference coordinate. For example, a length comparison may be measured based on the swing path 596 projected onto a 2D vertical plane extending perpendicular to the face of the club head of the reference golf club 550 when the club head is oriented at an initial address position. In some implementations, length comparisons may also include a comparison of at least two different directional segments of the swing path 596 as measured in 3D space based on the distance traveled by a location on the club face of the reference golf club 550, for example.

The swing parameters may include "maximum tangential acceleration." As used herein, tangential acceleration is defined as a measure of how the tangential velocity of the face center of the club head of the reference golf club 250 changes with time. As such, maximum tangential acceleration is the maximum value for tangential acceleration recorded during a swing of the reference golf club 250.

Although a plurality of parameters are outlined above with respect to the swing parameters 233, the listed parameters are not intended to be limiting. For example, any number of other parameters may be utilized based on the sensor data 256b received from the sensor 252, including any parameters derived from the orientation, velocity, acceleration, and location of the reference golf club 250 during the swing by the user 202.

In some implementations, it is preferable to calibrate the sensor data 256 and/or the swing parameters 233 generated using the sensor data 256. Below outlines this calibration method that may be utilized.

For the measurement of certain swing parameters 233, including attack angle and maximum club head speed, the accuracy of sensors 252 that are attached to the reference club head 250, such as sensors 152a-152e in FIG. 1, is often not quite as accurate as using external sensors that are detached and separate from the reference golf club 250, such as sensor 152f of FIG. 1. This is primarily because some sensors of the types 152a-152e use values from a 3-dimensional vertices that is projected onto a location on the club head some distance away from the actual location of the sensor 152 itself. As such, the sensors 152a-152e are not taking measurements directly from the location the swing parameter 233 is based on. In contrast, the sensor 152f can more accurately generate values from the exactly location on the club head being measured for certain swing parameters 233.

As such, in order to improve the accuracy of the swing parameter 233 measurements resulting from sensor data 256a generated by sensors 252 attached to or associated with the reference golf club 250, such as sensors 152a-152e, the swing parameter 233 results are compared to and calibrated based on the swing parameter 233 results from sensor data 256a generated by sensors 252 disassociated from the reference golf club 250, such as sensor 152f of FIG. 1. In order to do this, each of a plurality of swings of the reference golf club 250, and preferably a plurality of swings of golfers of varying skill levels, are each recorded simultaneously by at least one sensor 252 similar to those of sensors 152a-152e and at least one sensor similar to that of sensor 152f of FIG. 1. As a result of the sensor data 256a from sensor 152f being more accurate than the sensor data 256a from the sensors 152a-152e, an algorithm, such as the algorithm 263, lie algorithm 243, and/or the shaft algorithm 238, can manipulate the sensor data 256a from the sensors 152a-152e to more accurately reflect the sensor data 256a from the sensor 152f. To do this, the relationship between the sensor data 256b generated by the sensors 152a-152e and the sensor data 256b generated by the sensor 152f is determined, using a regression model, for example.

For some data of the sensor data 256b there may a consistent difference between an individual data of the sensor data 256b, such as 3-D location data, and thus a conversion factor can be applied to the sensor data 256b generated from the sensors 152a-152e such that the sensor data 256b more accurately reflects the sensor data 256b from the sensors 152f. In such a case, the algorithm 263, the lie algorithm 243, and/or the shaft algorithm 238 convert the sensor data 256b from the sensors 152a-152e upon receiving the sensor data 256a.

For other data of the sensor data 256b, the difference may not be apparent until the sensor data 256b from the sensors 152a-152e and from the sensor 152f have been utilized in determining the swing parameters 233. For this data, the swing parameter 233 calculations are calibrated such that the calculated swing parameters 233 from the sensors 152a-152e more accurately reflect the calculated swing parameters 233 from the sensor 152f. For example, the attack angle of the reference golf club 250 may be consistently greater based on the sensor data 256b generated by the sensors 152a-152e than the attack angle based on the sensor data 256b generated by the sensor 152f. In such an example, the sensor data 256b alone for each of the data of the sensor data 256b that is utilized in calculating the swing parameters 233 may not have shown any consistent differences or patterns that could be easily convertible. However, once the swing parameters 233 are calculated from both the sensor data 256b from the sensors 152a-152e and the sensor data 256b from the sensor 152f, a more consistent difference or pattern may arise. In such cases, the swing parameters 233 may have conversion factors applied so that the swing parameters 233 generated from the sensors 152a-152e more accurately reflect the swing parameters 233 generated from the sensors 152f. This may be accomplished using a regression model, such as simple linear regression, or a regression model more like the regression model described below with respect to the lie algorithm 243.

It should be noted that for some sensor data 256a and for some swing parameters 233, the sensors 152a-152e may be more accurate. Because the sensors 152a-152e are attached to or integral with the reference golf club 150, measurements that reflect the rotation or path of the reference club head 150 are often more accurate. As such, examples of this sensor data 256a and swing parameters 233 may be the rotation and path measurements, such as release, distance to impact, and swing path measurements including comparisons between length aspects of the swing path, swing path width, and swing path area. For this sensor data 256a and swing parameters 233, the sensor data 256b and the swing parameters 233 generated by the sensors 152f may be converted to more accurately reflect the sensor data 256b and the swing parameters 233 generated by the sensors 152a-152e. However, if the only sensors 152 being used are the sensors 152a-152e, no conversion need be done for this sensor data 256a and swing parameters 233.

By comparing the sensor data 256b and the swing parameters 233 generated by the sensors 152a-152e and the sensor 152f, a more efficient, transportable, and accurate fitting experience is created. Sensors similar to those of sensor 152f are heavier, larger, more cumbersome, detached from the reference golf club 150, and often require a wired connection. Sensors 152a-152e, on the other hand, are smaller, attached to or integral to the reference golf club 150, don't require a wired connection, and are very lightweight. Historically, the drawback of sensors 152a-152e is their accuracy. As mentioned above, for many measurements sensors like sensor 152f are more accurate. As such, by using an algorithm to convert the sensor data 256b and the swing parameters 233 from the sensors 152a-152e to more accurately reflect that of the sensor 152f, much of the loss in accuracy can be accounted for. As a result, the sensor data 256b and the swing parameters 233 generated from the sensors 152a-152e provide accurate information in a more compact, portable, and easily configurable package as a result of utilizing algorithms to calibrate the sensor data 256b and the swing parameters 233.

It should be noted that the terms "sensors 152a-152e," as used herein, may refer to one or more than one of the sensors 152a-152e, and that the term "sensor 152f" may refer to one or more than one of the sensors 152f.

Referring back to FIG. 2A, the data 224 further includes additional data 234. The additional data 234 may include data relating to the location of the computing device 210 and/or the sensor 252. The location may be determined utilizing a Global Positioning System (GPS) or another suitable location device. The additional data 234 may further include weather information pertaining to the location, including climate conditions, which may factor into the sensor data 256b, the sensor settings 258b, and/or the swing parameters 233. The additional data 234 may be factored in to the swing parameters 233, to account for atmospheric pressure, turf conditions, moisture, and other information that may be utilized manually, or dynamically, to update the sensor settings 258a/258b, in order to more accurately record the sensor data 256a/256b, or to provide more data to the recommendation engine.

The data 224 includes the user data 235. The user data 235 may include the location, age, gender, race, nationality, height, weight, arm length, torso length, body type, wrist to ground length, and other user data 235 relating to the user 202 of the reference golf club 250. The user data 235 may further include preferences of the user 202, such as the desired or undesired golf club types. The user data 235 may include historical data of the user 202 such as the golf clubs currently or previously used by the user 202, the handicap of the user 202, and/or the frequency and location of play of the user 202. Such data may also include previously measured, calculated, and/or outputted information provided to a user using the same or a similar analysis process or apparatus. In some implementations, the reference golf club 250 may be customized by the user 202, or may have different characteristics than those included in the sensor settings 258b. In such an implementation, the user data 235 may further include customization information of the user 202, such as adjusted characteristics of the reference golf club 250, including length, loft, and lie characteristics. The user data 235 may be utilized manually, or dynamically, to update the sensor settings 258a/258b, in order to more accurately record the sensor data 256a/256b, or to provide more data to the recommendation engine.

The software application 220b also includes the algorithm 236. The algorithm is configured to receive input values, which may include at least one of the swing parameters 233, and to output the skill value 237. The algorithm 236 may be generated in a plurality of different ways, and may include any number of the swing parameters 233 as part of its formula. It should be noted that the algorithm 236 may include multiple different algorithms. For example, separate algorithms may be utilized for outputting the skill value 237 utilized by the recommendation engine 225 for generating a club head recommendation, a ball recommendation, or a shaft recommendation. However, in some implementations, a single algorithm may output the single skill value 237 that is utilized in making a recommendation of club head, ball, and shaft.

As an example, in one implementation, the algorithm 236 may only include one or more of the swing parameters 233 which are used to determine the skill value 237. In such an implementation, the swing parameters 233 may be normalized so as to output the skill value 237 such that the skill value 237 matches one of the golf club skill values 227.

As another example, in some implementations, in order to determine which of the swing parameters 233 to utilize in generating the algorithm 236, a least squares regression analysis may be performed. First, a plurality of users having varying known handicaps and known skill levels can take swings with the reference golf club 250. For each swing, each of the swing parameters 233 can be calculated based on the sensor data 256b. The resulting combinations of known skill level and parameter value are plotted. For each swing parameter 233, a linear regression analysis is performed by generating a best-fit straight line through the set of data points, i.e., in such a way as to make the sum of squared residuals ($r^2$), or, in other words, the vertical distances between the data points and the straight line, as small as possible. As a result of the simple linear regression, an $r^2$ value is determined for each of the swing parameters 233 and compared. The larger the $r^2$ value of the swing parameters 233, the less deviation the data points have from the straight line, and thus the more consistent and telling the swing parameters 233 are believed to be of skill level.

Based on the above process, it was believed that one or more swing parameters, either alone or in combination with each other, may serve as acceptable candidates for predicting a skill level for a golfer using a swing analysis device or process. In addition to considering $r^2$ values, other factors were believed to be relevant to this determination. For example, the nature and extent of outliers were considered as were the nature of an erroneous recommendation. For example, consideration was afforded to understanding the reasoning behind an erroneous recommendation, the constitution of erroneous recommendations and any psychological effect that such erroneous recommendation may have on a potential user. Ultimately, based on at least some of the above factors, it was determined that a comparison between an aspect of the backswing to a corresponding aspect of the downswing of a recorded swing path stood out as a preferable means for predicting golfer skill level. More specifically, the comparison includes a length ratio being a ratio between the length of the backswing segment of the swing path and the length of the downswing segment of the swing path. In some such embodiments, optionally, such lengths are determined as lengths measured of the projection of the swing path in a virtual plane. In some embodiments, a determination of skill level is based at least in part on maximum velocity (as defined above), which also had been considered to have a high $r^2$ value. In some such embodiments, maximum velocity is solely used to calculate skill level. Although the length ratio and the maximum velocity were determined to be preferable, it should be noted that any of the swing parameters 233 may be used in generating the algorithm 236.

Once the swing parameters 233 for use in the algorithm 236 are determined, they may be normalized such that when the swing parameters 233 are input into the algorithm 236, the skill value 237 output by the algorithm always falls within the range of one of the of the golf club skill values 227 within the database 226 of the recommendation engine 225 such that a golf club, a shaft, and/or a golf ball can be recommended. The swing parameters 233 may be normalized based on generic values, such as normalizing to 1, or may be normalized based on the results of testing. In an implementation where testing is conducted, a maximum average value may be used to normalize the swing parameters 233.

For example, if the swing parameter being tested is the maximum velocity, and one hundred users take swings with the reference golf club 250, the ten highest maximum velocities may be averaged, and yield a number such as 115 mph. As such, the swing parameter of maximum velocity may be normalized to 115 mph, such that the values for the maximum velocity are input into the algorithm 236 as a percentage of 115 mph. In such an implementation, if the user 202 has a maximum velocity of 115 mph, the value 1 would be input into the algorithm 236. If the user 202 has a maximum velocity of 57.5 mph, the value 0.5 would be the input into the algorithm 236, and so on.

For another example, if the swing parameter being tested is the length ratio, where the length ratio in this example is the 3D distance a location on the club head of the reference golf club travels during the backswing compared to the 3D distance the location travels during the downswing, then after the one hundred users take swings with the reference golf club 250, the ten highest length ratios may average to 1.5, meaning the backswing length is 1.5 times longer than the downswing length. In such an example, the length ratio may be normalized to 1.5.

In other examples, various curve-fitting operations are developed to associate quantitative swing data with skill level. For example, normalization may be associated with a skill level value by curve-fitting to a Gaussian distribution or other distribution. However, in some cases, particularly where the boundaries between skill levels cannot be accurately drawn from a single swing parameter, relationships may be developed for controlling how multiple swing parameters may interplay to correspond with a recommended skill level. In such cases, values may be determined, e.g., empirically, by which to add, subtract, multiply, and/or divide the swing parameters 233 values by, such that when the swing parameters 233 are used in the algorithm 236, the skill values 237 output fall within a certain range that matches up with the range of values of the golf club skill values 227 in the database 226. The values by which to add, subtract, multiply, and/or divide may come from testing, such as that discussed above, or may be based on analysis of different values and their effect on the algorithm 236 outputs. The software application 220b may utilize values from the swings of a plurality of users of the reference golf club 250 to determine equations that output results, e.g., skill values 237, within a specific range, or at least where a specified percentage of input values would output results within a specific range. In some embodiments, curve-fitting modules are stored such that the processor may automatically develop swing parameter to skill level relationships based on input swing information from a group of users. In some cases, relationships are develop in such a manner and adaptable based on new input. For example, information regarding a club that a user actually purchased in combination with some information regarding his or her swing may be stored and used to either verify the integrity of the recommendation engine and/or to automatically adjust how the recommendation engine correlates swing data with skill level. In some cases, the recommendation engine determines a skill level value based on swing data, whereby the determination is based entirely on feedback information regarding correspondences between swing data and actually purchased golf clubs. In this manner, the processor may be adapted to continuously run e.g., perform $r^2$ best-fit analysis based on a continually updating stream of data, and continuously adjust its skill level recommendation module based on such $r^2$ best-fit analysis.

For one example of algorithm 236, the swing parameters 233 used were the length ratio and the maximum velocity, where the length ratio in this example was the 3D distance a location on the club head of the reference golf club travels during the backswing compared to the 3D distance the location travels during the downswing. The skill values 237 desired were in the range of 2-9. During testing, a predetermined set of the highest maximum velocities recorded averaged to about 115 mph, and from this number, with the goal of normalizing maximum velocity to be useful in predicting skill values 237 in the range of 2-9, the following equation (1) was determined:

$$\text{Max Velocity Final} = (\text{Maximum Velocity} - 70 \text{ mph})/5 \text{ mph} \quad (1);$$

If the Max Velocity Final was greater than 9, or less than 2, the Max Velocity Final was rounded to 9 or 2, respectively. Also during testing, the highest length ratios recorded averaged to about 1.5, and from this number, with the goal of normalizing the length ratio to be useful in predicting skill values 237 in the range of 2-9, the following equation (2) was determined:

$$\text{Length Ratio Final} = (\text{Length Ratio} - 1.05) \times 20 \quad (2);$$

If the Length Ratio Final was greater than 9, or less than 2, the Length Ratio Final was rounded to 9 or 2, respectively. After calculating Max Velocity Final and Length Ratio Final, the following equation (3) was utilized to calculate the skill value 237:

$$\text{Skill Value} = (\text{Max Velocity Final} + \text{Length Ratio Final})/2 \quad (3);$$

As such, the skill value 237 output by the algorithm falls within a range of 2-9, which was designed to match the golf club skill values 227 assigned to the golf clubs 228, shafts 231, and the balls 233 in the database 226.

The software application 220b further includes the recommendation engine 225. The recommendation engine 225 is configured to utilize the data 224 and/or the skill value 237 to determine recommended golf clubs 228, shafts 231, and/or balls 233. Once the recommendation engine 225 has determined the recommended golf clubs 228, shafts 231, and/or balls 233, the recommendation engine can send the information pertaining to the recommendations to the display 238 for visualization and interaction by a user of the computing device 210.

It should be noted that the recommendation engine 225 is illustrated with dashed lines to indicate that the recommendation engine 225, or certain components thereof, may not be stored on the device memory 214, but may be stored externally, such as on the server 270. For example, in implementations where the database 226 includes a large quantity of golf clubs 228, shafts 231, and balls 233, it may be desirable to store that information externally to the computing device 210 based on data storage capacity requirements of the computing device 210.

The recommendation engine 225 includes the database 226. The database 226 is configured to store the golf club skill values 227 and information regarding the identification and aspects of the golf clubs 228, the shafts 231, and the balls 233. The recommendation engine 225 is updated dynamically as new products are introduced, old products are phased out, and current products become sold out or otherwise unavailable. For example, if the recommendation engine 225 recommends golf club A from the golf clubs 228 having a 10.5 degree loft, but determines that the 10.5 degree loft is sold out, the recommendation engine 225 will recommend another loft. In addition, as new data is collected using the sensor 252, and other sensors in communication with the network 290, the golf club skill values 227 may be updated for each of the golf clubs 228, the shafts 231, and the balls 233.

The database 226 includes the golf club skill values 227. The golf club skill values 227 are values that are assigned to each of the golf clubs 228, the shafts 231, and the balls 233. The golf club skill values 227 assigned to each of the golf clubs 228, the shafts 231, and the balls 233 may be a single value, or a range of values. For example, golf club A of the golf clubs 228 may include a golf club skill value of 5, such that when the skill value 237 is 5, golf club A is recommended. In another example, golf club A may include the golf club skill values 227 ranging from 4.7 to 5.3, such that when the skill value 237 is 5, golf club A is recommended.

The golf club skill values 227 are not intended to be limited to the golf clubs 228, and may also apply to the shafts 231 and the balls 233. For example, the balls 233 and the shafts 231 may also have associated golf club skill values 227 based on the golf club skill values 227 of the golf clubs 228 described above. In such an example, the shafts 231 and the balls 233 may be assigned the golf club skill values 227 corresponding to the golf club skill values 227 assigned to the golf clubs 228 that match the skill values 237 based on the algorithm 236. In this manner, golf ball and/or shaft recommendations may be determined and outputted/displayed using the same skill level generating module that is used for golf club head recommendation.

However, in other implementations, separate algorithms may be used for determining skill values for the balls 233 and the shafts 231. In such an implementation, the algorithm for the balls 233 may calculate a ball skill value and the algorithm for the shafts 231 may calculate a shaft skill value. The algorithms for calculating the ball and shaft skill values may utilize the swing parameters 233 and the sensor data 256*b*. For example, the ball skill value may be based on the impact conditions as measured by the sensor 252, where the sensor 252 may be a ball sensor similar to that of ball sensor 104 in FIG. 1. As another example, a ball skill level recommendation may be made by parameters detected from sensor 152*a*. However, in some embodiments, such parameters either: (a) differ in one or more respects from those parameters used in generating a club head skill level; (b) are the same parameters used in generating a club head level but differently weighted or otherwise considered in generating a skill level value; or (c) some combination of (a) and (b). For example, it may be contemplated that certain swing attributes are more critically determinative of skill level for balls than for club head. For example, for golf balls, it may be considered that velocity at impact should carry greater weight in ball selection than length ratio, and thus, velocity at impact may also carry greater weight for generating golf ball skill value.

The golf clubs 228 may include models 229 and properties 230. In addition to the golf clubs 228 having corresponding golf club skill values 227, the individual models 229 of the golf clubs 228 may also have corresponding skill values. For example, the golf clubs 228 may include a family of drivers, and each member of the family of drivers may correspond to one of the models 229. As such, each of the models 229 may include its own golf club skill values 227.

In addition, the golf clubs 228, including the models 229, include the properties 230. The properties 230 include the loft, lie, club face angles, and other properties of the golf clubs 228. The loft, lie, club face angle, weight insert mass(es), and other properties of the golf clubs 228 may be recommended utilizing the golf club skill values 227, or may be recommended based on other data 224. For example, once one of the golf club 228 having one of the models 229 has been recommended by the recommendation engine 225, the recommendation engine 225 may utilize the swing parameters 233, the sensor data 256, and/or other data 224 to determine the properties 230 of the golf club 228. In such an example, the recommendation engine 225 may recommend model A from the models 229 based on the golf club skill values 227. After recommending model A, the recommendation engine 225 may utilize the angle of attack and velocity information at impact from the data 224 to determine that a prescribed loft, e.g., a 10.5 degree loft, is recommended.

As used herein, the term "attack angle" is defined as an angle at which a geometric center of a face of a club head is moving at a point of impact with a golf ball or virtual golf ball measured with respect to, and in a plane perpendicular to, the ground plane. The positive angle of attack is when the club head strikes the ball moving upwards, and negative is when the club head is moving downwards when striking the ball.

As used herein, the term "impact loft" of a club face of a reference golf club 250 denotes an angle measured at impact between a virtual ground plane and a line extending normal to the face of the club head of the reference golf club 250 at the geometric center of the face and projected onto a virtual vertical plane perpendicular to the general striking face plane considered when the club head is oriented in an initial address position.

An actual loft recommendation may be determined utilizing the attack angle, impact loft, and velocity data of the club head of the reference golf club 250 generated by the sensor data 256*b*. In some embodiments, the recommendation engine 225 may utilize a plurality of attack angle data points and maximum velocity data points to determine an ideal impact loft of the club head for each possible combination of attack angle and maximum velocity. In addition, impact loft may be compared to the actual designated club head loft value from the sensor settings 258*b* to determine a delta loft.

The delta loft is the difference between the designated club head loft value as optionally stored in sensor settings 256*b* and the impact loft. The delta loft is then subtracted from the ideal impact loft generated by the recommendation engine 225 for the measured attack angle and velocity of the swing of the reference golf club 250 to output a recommended actual loft. The recommendation engine 225 then utilizes the static loft value to find golf clubs 228 from the database 226 having designated lofts closest to the static loft.

For example, assume the recommendation engine 225 determines, based on the skill value 237, that golf club A is the recommended golf club for user 202. The recommendation engine 225 may then utilize the recommended actual loft output, which may be 9.7, in this example, to determine the proper loft designation of golf club A to recommend to the user 202. If golf club A is offered in designated lofts of 8.5, 9.5, and 10.5, based on the properties 230 in the database 226, the recommendation engine 225 would recommend a loft of 9.5 which is closest to the static loft 9.7 output by the loft determination done by the software application 220b.

Although the above example describes the recommendation engine 225 determining the recommended actual loft independent of the recommended golf club for the user 202, this example is not intended to be limiting. In another example, the recommendation engine 225 may recommend golf club A to the user 202 based on the skill value 237, for example, and then utilize a plurality of attack angles and velocities to determine the ideal impact loft of golf club A for each possible combination of attack angle and velocity, utilizing the properties 230 of golf club A, specifically. At this point, the remaining steps of the process for determining the loft recommendation would continue as discussed above.

The recommendation engine 225 may utilize the swing parameters 233 directly to recommend the golf clubs 228, the shafts 231, and the balls 233. For example, the database 226 may include recommended values for the swing parameters 233 for each of the golf clubs 228, the shafts 231, and the balls 233. As a result, when the recommendation engine 225 receives the swing parameters 233 after a swing of the reference golf club 250 by the user 202, the recommendation engine 225 can recommend any number of the golf clubs 228, the shafts 231, and the balls 233, including models 229 and properties 230 of the golf clubs 228, and properties 232 of the shafts 231.

The recommendation engine 225 may utilize the additional data 234 to determine recommended golf clubs 228, shafts 231, and balls 233. For example, if the additional data 234 includes location data, the recommendation engine 225 may only recommend the golf clubs 228, the shafts 231, and the balls 233 that are available in that location. As such, if the user 202 lives in the United States, for example, the recommendation engine 225 will only recommend items from the database 226 that are available in the United States. As another example, if the additional data 234 includes turf conditions, the recommendation engine 225 may only recommend balls 233 that perform well on those turf conditions. Such determination of turf conditions may be a function of geographic location to be determined using GPS or other transmitted location data.

The recommendation engine 225 may utilize the user data 235 to determine recommended golf clubs 228, shafts 231, and balls 233. For example, if the user data 235 includes the height and gender of the user 202, the recommendation engine 235 may only recommend the golf clubs 228, the shafts 231, and the balls 233 recommended for a user of that gender and height. For another example, if the user 202 specifies that they prefer golf clubs with draw or fade correction or golf clubs with no weight inserts, the recommendation engine 225 may only recommend the golf clubs 228 capable of draw and fade correction and/or no weight inserts.

The database 226 further includes the shafts 231 including the properties 232. The shafts 231 may include any number of different shafts, and each of the shafts 231 may be designed for a certain club type, or may be designed for multiple club types. The properties 232 of the shafts 231 include the flex, the flex profile, the length, the materials, adjustability characteristics, and other properties necessary for the recommendation engine 225 to recommend the shafts 231, as will be described in greater detail below with respect to FIG. 2C. The flex includes, for example, X (extra stiff), S (stiff), R (regular), A (amateur) and W (women's). The flex profile may alternatively, or in addition, include flex profiles based on other conventional flex profile coding system, e.g., a conventional profile coding system that represents shaft stiffness at plural locations about the length of the shaft. For example, shaft recommendations may include the shaft profiling convention described in U.S. Pat. No. 8,337,336 (incorporated by reference herein in its entirety), particularly the convention described at page 3, line 20 to page 5, line 48. One example of a correlation between swing parameters 233 and recommended shaft properties 232 includes if the user 202 has a high maximum velocity value as one of the swing parameters 233, the recommendation engine 225 may recommend one of the shafts 231 having a stiffer flex, such as S or X flex. In addition, the recommendation engine 225 may take into account other of the swing parameters 233, or skill values 237, to determine a proper flex profile for the shaft of the user 202, such as a flex profile of "7457" (with regard, e.g., to the shaft selection convention described at page 3, line 20 to page 5, line 48 of U.S. Pat. No. 8,337,336 described above), where the butt end and the tip end have more stiffness than the central sections of the shaft.

The recommendation engine 225 may also utilize the sensor data 256b, calculated utilizing the sensor settings 258b which include the flex profile of the reference golf club 250, to determine the deflection of the shaft of the reference golf club 250 during the swing by the user 202. The deflection information can then also become a factor in recommending one of the shafts 231 having properties 232 suitable for the user 202. For example, if the deflection of the shaft is beyond a certain threshold value, the recommendation engine 225 may recommend one of the shafts 231 having a stiffer flex profile. On the other hand, if there is a small amount of deflection in the shaft of the reference golf club 250 during the swing the user 202, the recommendation engine 225 may recommend one of the shafts 231 having a less stiff flex profile, such as a shaft having the flex profile "3242" (with regard, e.g., to the shaft selection convention described at page 3, line 20 to page 5, line 48 of U.S. Pat. No. 8,337,336 described above), for example.

The database 226 further includes the balls 233. In some implementations, the balls 233 may include the golf club skill values 227 and be recommended based on the match to the skill value 237 e.g., as described above. In some implementations, the balls 233 may be recommended based off of the sensor data 256b, including calculated ball spin, ball flight path, and ball flight distance based on the impact conditions of the club head of the reference golf club 250, for example. As an example, if the ball spin is calculated to have a high side spin, the recommendation engine 250 may recommend one of the balls 233 designed for reduced spin. In addition, any number of the swing parameters 233 may be utilized in recommending the balls 233. For example, if the user 202 has a high maximum velocity during the swing, the recommendation engine 225 may recommend one of the balls 233 designed for high swing speeds.

Figure 2B:
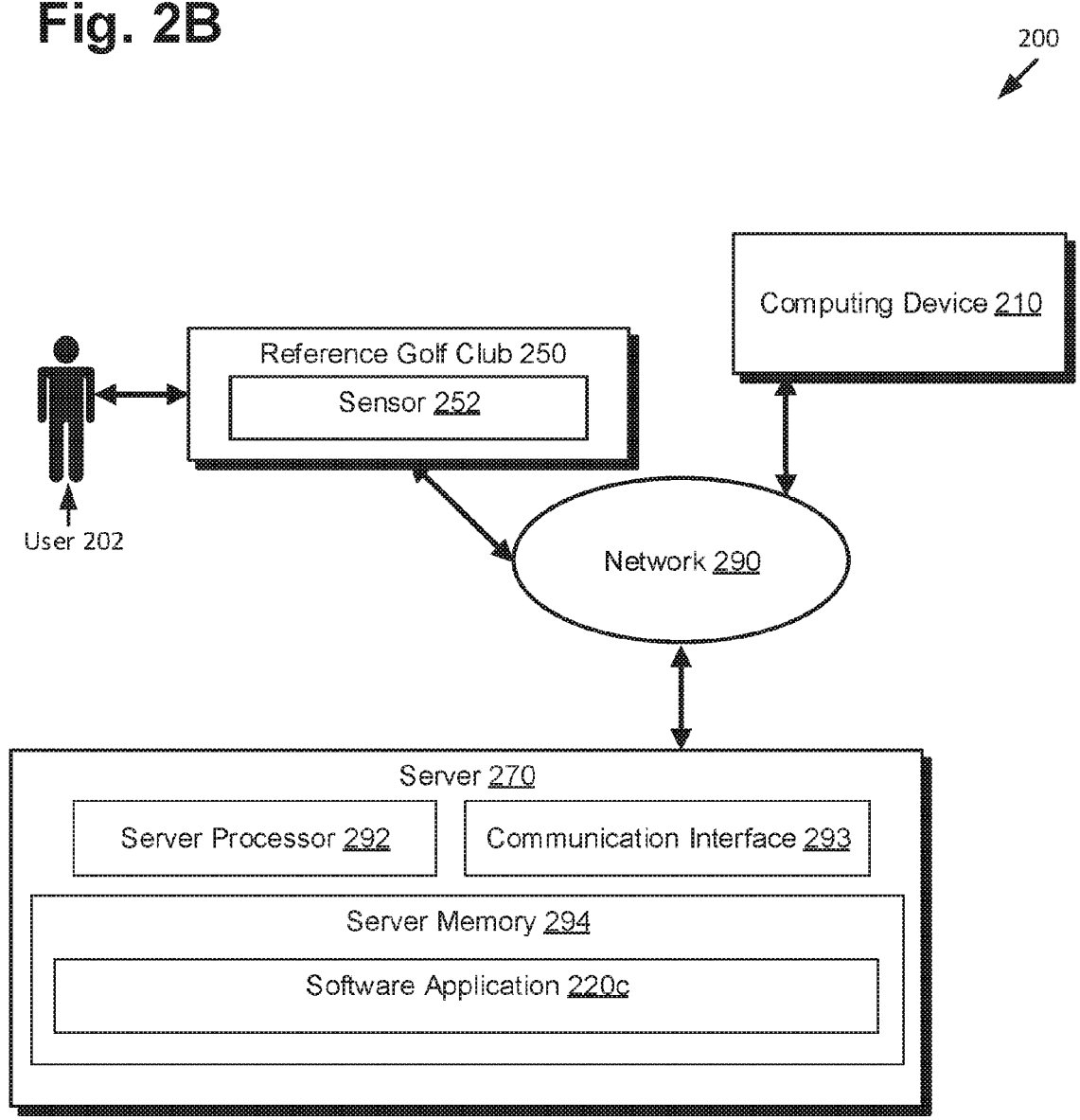
FIG. 2B is another illustration of the system of FIG. 2A for analyzing a sporting apparatus, according to one implementation of the present disclosure.

Now referring to FIG. 2B, FIG. 2B is another illustration of the system of FIG. 2A for analyzing a sporting apparatus, according to one implementation of the present disclosure. The system 200 of FIG. 2B includes the user 202, the reference golf club 250 including the sensor 252, the network 290, the computing device 210, and the server 270. The server 270 includes server processor 292, communication interface 293, and server memory 294. The server memory 294 includes the software application 220c. It should be noted that the user 202, the reference golf club 250, the sensor 252, the computing device 210, the network 290, the server 270, and the software application 220c of FIG. 2B correspond respectively to the user 202, the reference golf club 250, the sensor 252, the computing device 210, the network 290, the server 270, and the software application 220*b* of FIG. 2A.

The server 270 includes the server memory 294 and the server processor 292. The server processor 292 is configured to execute computer-readable instructions that are stored in the server memory 294. The instructions may be, for instance, instructions for receiving, transmitting, or analyzing data from the sensor 252 and/or the computing device 210. The server processor 292 may access the server memory 294 by way of a system bus, for example. Various functions of the server memory 294 may be implemented similarly to that of the device memory 214 described above.

The server 270 also includes a communication interface 293 configured to allow external devices, such as the computing device 210 and the sensor 252, to communicate with the server 270 and also allow the server 270 to communicate with the external devices over the network 290. For example, in some implementations, the server 270 may receive data and or instructions for execution by the server processor 292 from an external device.

The server memory 294 includes the software application 220*c*. The software application 220*c* may include some or all of the features of the software application 220*b* stored on the computing device 210. For example, in some implementations, the server 270 may only store the recommendation engine 225 on the server memory 294 and receive the data 224 and the algorithm 236 from the computing device 210. In such an example, the server 270 may determine the recommended golf clubs, shafts, and balls and transmit that data back to the computing device 210 using the network 290. However, in other implementations, the server 270 may store all of the data 224, the recommendation engine 225, and the algorithm 236 such that the server 270 can perform calculations independently of the computing device 210. In such an implementation, the server 270 may use the data 224, the algorithm 236, and the recommendation engine 225 to determine recommended clubs, shafts, and balls and transmit the information to the computing device 210, thereby freeing up processing and storage capabilities for the computing device 210.

Figure 2C:
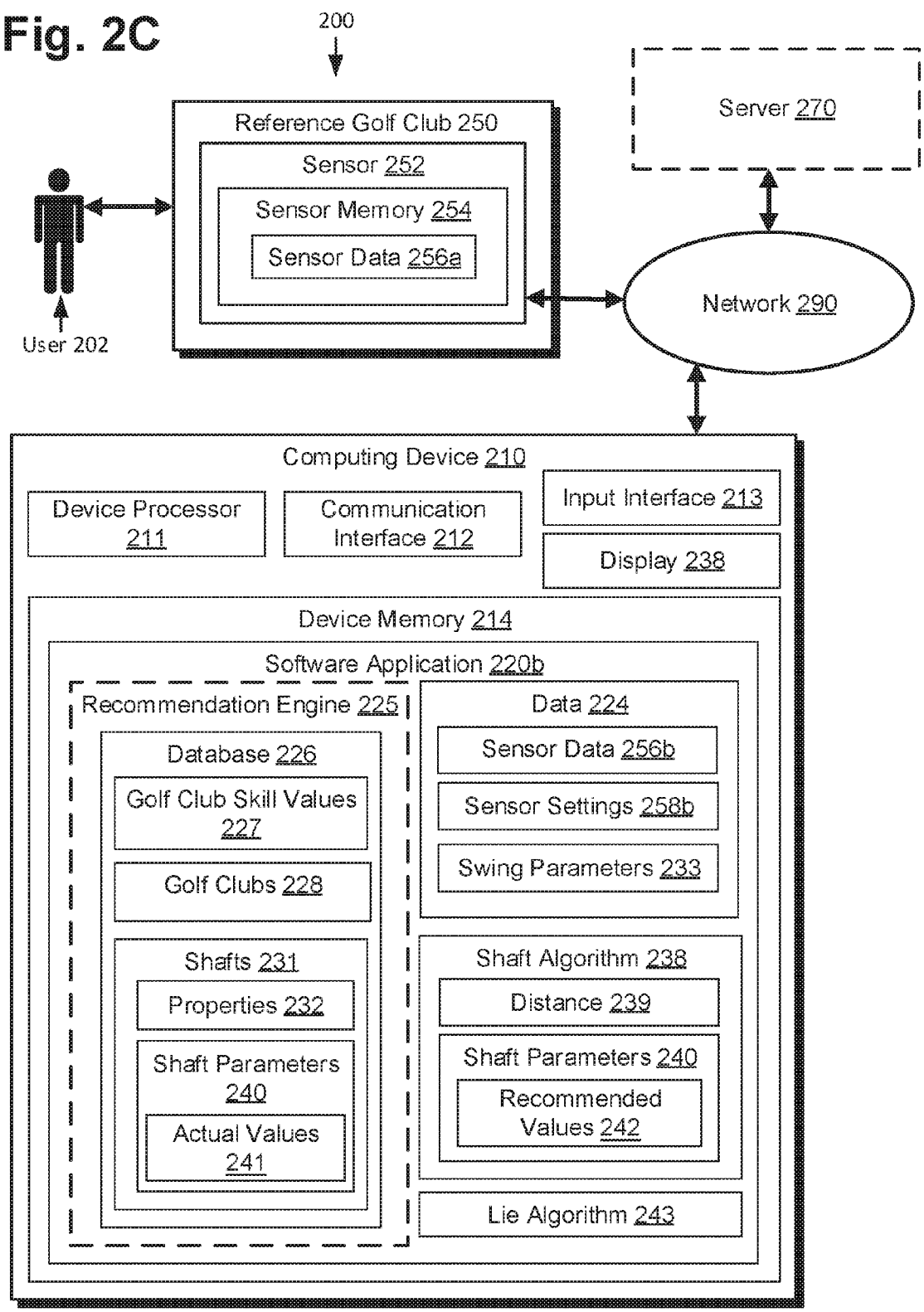
FIG. 2C is another illustration of the systems of FIG. 2A and FIG. 2B for analyzing a sporting apparatus, according to one implementation of the present disclosure.

It should be noted that although only one server 270 is illustrated in FIGS. 2A, 2B and 2C, any number of servers 270 may be implemented. For example, each of the servers 270 may be operated by a different manufacturer, such that each server 270 utilizes a recommendation engine 225 to recommend golf clubs 228, shafts 231, and balls 233 from each respective manufacturer. In such an implementation, the computing device 210 can display a number of different recommended golf clubs, shafts, and balls from a variety of different manufacturers. In addition to each recommendation engine 225 on each server 270 filtering through the database 226 to determine recommendations, an additional recommendation engine 225 on the computing device 210 may filter through the results from each of the manufacturers to output the golf clubs 228, shafts 231, and balls 233 from manufacturers that the user 202 prefers based on the user data 235, for example. Additionally, multiple manufacturers may share servers, or one server 270 may be operated for all manufacturers together.

Now referring to FIG. 2C, FIG. 2C is another illustration of the systems of FIG. 2A and FIG. 2B for analyzing a sporting apparatus, according to one implementation of the present disclosure. The system 200 of FIG. 2C includes the user 202, the reference golf club 250 including the sensor 252, the network 290, the computing device 210, and the server 270. The server 270 includes server processor 292, communication interface 293, and server memory 294. The server memory 294 includes the software application 220*c*. It should be noted that the user 202, the reference golf club 250, the sensor 252, the computing device 210, the network 290, the server 270, and the software application 220*c* of FIG. 2C correspond respectively to the user 202, the reference golf club 250, the sensor 252, the computing device 210, the network 290, the server 270, and the software application 220*b* of FIG. 2A and FIG. 2B.

FIG. 2C includes the software application 220*b* which includes the recommendation engine 225 that includes the database 226. The database 226 includes shafts 231, and the shafts 231 include properties 232 and shaft parameters 240. The shafts 231 may include all of the shafts available in the marketplace, and also shafts that are not included in the marketplace such as prototype shafts. However, the software application 220*b* may only store the shafts that are currently available, or only the shafts that are currently on the market, or only prototype shafts, or only the shafts that the particular fitter wishes to factor into the recommendation engine 225.

Each of the shafts 231 has properties 232. The properties 232 may include the shaft weight, the shaft frequency, the shaft kick point, the shaft flex, the shaft length, the shaft materials, the shaft IFC code, the shaft tip flex, the shaft butt flex, the balance point of the shaft, the swing weight, the shaft torque, or other properties 232 pertaining to the shafts 231. The shaft parameters 240 are the selected properties 232 from all the properties 232 that are recorded for each of the shafts 231. As such, even though each of the shafts 231 may have any number of properties 232, the database 226 may only store the properties 232 determined to be most useful in the shaft recommendation and fitting process as the shaft parameters 240. Below are listed a plurality of properties 232, their definitions, and their effect on feel and performance. Each of the properties 232 effect on feel and performance may be used to determine which of the properties 232 to use as shaft parameters 240 in the shaft algorithm 238 for recommending shafts 231 to the user 202.

As used herein, the "shaft weight" is defined as the measured weight of the shaft. The shaft weight can be measured using any method known to those skilled in the art, including weighing the shaft on a scale. The shaft weight is one of the properties 232 that is indicative of the feel of the shaft, and ultimately the entire golf club. The club weight includes the weight of the grip, the shaft, and the club head, where the shaft may account for a large percentage of the overall club weight. As such, finding a shaft having a shaft weight that provides a desired feel for the overall golf club is important in recommending at least one of the shafts 231 to the user 202. In addition, because the shaft weight factors into the club weight and is generally a result of other properties 232 of the shafts 231, such as the materials, swing weight, etc., the shaft weight also factors into the performance of the shaft 231 for the user 202. For example, for a golfer with a slow swing speed, generally indicating less power and body torque generation, a shaft 231 having a low shaft weight may be desired because a high shaft weight adds to the overall club weight and thus may slow down the swing speed more than necessary, thereby limiting the performance of the shaft for that user 202. For such a golfer, a lighter shaft weight with more tip flex, for example, may enable the generation of more club head speed and thus a higher ball speed at impact. On the other hand, a golfer with a very high swing speed, generally indicating more power and body torque generation, may prefer a shaft 231 having a high shaft weight because the increased shaft weight may allow for better feel through the swing and also for better launch conditions at impact.

As used herein, the "shaft frequency" is defined as the natural frequency of the shaft when clamped on the butt end. The shaft frequency is generally measured in cycles per second. The shaft frequency is measured by placing the shaft into a shaft frequency measurement device, such as the DigiFlex™ Frequency Meter, and twanging the shaft (i.e., gripping the shaft between your fingers at the tip end, lifting the tip end of the shaft upwards, and then releasing the tip end of the shaft). The shaft frequency measurement device then measures the shaft frequency. The shaft frequency is another property 232 that is indicative of both performance and feel. For example, a shaft 231 having a higher shaft frequency is stiffer than a shaft with lower shaft frequency. The stiffness of a shaft can be felt by a golfer swinging a golf club, but the stiffness of the shaft is also important to the performance of the shaft 231 given the particular users 202 swing attributes. For example, a player with a high swing speed typically would prefer, and get the best performance from, a shaft 231 having a higher shaft frequency, i.e., a stiffer shaft. This is because, if a shaft 231 is not stiff enough for a high swing speed golfer (e.g., swing speeds greater than 90 mph), the shaft may deflect more than desired thereby decreasing the performance of that shaft 231 for that user 202. The opposite can be said for a user with a slow swing speed, where the lower the shaft frequency (i.e., the less stiff the shaft), can provide more deflection than the user 202 would be able to generate with a stiffer shaft, thus increasing loft at impact by a "whipping" effect. In addition, low frequency shafts are generally lighter weight than higher frequency shafts, thus allowing for an increase in head speed and ultimately ball speed.

As used herein, the "shaft tip flex" is defined as the amount of deflection of the tip of the shaft when under a load stress. The amount of deflection is the difference in vertical height between two points.

In one testing implementation, the first point is with zero deflection, measured horizontally, along the shaft axis, 27.5" from the butt end of the clamp toward the butt end of the shaft, under no load stress. The second point is after the load stress is applied, measured horizontally, along the shaft axis, 27.5" from the butt end of the clamp toward the butt end of the shaft. For example, the tip end of the shaft may be clamped with a 2" clamp approximately 0.5 inches from the tip end. The clamp having a clamp pressure of 80 Psi. A 2,700 g weight is then applied 24" from the butt end of the clamp toward the butt end of the shaft.

The shaft tip flex is another of the properties 232 that relate to both feel and performance. The shaft tip flex relates to the overall flex of the club, so similar to that described above with shaft flex profile, the shaft tip flex can give an indication of the feel of the shaft, for example, whether it is stiff or has some wiggle to it. However, shaft tip flex alone is not an ideal indicator of feel and performance, because it does not give an idea of the overall flex, feel, and performance of the shaft, but rather just the flex of the tip of the shaft.

As used herein, the "shaft butt flex" is defined as the amount of deflection of the butt of the shaft when under a load stress. The amount of deflection is the difference in vertical height between two points.

In one testing implementation, the first point is with zero deflection, measured horizontally, along the shaft axis, 33.5" from the tip end of the clamp toward the tip end of the shaft, under no load stress. The second point is after the load stress is applied, measured horizontally, along the shaft axis, 33.5" from the tip end of the clamp toward the tip end of the shaft. For example, the butt end of the shaft may be clamped with a 3" clamp approximately 5 inches from the butt end. The clamp having a clamp pressure of 80 Psi. A 2,700 g weight is then applied 30" from the tip end of the clamp toward the tip end of the shaft.

The shaft butt flex is another of the properties 232 that relate to both feel and performance. The shaft butt flex relates to the overall flex of the club, similar to that described above with shaft flex profile, the shaft butt flex can give an indication of the feel of the shaft, for example, whether it is stiff or has some wiggle to it. However, shaft butt flex alone is not an ideal indicator of feel and performance, because it does not give an idea of the overall flex, feel, and performance of the shaft, but rather just the flex of the butt of the shaft.

As used herein, the "shaft kick point" is defined as the ratio of the shaft tip flex to the shaft butt flex of the shaft. See above relating to the shaft tip flex and the shaft butt flex for examples of measurement standards. The shaft kick point is one of the properties 232 that is indicative of performance of the shaft 231 for the user 202. For example, a player with a high club head speed and a high attack angle would be recommended a lower kick point, meaning that the tip end of the shaft does not flex significantly more than the butt end. This is because a player with a high club head speed does not want too much additional deflection as the player is already capable of generating adequate deflection from their high swing speed to generate a preferable attack angle at impact. However, conversely, a player with a low club head speed may be recommended a higher shaft kick point, meaning that the tip of the shaft 231 would flex more, which allows for the golfer to generate a preferable of an attack angle at impact as possible, which they would not be able to achieve with a lower shaft kick point, because the higher kick point provides added deflection to the shaft during the swing.

As used herein, the "shaft flex" is defined as the manufacturer's assigned flex for the shaft. The shaft flex includes, for example, X (extra stiff), S (stiff), R (regular), A (amateur), Wedge flex, and W (women's). The shaft flex is a property 232 that differs for each shaft 231 and for each manufacturer. For example, many of the shafts 231 may be labeled as X flex, but have very different flex profiles. Also, different manufacturers may have assign different shaft flex to similar shafts. Manufacturer A may assign X flex while manufacturer B may assign S flex, even though the shaft flex profiles are similar.

As used herein, the "shaft flex profile" is defined as the shaft flex values at varying locations over the shaft from the tip end to the butt end of the shaft. The shaft flex values may be measured in cycles per minute if the frequency is measured at various locations along the shaft, or may be measured in $N*m^2$ (or $Pa*m^4$) as the product of Modulus of Elasticity (E) and Area Moment of Inertia (I), otherwise known as flexural rigidity, or EI. There is no one standard for shaft flex profile, so any conventional flex profile coding systems, e.g., a conventional profile coding system that represents shaft stiffness at plural locations about the length of the shaft, may be used. For example, shaft recommendations may include the shaft profiling convention described in U.S. Pat. No. 8,337,336 (incorporated by reference herein in its entirety), particularly the convention described at page 3, line 20 to page 5, line 48.

As used herein, the "shaft length" is defined as the measured length of the shaft. The shaft length is generally dependent more on the height, arm length, and other variables pertaining to the player themselves, and not generally dependent on the swing parameters 233 or any sensor data 256. As such, the shaft length is not a reliable measurement for performance and feel that can be accurately determined using the sensor 252.

As used herein, the "shaft materials" are defined as the materials the shaft comprises. The shaft may comprise any number of materials. The materials affect the other properties 232 of the shafts 231, but are not accurately recommended using the sensor data 256 from the sensor 252, because similar performance and feel may come from a variety of different shafts that have different materials. Moreover, similar shaft flex, shaft flex profiles, kick points, etc., may come from shafts having different materials, so merely recommending materials is not as useful a factor for determining a proper shaft for a user 202. However, a general recommendation of shaft materials may be more useful. For example, for irons and wedges especially, players with slow swing speeds may not be able to get the deflections necessary to obtain preferable head speed values from metal shafts. For these kinds of players, graphite shafts are generally recommended because the weight of the graphite shafts may be lower and a graphite shaft is capable of more deflection. However, golfers with higher swing speeds generally need metal irons. As such, the swing parameters 233 may be utilized to determine the general shaft materials to recommend to the user 202, such as graphite or metal.

As used herein, the "swing weight" is defined as the measurement of a golf club's weight about a fulcrum point which is established at a specified distance from the grip end of the club. The swing weight may be measured according to those of skill in the art, and may be measured using a swing weight scale, such as the Maltby Design Golf Club Swingweight Scale. The swing weight relates to the entire club, so the shaft is a factor in determining swing weight. During a fitting recommendation for a shaft, the club head is generally already known, and a stock grip can be assumed, so the only variable is the shaft itself. Using the swing parameters 233, the shaft algorithm 238 can first make a determination of a recommended swing weight for the user 202, and then determine which shafts 231 would satisfy that swing weight within a given tolerance. The swing weight is especially important for the feel of the golf club to the user 202. The swing weight is generally described as how heavy the golf club feels to the golfer, and not how heavy the golf club actually is.

As used herein, the "shaft torque" is defined as the angle to which the shaft rotates when put under a load or is subjected to torque (e.g., 1 lb-ft). Shaft torque may be measured using a torque machine. In such a measurement approach, the shaft is clamped near the butt end of the shaft, more specifically at 32" from the tip end of the shaft, and the tip of the shaft is inserted into a 6" radius cylinder, where a 2 pound weight is attached at the radius of the cylinder in order to apply 1 foot pound of torque over the shaft from the tip end to the clamp, which is 32" toward the butt end of the shaft. The shaft torque has an effect on performance of the shaft, because the shaft torque is a measure of the shafts resistance to twisting. For example, a golfer with a high swing speed, and thus a high club head speed, would not want a shaft with a lot of torque because the club head may over rotate and cause a hook shaped shot. However, for a golfer with a slower swing speed, and thus a lower club head speed, the golfer may need some extra torque in order to get the club head back to square prior to impact, so a higher torque shaft may be recommended. However, most high handicap to mid handicap golfers would not notice the effect of torque on the feel of the shaft, and until you get to a low handicap player, the effect of torque is not as important.

In some implementations, any number of properties 232 may be stored for each of the shafts 231, but the shaft algorithm 238 may only use the properties 232 selected as shaft parameters 240 in making the determination. As such, the shaft parameters 240 may be different depending on the operator of the computing device 210, or on the specific testing being completed. For example, one fitting professional may believe that butt flex and tip flex are both properties 232 of the shafts 231 that are most indicative of performance and feel, and thus may select the butt flex and the tip flex as the shaft parameters 240 used by the shaft algorithm 238 to make a recommendation of a shaft for user 202. In such an implementation, the operator of the computing device 210 may be able to choose ahead of time, from the entire list of properties 232, the properties 232 the operator would prefer to implement as shaft parameters 240 into the shaft algorithm 238 to make the shaft recommendation determinations. From there, the necessary swing parameters 233 that were determined to correlate to the shaft parameters 240 are input into the shaft algorithm 238 to determine the recommended values 242 for the shaft parameters 240 and then compare them to the actual values 241 to determine the recommended shaft(s) 231.

However, in other implementations, the database 226 may only store the properties 232 determined to be most accurate as shaft parameters 240 in the shaft algorithm 238 for determining a recommended shaft for user 202.

The shaft parameters 240 are indicative of the performance and feel of the shafts 231, and shafts 231 of different performance levels and having different feel may be recommended to players of different skill levels. For example, a heavy shaft, with a low kick point may be recommended to a golfer with a higher swing speed, while a light shaft with a higher kick point may be recommended to a golfer with a lower swing speed. The database 226 may store actual values 241 for any number of shaft parameters 240 for any number of shafts 231. The ultimate goal, as will described in more detail below, is to determine recommended values 242 for the shaft parameters 240 using the shaft algorithm 238 based on the sensor data 256 that can then be compared to the actual values 241 of the shaft parameters 240 to make a recommendation of which shaft or shafts 231 should be recommended to the user 202.

In the past, shaft recommendations have been made based solely on a swing parameters such as swing speed or attack angle. Then, using the swing parameters, a guess of which shafts would work best is determined. As such, the sensor data 256b and swing parameters 233 have previously only been used to generate a mental picture of the golfer (user 202), and then make a recommendation of a shaft based on the flex, weight, etc., that the fitter believed to be the closest. As mentioned above, the flex of the shafts is different among different manufacturers, and each shaft can be drastically different even though they have the same labeled shaft flex. Further, the shaft weight is indicative of the shaft feel, but simply having shaft weight doesn't paint the whole picture of how that weight is distributed, for example. So although prior shaft recommendations have been done using swing parameters 233, the swing parameters 233 have only been utilized as general indicators that may lead to a best guess conclusion on which shafts to recommend to the golfer. While this approach may yield decent results, and the recommended shafts may be in the realm of the correct shafts for the golfer, this approach does not fully utilize the swing parameters 233 and sensor data 256 to generate more accurate shaft recommendations utilizing algorithms, such as shaft algorithm 238, to generate recommended values 242 for the shaft parameters 240 that can be compared to the actual values 241. In addition, prior approaches generally looked at each shaft parameter individually based on the swing parameters 233, but did not take a comprehensive look at the combination of multiple shaft parameters 240 in view of the swing parameters 233, in order to recommend shafts that most accurately represent the entire shaft performance and feel based on the swing parameters 233 generated using the sensor data 256.

For example, the fitter may have previously determined the swing speed or club head speed of the golfer was 110 mph and, from there, determined that an X flex shaft is preferable, having a shaft weight of 65 g, for example. The fitter may have then looked at angle of attack, and determined that from the X flex, 65 g shafts that one of them had a stiffer tip end that would deflect less, and recommended that shaft to the golfer. However, in doing this, the fitter is making guesses based on swing parameters 233 without accounting for how those swing parameters 233 can be utilized to calculate recommended values 242 for shaft parameters 240 that can be compared to actual values for shaft parameters 240. In addition, the prior art fitting processes generally utilize this deductive approach that eliminates shafts at each step, when in fact the shafts that golfer ultimately should use based on an analysis of each factor all at once may be eliminated in a prior step. For example, the fitter may eliminate the R-flex shafts because the fitter believes the golfer needs an X-flex. However, when looking at the R-flex shaft that has been eliminated, the R-flex shaft may actually have a kick point, shaft frequency, and shaft weight value, which when looked at in totality create a better overall measure of shaft performance of feel, are better suited for the golfer than any of the X-flex shafts available.

The method described herein for shaft recommendations utilizes the swing parameters 240 in the shaft algorithm 238 to determine recommended values 242 for shaft parameters 240 that can be directly compared to the actual values 241 to determine recommended shafts. By utilizing a plurality of shaft parameters 240 that are indicative of the overall performance and feel of the shafts 231 in making the recommendation, the recommended shafts 231 are more likely to reflect the best performing and feeling shafts for the golfer. In addition, by using the shaft algorithm 238, the guess work for the fitters is taken out of the equation, and the shaft recommendations are more consistent and accurate.

Although any number of shaft parameters 240 may be utilized for shaft recommendations for each golfer, extensive robot testing, player testing, lab tests, and shaft measurements indicate certain shaft parameters 240 to the most indicative of the performance and feel of the shaft, as is explained above with reference to each of the shaft parameters 240. In addition, in order to determine the recommended values 242 for the shaft parameters 240 using the shaft algorithm 238 in a way that is meaningful and relatable to actual values 241 for the shaft parameters 240, the sensor data 256b and the swing parameters 233 must be accurately calculable using the sensors 252. For example, because, as explained above, the shaft flex is a loose determination that differs from shaft to shaft and from manufacturer to manufacturer, it is more difficult to accurately determine recommended values 242 for shaft flex that align well with actual values 241 for shaft flex of the shafts 231.

With that in mind, a preferable implementation utilizes shaft frequency, shaft kick point, and shaft weight as the shaft parameters 240 to be utilized by the software application 220 to accurately determine a recommended shaft from the shafts 231 based on a swing of the reference golf club 250 by the user 202. Each of these three shaft parameters 240 individually is indicative of performance and feel, but in combination provides a comprehensive indication of the performance and feel of the shaft. In addition, actual values 241 for each of these shaft parameters 240 are able to measured using well known measurement equipment, and recommended values 242 for each of these shaft parameters 240 are able to be calculated using swing parameters 233 generated from the sensor data 256. While there are other shaft parameter 240 combinations that may be utilized, the shaft frequency, shaft kick point, and shaft weight are a preferable example of the shaft parameters that have yielded accurate and reliable results through testing.

In order to determine the actual values 241 for the shaft parameters 240 for each of the shafts 231, the measurements are conducted in accordance with those described above for each of the shaft parameters 240. However, other measurement procedures may utilized as known to those in the art so long as the measured values correspond to the shaft parameters 240.

In order to determine the recommended values 242 for the shaft parameters 240, a determination of which swing parameters 233 most accurately correspond to each shaft parameters 240 is required. This determination is made based on player data, lab data, robot data, and fitter surveys. For example, after reviewing player data, lab data, and robot data, it was determined that maximum club head speed is the best indicator of shaft weight. For example, the combination of all the data indicated that higher maximum club head speeds in combination with heavier shafts yielded an overall better combination of accuracy and longer ball flights and were also reported to have better feel for the golfers using the heavier shafts that had higher maximum club head speed. On the contrary, the combination of all the data indicated that lower maximum club head speeds in combination with lighter shafts yielded an overall better combination of accuracy and longer ball flights and were also reported to have better feel for the golfers using the lighter shafts that had lower maximum club head speeds. As a result, it was determined that maximum club head speed should be the swing parameter 233 used to make a correlation between a swing parameter 233 and the recommended values 242 for the shaft parameters 240.

This same process was followed for the shaft frequency and the shaft kick point. It was determined from all the data that the swing parameter 233 that most accurately corresponded to the shaft frequency was the maximum tangential acceleration. The shaft frequency is a measure of the vibration of the shaft, or how much the shaft deflects when put into motion by a certain force. The tangential acceleration, based on the physics of the golf swing, is a good indicator of the deflection of the shaft. The maximum tangential acceleration is thus a good indicator of the maximum deflection of the shaft during the swing. As a result, with the maximum tangential acceleration being a good indicator of maximum deflection, and the shaft frequency being a good measure of shaft deflection, it was determined to use the maximum tangential acceleration as the swing parameter 233 for calculating shaft frequency in the shaft algorithm 238.

It was also determined from all the data that the swing parameters 233 that most accurately corresponded to the shaft kick point were maximum club head speed and attack angle. During testing, golfers tended to hit more down on the ball with shafts having a lower shaft kick point which is explained by the club head impacting the ball while the shaft is bending (deflecting) or releasing. The data was used to try and identify shafts that have a shaft kick point that allows the golfer to achieve closer to a preferable attack angle. The preferable attack angle is also dependent on the maximum club head speed. For example, a golfer who has a lower maximum club head speed will need more deflection of the shaft and a higher shaft kick point to get to a preferable attack angle. Golfers with higher maximum club head speeds will not need as much help from the deflection of the shaft to achieve a preferable attack angle because their club head speed provides enough deflection without the need for extra deflection from a shaft with a higher kick point, and thus higher maximum club head speed players require lower kick point shafts. In view of this information, it was determined that the attack angle and the maximum club head speed were the most indicative swing parameters 233 for generating the shaft kick point recommended values 242 using the shaft algorithm 238.

Once the determination is made, the shaft algorithm 238 is programmed to determine recommended values 242 for the shaft parameters 240 utilizing the swing parameter 233 values. This is done using best fit linear models, where the best fit linear models are based on comparisons between actual values 241 of the shaft parameters 240 and the swing parameters 233 calculated from player testing, lab testing, robot testing, and Head Measurement Technology ("HMT") calibration (e.g., Foresight Sports™ HMT) (as described above). This best fit linear model is ultimately calculated by the shaft algorithm 238. The shaft algorithm 238 can then be dynamically updated based on actual fitter feedback from real-world fitting results that are entered into the software application 220 on the back end by the fitter, thereby updating the best fit linear model, and thus the shaft algorithm 238, as will be described in greater detail below.

In order to generate the best fit linear model for the shaft algorithm 238, the sensors 152, specifically sensors similar to those of sensor 152f, are utilized to capture data relating to a wide variety of golfers. For example, tour players, scratch golfers, low handicap golfers, mid handicap golfers, and high handicap golfers are all tested to gather data from a wide range of players having a wide range of playing abilities generating a wide range of values of each of the swing parameters 233. The shafts being used by each of the golfers in the tests are also measured for their actual values 241 of their shaft parameters 240. So, for each golfer, at least one shaft is tested, and the performance numbers and feel feedback and compared against the actual values 241 for the shaft parameters 240.

As an example, when looking at the swing parameter 233 maximum club head speed with a golfer who has a high maximum club head speed, such as 105 mph, if the golfer is tested using both a high shaft weight shaft and a mid shaft weight shaft and the performance numbers (e.g., ball speed, ball spin, distance, trajectory) look best with the high shaft weight shaft, then one data point utilized when calculating the best fit linear model for the recommended values 242 of shaft weight in the shaft algorithm 238 would be the actual value 241 for the shaft weight for the high shaft weight shaft plotted against the maximum club head speed of the golfer, which in this case would be 105 mph.

The same process is carried out for each of the shaft parameters 240 and their associated swing parameters 233.

As more and more golfers are tested, more data points will be used for determining the best fit linear model for calculating each of the selected recommended values 242 for the shaft parameters 240. As such, once the best fit linear model is calculated for each of the shaft parameters 240 in the shaft algorithm 238, the shaft algorithm 238 utilizes the swing parameters 233 of the user as an input to determine the recommended values 242 for the shaft parameters 240. The shaft algorithm 238 then compares the recommended values 242 against the actual values 241 for the shaft parameters 240 stored in the database 226 to determine which of the shafts 231 to recommend, as will be described in greater detail below.

Below outlines examples of following the above steps for gathering data and having the shaft algorithm 238 utilize the data to determine the best fit linear models for each of the three preferable shaft parameters 240 discussed above-shaft frequency, shaft kick point, and shaft weight.

First, referring to the shaft weight, the wide variety of players were tested looking for best performance numbers (e.g., ball speed, trajectory, ball flight, etc.) and best reported feel for the golfer for a at least two shafts. Once the performance numbers were calculated and the feel input was received for each particular golfer, the maximum club head speed of that golfer and the shaft weight of the shaft that provided the best feel and performance are recorded as a data point (e.g., plotting the shaft weight as the x-axis and the maximum club head speed as the y-axis). Once a wide range of golfers were tested, the shaft algorithm 238 generates a best fit linear model correlating maximum club head speed to the shaft weight. As one example, after significant player testing, the following equation (4) was determined which represents the best fit linear model calculated by the shaft algorithm 238:

$$\text{Shaft Weight}_R = -117.2 + 2.68 * \text{Max Club Head Speed} \qquad (4)$$

where the Shaft Weight$_R$ is the recommended value 242 for the shaft parameter 240 "shaft weight" and Max Club Head Speed is the maximum club head speed which is the swing parameter 233 utilized for correlating the users 202 swing to the shaft weight, as described in more detail above.

The equation (4) is just one example of a best fit linear model and depending on the players tested, the shafts tested, and the corresponding actual values 241 for the shaft weight and actual values for the maximum club head speed input into the algorithm, the equation (4) could change.

In some implementations, once the shaft algorithm 238 determines the best fit linear model for the recommended shaft weight (e.g., equation (4)), that best fit linear model does not change, and is a static best fit linear model which is utilized by the software application 220. As such, when a fitter downloads the software application 220 and proceeds to conduct a fitting for a shaft on user 202, the users 202 maximum club head speed is entered into the static best fit linear model (e.g., equation (4)), and a recommended value 242 for the shaft weight is output.

However, in other implementations, the best fit linear model determined by the shaft algorithm 238 is only an initial best fit linear model. In such an implementation, the best fit linear model dynamically updates as new fitting information is input into the software application 220. For example, once the user 202 takes a swing with the reference golf club 250, two shafts may be output as recommended shafts 231 for the user 202 where the first shaft has a shaft weight normally recommended to golfers having a maximum club head speed similar to the users 202 and the second shaft has a shaft weight lower than generally recommended for the users 202 maximum club head speed. In such an example, the fitter may recommend to the user 202 the second shaft that has a shaft weight slightly lower than generally recommended for golfers having maximum club head speeds similar to the user 202 because the performance and feel are better for the user 202. In response to the selection of the second shaft, as an example, the shaft weight of the second shaft along with the maximum club head speed of the user 202 are input into the shaft algorithm 238 as an additional data point and the best fit linear model is dynamically updated to reflect the additional data point.

In implementations where the shaft algorithm 238 is dynamically updated, each additional data point may update the shaft algorithm 238 universally, such that each fitters/users software application 220 is now updated to reflect the additional data point. As such, as numerous fitters/users are using the software application on a continuous basis, the shaft algorithm 238 is constantly updated with additional data points thereby updating the best fit linear models based on each and every recommended shaft and the corresponding shaft parameters 240 and swing parameters 233.

As another example, in implementations where the shaft algorithm 238 is dynamically updated, each additional data point input by each individual fitter/user may only locally update their specific software application 220 on their specific device or on their specific account. In such examples, because different fitters/users have different tendencies, or different opinions, each fitter/user may prefer to have the shaft algorithm 238 update dynamically to more accurately reflect their fitting style. Over time, the shaft algorithm 238 will learn the particular fitter/users preferences, and the best fit linear models will be updated to reflect them.

Each fitter/user may also have the option to select universal updating, local updating, or no updating at all such that the shaft algorithm 238 (and/or the algorithm 236 and the lie algorithm 243) are universally updated with each fitters additional data point, only updated with the particular fitter/users data points, or not updated at all, respectively.

It should be noted that descriptions of dynamically updating the shaft algorithm 238 also apply to the algorithm 236 and the lie algorithm 243. As such, each of the algorithm 236 and the lie algorithm 243 may also be universally or locally updated, or not updated at all, based on additional data points.

It should also be noted that the method described above with reference to dynamic updating utilizing additional data points also apply to the other shaft parameters 240, including the shaft frequency and the shaft kick point, which will be described below. As such, each of the shaft parameters 240, including shaft kick point and the shaft frequency, may be dynamically updated based on fitter/user inputs, either universally or locally.

Second, referring to the shaft kick point, the wide variety of players were tested looking for best performance numbers (e.g., ball speed, trajectory, ball flight, etc.) and best reported feel for the golfer for at least two shafts. Once the performance numbers were calculated and the feel input was received for each particular golfer, the maximum club head speed and attack angle of that golfer and the kick point of the shaft that provided the best feel and performance are recorded as a data point. Once a wide range of golfers were tested, the shaft algorithm 238 generates a best fit linear model correlating maximum club head speed and attack angle to the shaft kick point. As one example, after significant player testing, the following equation (5) was determined which represents the best fit linear model calculated by the shaft algorithm 238:

$$\text{Kick Point}_R = 82.8 - 0.48 * \text{Max Club Head Speed} + 3.32 * \text{Attack Angle} \quad (5)$$

where the Kick Point$_R$ is the recommended value 242 for the shaft parameter 240 "shaft kick point" and Max Club Head Speed is the maximum club head speed which, along with Attack Angle are the swing parameters 233 utilized for correlating the users 202 swing to the shaft kick point, as described in more detail above.

The equation (5) is just one example of a best fit linear model and depending on the players tested, the shafts tested, and the corresponding actual values 241 for the shaft kick point and actual values for the maximum club head speed and attack angle input into the algorithm, the equation (5) could change. Additionally, as described above with reference to the best fit linear model for the shaft weight, the best fit linear model generated by the shaft algorithm 238 for the shaft kick point may be dynamically updated.

Third, referring to the shaft frequency, the wide variety of players were tested looking for best performance numbers (e.g., ball speed, trajectory, ball flight, etc.) and best reported feel for the golfer for at least two shafts. Once the performance numbers were calculated and the feel input was received for each particular golfer, the maximum tangential acceleration of that golfer and the shaft frequency of the shaft that provided the best feel and performance are recorded as a data point. Once a wide range of golfers were tested, the shaft algorithm 238 generates a best fit linear model correlating maximum tangential acceleration to the shaft frequency. As one example, after significant player testing, the following equation (6) was determined which represents the best fit linear model calculated by the shaft algorithm 238:

$$\text{Frequency}_R = 240 + 0.40 * \text{Max Tangential Acceleration} \quad (6)$$

where the Frequency$_R$ is the recommended value 242 for the shaft parameter 240 "shaft frequency" and Max Tangential Acceleration is the maximum tangential acceleration which is the swing parameter 233 utilized for correlating the users 202 swing to the shaft frequency, as described in more detail above.

The equation (6) is just one example of a best fit linear model and depending on the players tested, the shafts tested, and the corresponding actual values 241 for the shaft frequency and actual values for the maximum tangential acceleration input into the algorithm, the equation (6) could change. Additionally, as described above with reference to the best fit linear models for the shaft weight and the shaft frequency, the best fit linear model generated by the shaft algorithm 238 for the shaft frequency may be dynamically updated.

Once the best fit linear models have been calculated by the shaft algorithm 238, each time the user 202 swings the reference golf club 250 the sensor 252 generates the sensor data 256 which is converted to swing parameters 233 by the software application. The swing parameters 233 are then input into the shaft algorithm 238 so that the shaft algorithm 238 can calculate the recommended values 242 for the shaft parameters 240. In one preferable implementation, as described above, where the shaft parameters 240 utilized for recommending a shaft to the user 202 are the shaft kick point, the shaft frequency, and the shaft weight, the shaft algorithm 238 outputs recommended values 242 for each of these three shaft parameters 240.

The shaft algorithm 238 then determines at least one recommended shaft 231 by comparing the actual values 241 and the recommended values 242 for the selected shaft parameters 240 which are, in this example, shaft kick point, shaft frequency, and shaft weight. In order to do this, the shaft algorithm 238 analyzes, in a three-dimensional space, the actual values 241 against the recommended values 242. The three-dimensional space being defined by three axes, where each axis represents one of the selected shaft parameters 240. The comparison between the actual values 241 and the recommended values 242 is completed by calculating the three-dimensional distance between them.

The three-dimensional distance is calculated utilizing equation (7) below:

$$D=\sqrt{(SP1_R-SP1_A)^2+(SP2_R-SP2_A)^2+(SP3_R-SP3_A)^2} \qquad (7)$$

where D is the three-dimensional distance, $SP1_R$ is the recommended value 242 for the first shaft parameter 240, $SP1_A$ is the actual value 241 for the first shaft parameter 240, $SP2_R$ is the recommended value 242 for the second shaft parameter 240, $SP2_R$ is the actual value 241 for the second shaft parameter 240, $SP3_R$ is the recommended value 242 for the third shaft parameter 240, and $SP3_R$ is the actual value 241 for the third shaft parameter 240.

In the above example, discussing the preferable implementation, equation (7) includes shaft weight, shaft frequency, and shaft kick point as the shaft parameters 240 SP1, SP2, and SP3. As such, the shaft algorithm 238 calculates the three-dimensional distances between the recommended values 242 for the shaft parameters 240 generated after the users 202 swing (or combination of a plurality of swings) and the actual values 241 for each of the shafts 231 in the database 226. The shafts 231 resulting in the lowest value for distance, D, are the shafts that are recommended for the user 202.

In some implementations, only one shaft is recommended, while in other implementations a plurality of shafts may be recommended. For example, if two shafts are recommended, Shaft A and Shaft B, where both shafts have similar values for D, the fitter/user may have a preference for Shaft B, for example, because Shaft B may have a lower shaft weight than Shaft A and the fitter/user prefers to recommend/use a shaft with a lower shaft weight.

In addition, the shaft algorithm 238 may not compare the actual values 241 to the recommended values 242 for each of the shafts 231 in the database. The database 226 may include shafts 231 for a variety of different club types, such as irons, wedges, woods, putters, etc. As such, the fitter/user of the software application 220 may select the type of golf club being fit, and the database 226 is subsequently updated to only include the shafts 231 that are for that type of golf club such that the shaft algorithm 238 only considers those shafts 231.

In addition, each fitter/user may prefer only a limited set of shafts 231, or may only have certain of the shafts 231 in stock. As such, the database 226 may be updated to reflect only the preferable and/or in stock shafts 231, such that the shaft algorithm 238 only considers the actual values 241 for the preferable and/or in stock shafts 231. In such an example, the inventory of the shafts 231 may be included in the database 226, such that when one of the shafts 231 is out of inventory, the database 226 dynamically updates such that the shaft recommendations output as a result of the shaft algorithm 238 are only the shafts 231 that are in stock.

It should be noted that in implementations where a different number of shaft parameters 240 are selected, the space being analyzed will have dimensions equal to the number of selected shaft parameters 240. For example, if only two shaft parameters 240 are analyzed by the shaft algorithm 238, such as shaft weight and shaft kick point, the shaft algorithm 238 will only compare the actual values 241 and the recommended values 242 in a two-dimensional space. Thus, depending on the number of shaft parameters 240 being analyzed, the distance, D, is calculated based on equation (8) below:

$$D=\sqrt{(SP1_R-SP1_A)^2+(SP2_R-SP2_A)^2+...(SPX_R-SPX_A)^2} \qquad (8)$$

where D is the X-dimensional distance, $SP1_R$ is the recommended value 242 for the first swing parameter 240, $SP1_A$ is the actual value 241 for the first swing parameter 240, $SP2_R$ is the recommended value 242 for the second swing parameter 240, $SP2_A$ is the actual value 241 for the second swing parameter 240, and so on, and X is the number of shaft parameters 240 being analyzed.

Figure 4A:
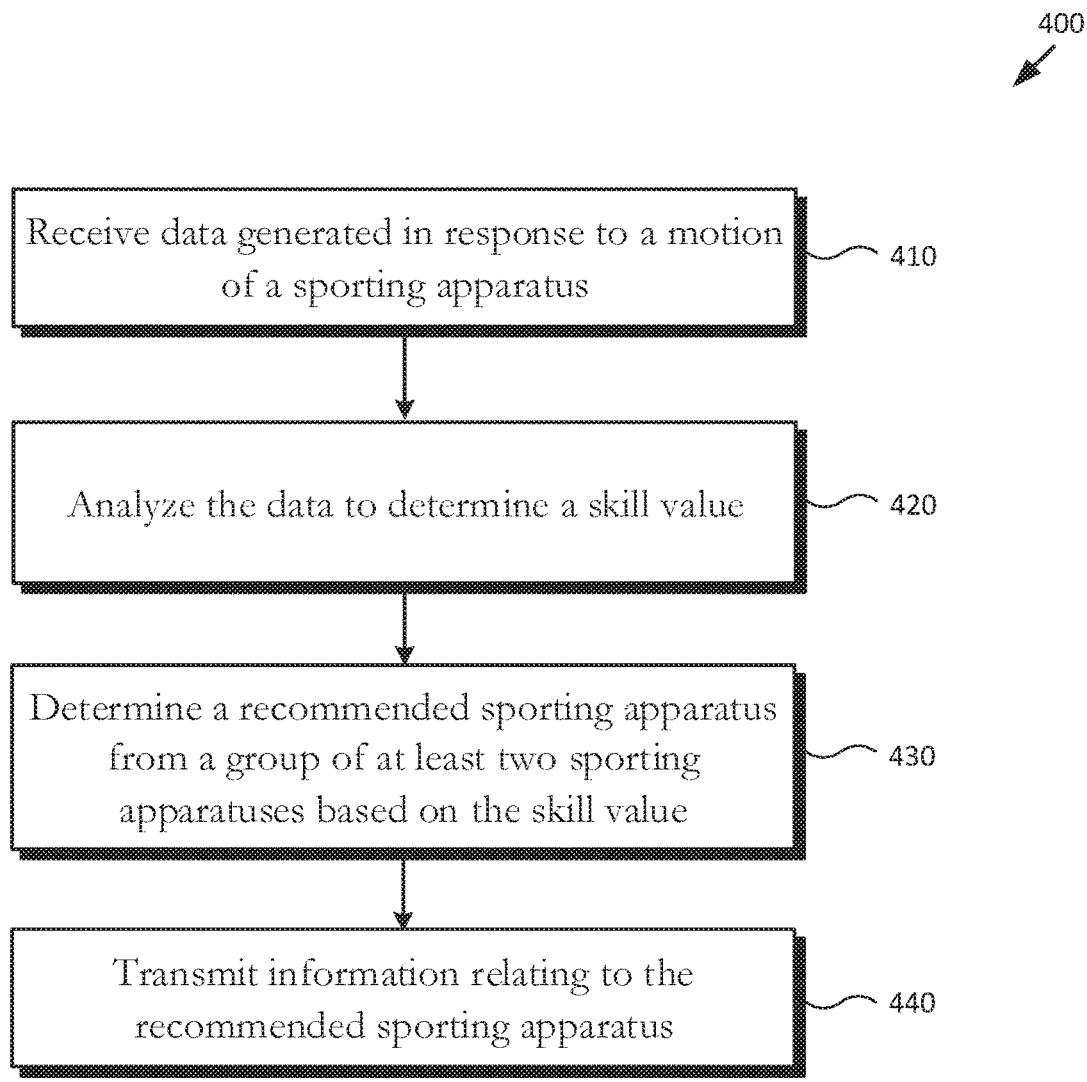
FIG. 4A is a flowchart diagram illustrating a method for use by systems and apparatus of the present disclosure.
Figure 4B:
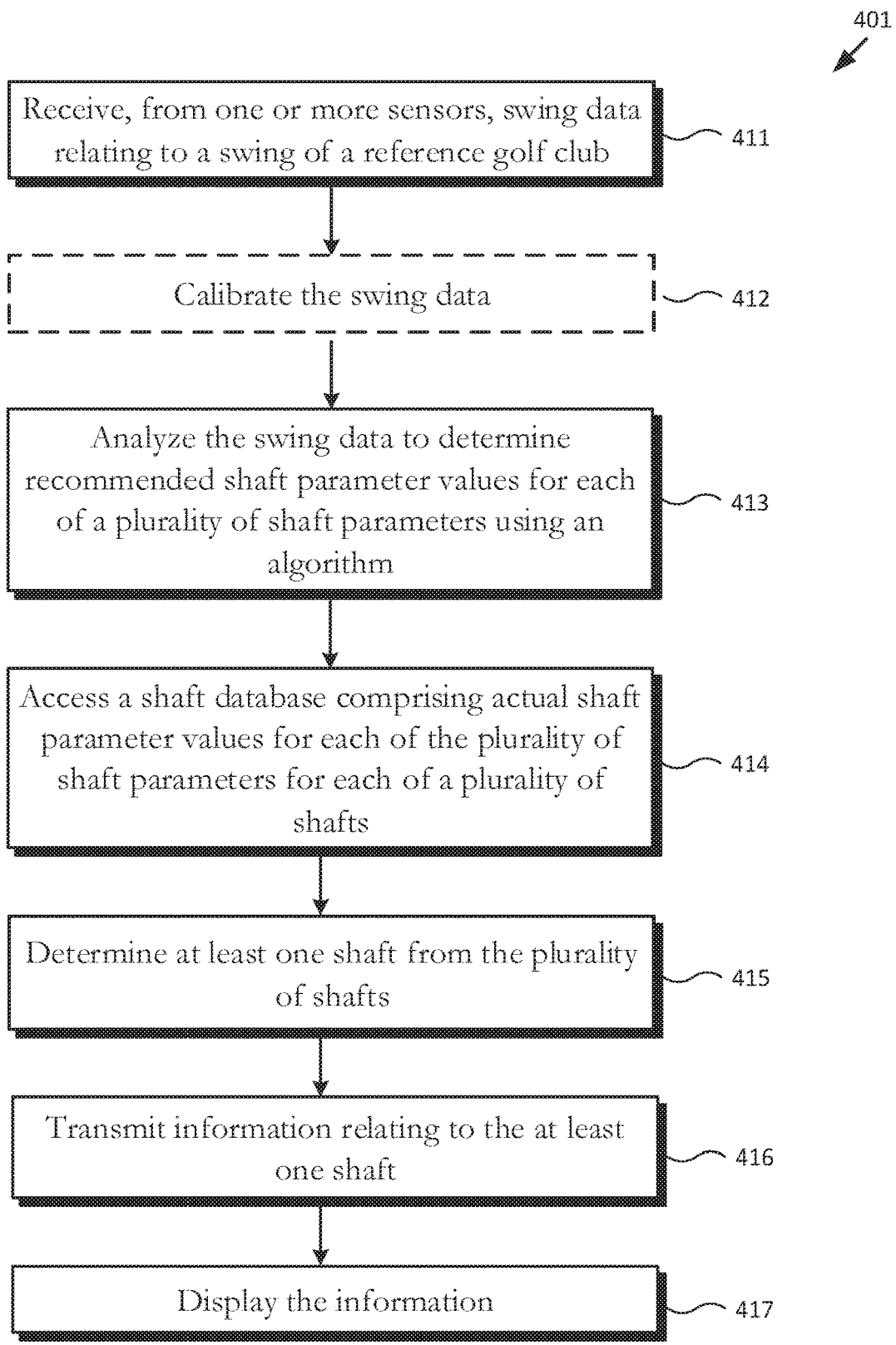
FIG. 4B is another flowchart diagram illustrating a method for use by systems and apparatus of the present disclosure.

Now referring to FIG. 4B, FIG. 4B is a flowchart diagram illustrating a method for use by systems and apparatus of the present disclosure. The approach and technique indicated by flowchart 401 are sufficient to describe at least one implementation of the present disclosure, however, other implementations of the disclosure may utilize approaches and techniques different from those shown in flowchart 401. Furthermore, while flowchart 401 is described with respect to FIGS. 2A-2C, the disclosed inventive concepts are not intended to be limited by specific features shown and described with respect to FIGS. 2A-2C. Furthermore, with respect to the method illustrated in FIG. 4B, it is noted that certain details and features have been left out of flowchart 401 in order not to obscure the discussion of inventive features in the present application.

Flowchart 401 (at 411) includes receiving, from one or more sensors, swing data relating to a swing of a reference golf club. For example, the computing device 210 and/or the server 270 receive the sensor data 256, where the sensor data 256 is generated in response to a swing of the reference golf club 250.

Flowchart 401 (at 412) includes calibrating the swing data. For example, the sensor data 256 is calibrated as described above, by comparing the sensor data 256 and/or the swing parameters 233 calculated based on the sensor data 256 generated by a first sensor 252 of the type similar to sensors 152a-152e to the sensor data 256 and/or the swing parameters 233 calculated based on the sensor data 256 generated by a second sensor 252 of the type similar to sensor 152f.

It should be noted that step 412 has a dashed outline indicating that calibrating is not required. In some instances it may be beneficial to calibrate the sensor data 256 while in other it may not be necessary. Depending on the accuracy of the result generated and the requirement of accuracy in the fitting test, calibration may or may not be an advised step in the method.

Flowchart 401 (at 413) includes analyzing the swing data to determine recommended shaft parameter values for each of a plurality of shaft parameters using an algorithm. For example, the sensor data 256 received in response to the swing of the reference golf club 250 is analyzed to determine recommended values 242 for the shaft parameters 240 using the shaft algorithm 238. As outlined above, the shaft parameters 240 are based on the swing parameters 233 which are calculated using the sensor data 256. As such, the swing parameters 233 are utilized in calculating recommended values 242 for the shaft parameters 240.

Flowchart 401 (at 414) includes accessing a shaft database comprising actual shaft values for each of the plurality of shaft parameters for each of a plurality of shafts. For example, the computing device 210 accesses the database 226 including the plurality of shafts 231, where each of the shafts 231 have actual values 241 for each of the shaft parameters 240. It should be noted that the database 236 may be located on the server 270, as described above, such that the computing device 210 may access its own device memory 214 to access the actual values 241 or may access the server memory 294.

Flowchart 401 (at 415) includes determining at least one shaft from the plurality of shafts. For example, the shaft algorithm 238 determines (or selects) at least one of the plurality of shafts 231 having actual values 241 for the shaft parameters 240 most similar to the recommended values 242 for the shaft parameters 240 calculated by the shaft algorithm 238. This may be done, for example, utilizing the distance, D, equation outlined above.

Flowchart 401 (at 416) includes transmitting information relating to the at least one shaft. For example, the computing device 210 may transmit the information to the display 238 or, in some implementations, the server 270 may transmit the information to the computing device 210 which is then transmitted to the display 238.

Flowchart 401 (at 417) includes displaying the information. For example, the information is displayed on the display 238 of the computing device 210.

This method described in flowchart 401 provides significant advantages over prior shaft fitting systems. Prior shaft fitting systems do not generate recommendations based on recommended values 242 for actual shaft parameters 240, but rather utilize characteristics of a user's swing to determine shafts, which then leaves the fitter to have to use their judgement on which shafts may fit the swing characteristics. Some prior shaft fitting systems also output shaft flex, for example, but as described above shaft flex is not a consistent standard and thus results in inconsistent fitting results. The method of flowchart 401 utilizes sensor data 256 generated from a swing to calculate swing parameters 233 values, and then utilizes the swing parameters 233 to calculate recommended values 242 for shaft parameters 240. Then, by accessing a shaft database 226 having actual values 241 for the shaft parameters 240 as measured in a lab, for example, the closest shaft 231 can be recommended. This is an accurate and consistent method that reduces guess work and human error, and creates a holistic picture of the right shaft for the user 202, by generating recommended values 242 for the shaft parameters 240 and comparing them against actual values 241.

The lie algorithm 243 follows a similar method as the shaft algorithm 238 where a best fit linear model is created based on swing parameters 233. However, the lie algorithm 243 utilizes the swing parameters 233 to generate a recommendation of the lie angle for the club head.

In some implementations, the lie algorithm 243 may be programmed to output the recommended lie angle for the golf club. In such an implementation, the current lie angle of the golf club must be determined, and then adjusted based on the recommended lie angle. For example, if the lie angle output is 63° and the club head has a current or factory lie angle of 65°, the golf club would have to be adjusted such that the lie angle is reduced by 2°.

In preferable implementations, the lie angle recommendation is a "lie fit" recommendation, where the output of the lie algorithm 243 is the number of degrees of adjustment needed. In the example from the preceding paragraph, the software application 220 would output −2°, for example, which would indicate that the club head required a 2° negative adjustment. In this implementation, the software application 220 may store the factory lie angle for each of the golf clubs 228 such that when a lie fitting is being conducted, the club lie angle is already known by the software application 220 and utilized by the lie algorithm 243.

In order to generate the best fit linear model for the lie fit, calibration between the sensors 252 is a preferable first step. The sensors 152*a*-152*e* are not as accurate measuring lie angles, including impact lie and initial lie, and thus preferably undergo a calibration against a sensor 252 of a type similar to that of sensor 152*f*, such as an HMT. In order to achieve a calibration, the swing parameters 233 calculated based on the sensor 252 of a type similar to that of sensors 152*a*-152*e* are calibrated against the impact lie of the sensor 252 of a type similar to that of the sensor 152*f* utilizing a regression model.

The regression model is defined as in equation (9) below:

$$Y = XB \qquad (9)$$

where Y is the swing parameter 233 output from the sensor 252 of the type similar to that of sensor 152*f* (HMT), in this case the swing parameter 233 is the impact lie, X is the swing parameters 233 generated from the sensor 252 of the type similar to that of sensors 152*a*-152*e*, and B is the vector of coefficients for the best fit linear model. In other words, B determines the coefficients to be utilized to calibrate the swing parameters 233 from the sensor 252 of type 152*a*-152*e* with the impact lie of the sensor 252 of type 152*f*. Because Y and B are vector quantities and X is a matrix, Y, B, and X can be expressed as below:

$$Y = \begin{bmatrix} y_1 \\ y_2 \\ \vdots \\ y_3 \end{bmatrix}, X = \begin{bmatrix} 1 & x_{11} & x_{21} & x_{31} & x_{41} & x_{51} \\ 1 & x_{12} & x_{22} & x_{32} & x_{42} & x_{52} \\ 1 & x_{13} & x_{23} & x_{33} & x_{43} & x_{53} \\ 1 & x_{14} & x_{24} & x_{34} & x_{44} & x_{54} \\ \vdots & \vdots & \vdots & \vdots & \vdots & \vdots \\ 1 & x_{1n} & x_{2n} & x_{3n} & x_{4n} & x_{5n} \end{bmatrix}, B = \begin{bmatrix} \beta_0 \\ \beta_1 \\ \beta_2 \\ \beta_3 \\ \beta_4 \\ \beta_5 \end{bmatrix}$$

The number of columns in the matrix X are dependent on the number of swing parameters 233 analyzed in the regression model. For example, in the above depiction of X, there would be five swing parameters 233 analyzed. The value "n" is indicative of the number of data points (e.g. swings of the reference golf club 250) that are analyzed. Corresponding to those five swing parameters 233, are the values in the vector B. The vector B will always have a number of values equal to the number of swing parameters 233 plus one additional value, $\beta_0$.

Any swing parameters 233 may be utilized for the inputs for X. However, in preferable implementations, the swing parameters 233 utilized in the lie algorithm 243 are impact lie, initial lie, shaft lean, and impact face angle, each of which is described above. These swing parameters 233 have been determined to be indicative of the impact lie angle because they are parameters representative of the swing type and club head position during the swing.

In order to determine the best fit linear model, a large number of data points need to be taken based on the swings of a variety of golfers. Using the data, the regression model can calculate the best fit linear model for the lie fit determination to be output by the lie algorithm 243. Using the preferable implementation described in the preceding paragraph, the regression model would yield that of equation (10) below:

$$Y = \beta_0 + \beta_1 x_1 + \beta_2 x_2 + \beta_3 x_3 + \beta_4 x_4 \qquad (10)$$

where $x_1$, $x_2$, $x_3$, and $x_4$ are the swing parameters 233 impact lie, initial lie, shaft lean, and impact face angle, respectively, and $\beta_0$, $\beta_1$, $\beta_2$, $\beta_3$, and $\beta_4$ are the coefficients utilized to create the best fit for Y, the impact lie calculated by the sensor of the type 152*f*.

The vector of coefficients, B, is calculated using ordinary least squares to solve the above linear system, where the ordinary least squares calculating is done by equation (11) below:

$$B = (X^T X)^{-1} X^T Y \qquad (11)$$

This method finds B such that the squared error is minimized. This method can be utilized for any number of swing parameters 233, higher order terms, and with swing parameter 233 interaction.

Utilizing this method, by way of the lie algorithm 243, in the preferable implementation described above, the following vector of coefficients, B, was calculated:

$$B = \begin{bmatrix} \beta_0 \\ \beta_1 \\ \beta_2 \\ \beta_3 \\ \beta_4 \end{bmatrix} = \begin{bmatrix} -4.23 \\ 0.87 \\ 0.20 \\ -0.09 \\ -0.12 \end{bmatrix}$$

such that:

$$\text{Lie Fit} = -4.23 + 0.87 \ast x_1 + 0.20 \ast x_2 - 0.09 \ast x_3 - 0.12 \ast x_4$$

where Lie Fit is the recommended lie angle adjustment, $x_1$ is the impact lie, $x_2$ is the initial lie, $x_3$ is the shaft lean, and $x_4$ is the impact face angle.

This determination of the lie fit utilizing a regression model is just one example calculated using the lie algorithm 243. Similar to that described above with respect to the shaft algorithm 238, the lie algorithm 243 will be different dependent on the particular golfers tested, the number of golfers tested, the sensors 252 utilized, etc. In addition, as described with respect to the shaft algorithm 238, the lie algorithm 243 may be static, such that the software program 220 includes the lie algorithm 243 and the lie algorithm 243 doesn't change without additional data input, or the lie algorithm 243 may be dynamically updated either locally or universally to reflect additional data inputs from additional swings automatically through the lifetime of the software application 220.

Once the Lie Fit value is generated, the software application 220 displays the Lie Fit value. In some implementations, the Lie Fit value may be displayed directly, such that if the Lie Fit value is 2.3°, that is what the software application 220 displays. However, because there is a margin for error, a club head can only be bent to a certain extent before sacrificing performance and rigidity, adjusting the lie of a golf club head is not overly precise and often done in one degree increments, the lie algorithm 243 may utilize a bin method to output the Lie Fit value.

For one example, the lie algorithm 243 may utilize the following table for bin selections when recommended the Lie Fit value.

| Lie Fit [°] | Recommendation [°] |
|---|---|
| X < −6 | −3 |
| −6 < X < −4 | −2 |
| −4 < X < −2 | −1 |
| −2 < X < 2 | 0 |
| −2 < X < 4 | 1 |
| −4 < X < 6 | 2 |
| X > 6 | 3 | where the Lie Fit is the value calculated by the lie algorithm 243 utilizing the linear regression model, and the recommendation is the lie angle adjustment recommendation output by the software application 220 to the fitter/user of the software application for making adjustments to the club head. It should be noted that any number of swings may be averaged together by the lie algorithm 243 to output the lie recommendation. In some cases, especially with higher handicap golfers, the variations between swings of the reference golf club 250 are greater, and thus the more swings taken the better overall picture of the users swing, and thus the more fitting lie recommendation.

Figure 4C:
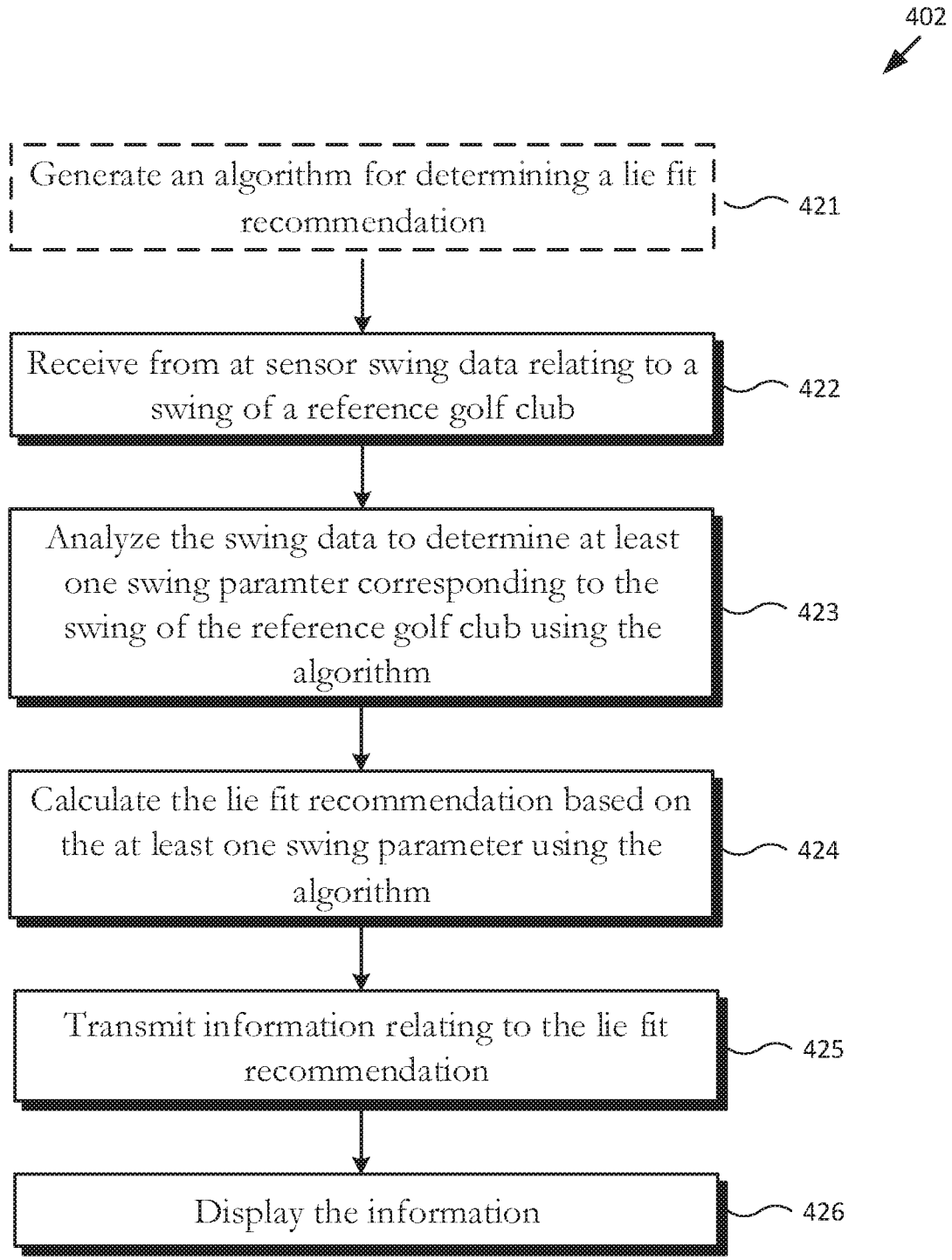
FIG. 4C is another flowchart diagram illustrating a method for use by systems and apparatus of the present disclosure.

Now referring to FIG. 4C, FIG. 4C is a flowchart diagram illustrating a method for use by systems and apparatus of the present disclosure. The approach and technique indicated by flowchart 402 are sufficient to describe at least one implementation of the present disclosure, however, other implementations of the disclosure may utilize approaches and techniques different from those shown in flowchart 402. Furthermore, while flowchart 402 is described with respect to FIGS. 2A-2C, the disclosed inventive concepts are not intended to be limited by specific features shown and described with respect to FIGS. 2A-2C. Furthermore, with respect to the method illustrated in FIG. 4C, it is noted that certain details and features have been left out of flowchart 402 in order not to obscure the discussion of inventive features in the present application.

Flowchart 402 (at 421) includes generating an algorithm for determining a lie fit recommendation. For example, the software application 220*b* on the computing device 210 generates the lie algorithm 243 for providing a lie fit recommendation. In order to generate the lie algorithm 243, the computing device 210 receives sensor data 256*b* from a first sensor 252 of the type similar to sensors 152*a*-152*e* and sensor data 256*b* from a second sensor 252 of the type similar to sensor 152*f*, such as an HMT. The sensor data 256*b* is generated based on at least one swing, and preferably a plurality of swings from a wide range of golfers having varying swing styles and handicaps (skill levels).

The algorithm 236, or the lie algorithm 243, then determines at least one swing parameter 233 from the sensor data 256*b* from the first sensor 252 and at least one swing parameter 233 from the sensor data 256*b* from the second sensor 252.

The computing device 210 then determines a relationship between the at least one swing parameter 233 from the first sensor 252 and the at least one swing parameter from the second sensor 252. As described above, the swing parameters 233 determined from the first sensor 252 may be impact lie, initial lie, shaft lean, and impact face angle and the at least one swing parameter 233 from the second sensor 252 may be impact lie. As such, the lie algorithm 243 determines the relationship between the impact lie, initial lie, shaft lean, and impact face angle determined from the first sensor 252 and the impact lie from the second sensor 252. This may be done using a regression model as outlined above.

Once the relationship is determined, the software application 220 generates the algorithm, which is part of the lie algorithm 243, for outputting a lie fit recommendation based on swing parameter 233 inputs.

By following this method of generating the lie algorithm 243, a fitter is able to utilize a sensor 252 similar to those of sensors 152a-152e (i.e., club attached sensors) to perform fittings with the accuracy of traditional, more expensive, less mobile fitting sensors/systems such as those of sensor 152f (e.g., external sensors detached from the golf club). The generation of the lie algorithm 243 enables calibration of the club attached sensors in view of the sensor data 256 generated by external sensors, which are generally more accurate because they utilize cameras and motion sensors to capture actual locations on the golf club during the swing. However, these external sensors generally require more space, more investment, more hardware/software, and are more onerous to transport from place to place. As such, by calibrating the attached sensors using this method, the space, investment, need for hardware/software, and transportation issues are substantially reduced without sacrificing much in the way of accuracy.

It should be noted that step 421 has a dashed outline indicating that the generation of an algorithm is not a required step each time. For example, for a static lie algorithm 243, where there is no dynamic updating, the lie algorithm 243 may already be programmed into the software application 220, or in some cases, the lie algorithm 243 may not include this calibration method.

Flowchart 402 (at 422) includes receiving, from a sensor, swing data relating to a swing of a reference golf club. For example, the computing device 210 receives sensor data 256 relating to a swing of the reference golf club 250. The sensor data 256 may be received by the computing device 210 or by the server 270, or by both, depending on the implementation.

Flowchart 402 (at 423) includes analyzing the swing data to determine at least one swing parameter corresponding to the swing of the reference golf club using the algorithm. For example, the sensor data 256 is analyzed to determine at least one swing parameter 233, such as impact lie, initial lie, shaft lean, or impact face angle. This is done using the algorithm 236, or lie algorithm 243, depending on the implementation.

Flowchart 402 (at 424) includes calculating the lie fit recommendation based on the at least one swing parameter using the algorithm. For example, the at least one swing parameter 233 is input into the lie algorithm 243 to output a lie fit recommendation. The lie fit recommendation may be the actual club lie that is recommended, such as 61°, or may be the amount the club lie needs to be adjusted, such as −2° if the club lie is currently 63° and the recommended lie is 61°.

Flowchart 402 (at 425) includes transmitting information relating to the lie fit recommendation. For example, the computing device 210 may transmit the information to the display 238 or, in some implementations, the server 270 may transmit the information to the computing device 210 which is then transmitted to the display 238.

Flowchart 402 (at 426) includes displaying the information. For example, the information is displayed on the display 238 of the computing device 210.

Traditionally lie angle adjustments were completed using lie boards on the ground which indicate lie angle issues and provide recommended changes based on indicators on the board, or lie angle adjustments were made based on estimates from sensor equipment using generic information, such as a generic club lie. In such traditional approaches, the accuracy is skewed because different clubs have different lie angles, and the systems didn't account for that. In addition, lie boards are imprecise because for some players a large portion of the sole of the club head makes contact with the board, requiring the fitter to estimate or guess which location on the sole of the club head made contact with the lie board first. Also, and especially, club attached sensors have never been utilized for outputting lie angle recommendations, and especially not lie fit recommendations where the actual change in lie angle to be made is provided. The method described above with respect to flowchart 402 provides an actual lie fit recommendation, which is the amount of adjustment needed, and factors in the current lie angle of the club head based on stored information on the computing device 210 in the database 226. In addition, this method allows for a club attached sensor 252 (e.g., sensor 152a-152e) to generate not only recommended lie angles, but can allow for lie fit recommendations that output the exact change in lie angle needed for that specific club.

It should be noted that algorithm 236, shaft algorithm 238, and lie algorithm 243 may all be part of the same algorithm, or may each be separate algorithms. For example, the algorithm 236, the shaft algorithm 238, and the lie algorithm 243 may each be a part of one algorithm. In such an example, the algorithm 236 may be utilized to calculate the swing parameters 233 from the sensor data 256. The shaft algorithm 238 may then utilize the swing parameters 233 calculated by the algorithm 236 to determine the best fit linear models between swing parameters 233 and shaft parameters 240 such that the shaft algorithm 238 can calculate recommended values 242 for the shaft parameters 240. In this example, the algorithm 236 and the shaft algorithm 238 comprise one total algorithm that ultimately enable the sensor data 256 to be converted to recommended values 242 for shaft parameters 240. The shaft algorithm 238 then utilizes the recommended values 242 to recommend at least one of the shafts 231 to the user 202 based on comparisons between actual values 241 and recommended values 242 of the shaft parameters 240, whereby the comparison is based on distance 238, as described above.

It should be noted that the software application discussed with reference to FIGS. 3A-3C corresponds to the software application 220b and 220c of FIGS. 2A, 2B, and 2C.

Figure 3A:
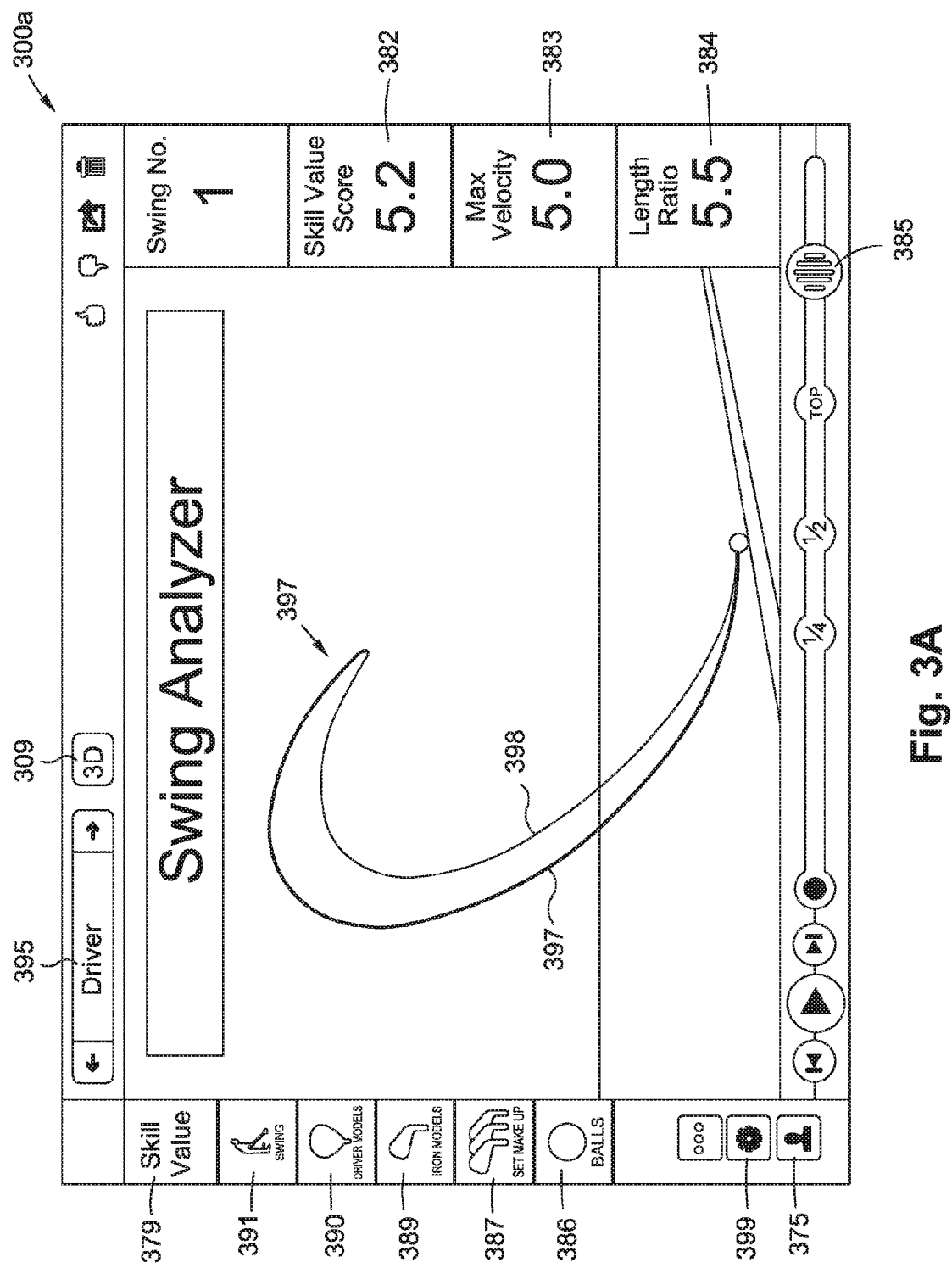
FIG. 3A is an illustration of a display of a software application for analyzing a sporting apparatus, according to one implementation of the present disclosure.

Now referring to FIG. 3A, FIG. 3A illustrates a display of a software application for analyzing a sporting apparatus, according to one implementation of the present disclosure. Display 300a of FIG. 3A includes reference golf club 395, swing value tab 379, swing analyzer tab 391, driver models tab 390, iron models tab 389, set make up tab 387, ball tab 386, settings tab 399, user tab 375, skill value display 382, max velocity display 383, length ratio display 384, swing path 396, backswing segment 397, downswing segment 398, swing view 309, and swing view playback 385.

Figure 3B:
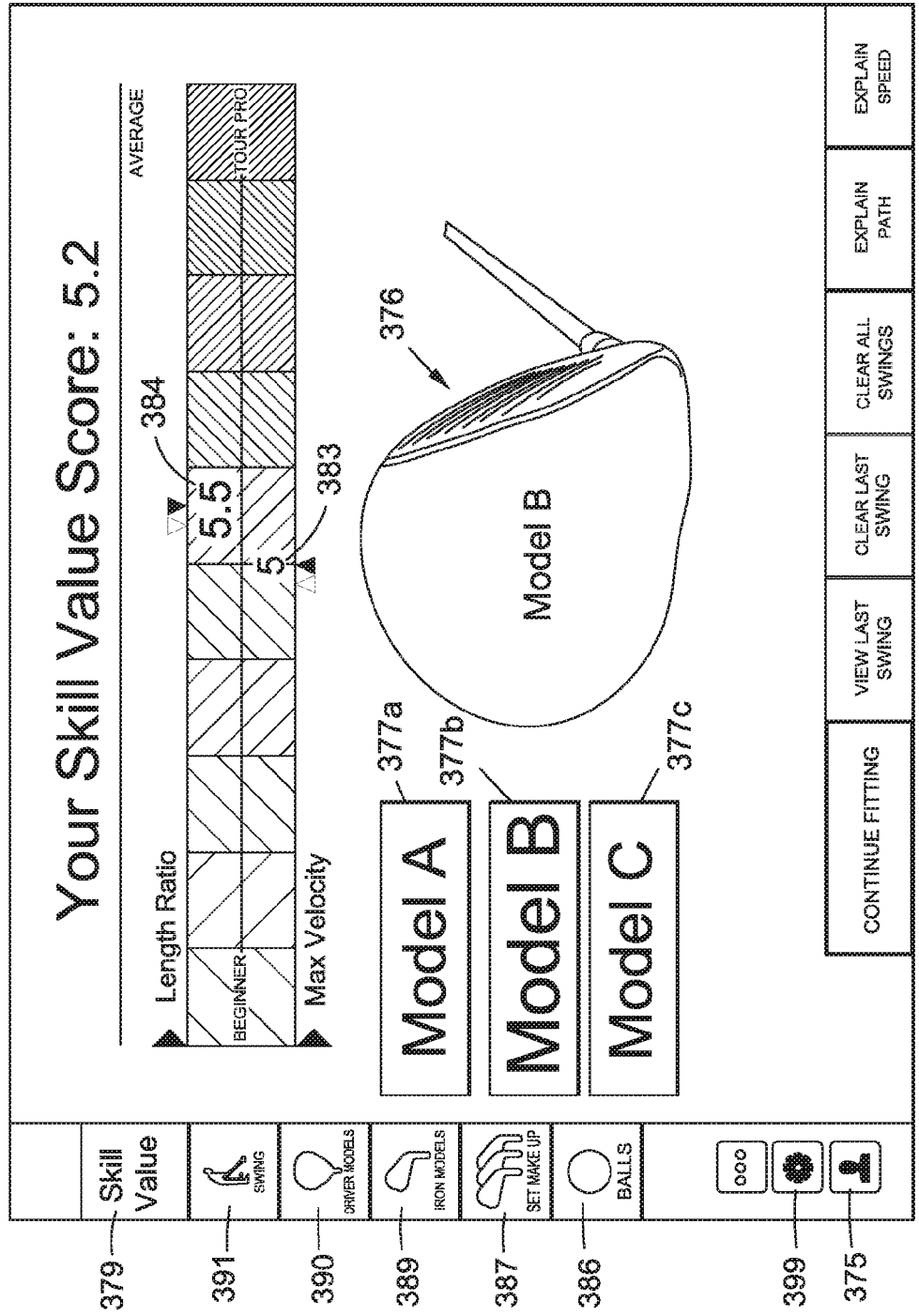
FIG. 3B is an illustration of another display of the software application for analyzing a sporting apparatus of FIG. 3A, according to one implementation of the present disclosure.

The swing value tab 379, when selected, is configured to open another display of the software application, which is described in further detail with respect to FIG. 3B.

Figure 3C:
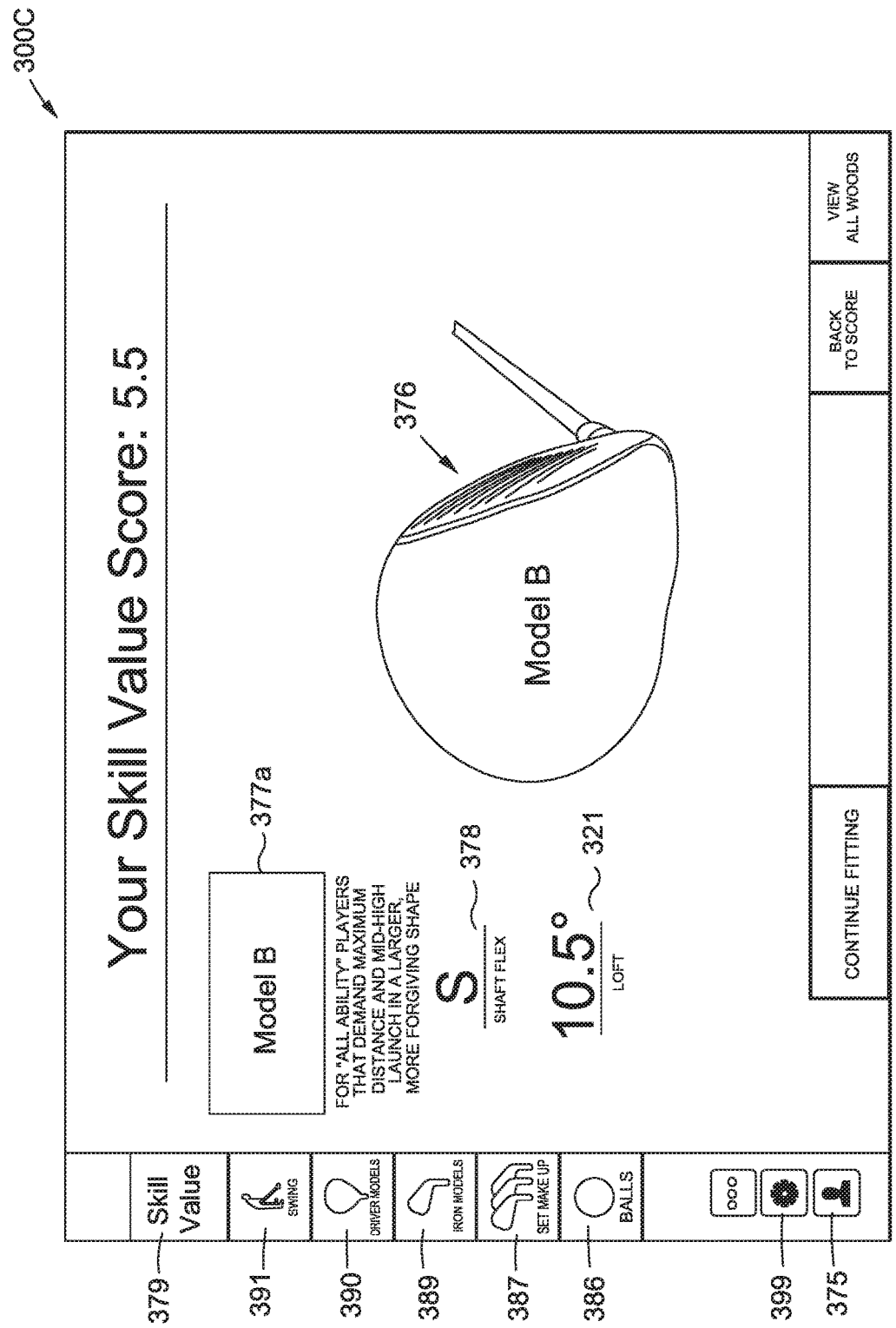
FIG. 3C is an illustration of another display of the software application for analyzing a sporting apparatus of FIGS. 3A and 3B, according to one implementation of the present disclosure.

The driver models tab 390, when selected, is configured to open another display of the software application, which is described in further detail with respect to FIG. 3C.

The iron models tab 389, when selected, is configured to open another display for the software application for viewing recommended iron models. For example, where the reference golf club 395 is an iron type golf club, the software application may recommend the iron type golf clubs based on the sensor data collected and the swing parameters. In examples where the reference golf club 395 selected is not an iron type golf club, but a driver, for example, the iron models tab 389 may still provide recommendations of iron type golf clubs based on the swing parameters of the swing with the driver. For example, if the software application recommends a driver for game-improvement type player having skill values ranging from 1-3, the iron type golf clubs recommended on the display of the iron models tab 389 may include irons that also include skill values ranging from 1-3.

The set make up tab 387, when selected, is configured to open another display of the software application for viewing recommended set make ups. Similar to the iron models tab 389, described above, the software application may recommend not only the golf club determined based on the reference golf club 395 type, but also the additional clubs necessary to complete, or at least partially complete, a set of golf clubs. For example, if the reference golf club 395 is a driver, and the software application recommends a driver for skill values ranging from 1-3, the software application may also generate a set of fairway woods, irons, hybrids, and wedges designed for players of skill values ranging from 1-3, such as the golf clubs 228 having the golf club skill values 227 ranging from 1-3 of FIG. 2A. In addition to recommending the different club types, the software application may be configured to determine and recommend a set make-up. For example, the application may be configured to recommend how many wedges the user should have. Also, as an example, the application may be configured to recommend how many hybrids and/or irons are necessary for players having the skill values and swing parameters of the user swinging the reference golf club. For example, players with very low skill values, around 1-3, may benefit from having hybrids in place of their 3, 4, 5, and 6 irons because hybrids are characteristically easier to hit, while players with higher skill values, around 3-5, may only require a 3 and 4 hybrid, because players of those skill values may be more capable of hitting a 5 or 6 iron.

The ball tab 386, when selected, is configured to open another display of the software application for viewing recommended balls. The software application may display each of the balls available with a description of the balls, allowing the player to choose based on descriptions. However, the software application may be configured to utilize the impact conditions measured by a club attached sensor, such as the sensor 152a of FIG. 1, or impact conditions measured by a golf ball sensor, such sensor 104 of FIG. 1, to recommend a ball. For example, if the impact conditions show high values of side spin, the software application may recommend a ball that produces less spin. For another example, the software application may utilize the skill value 237 to determine balls that are recommended for players having a skill value 237 of the user.

The setting tab 399, when selected, is configured to open another display of the software application for viewing and/or altering the settings of the software application, the computing device, and the sensor. For example, the user of the software application may be able to change the settings of the reference golf club 395 and/or the sensor attached to the reference golf club, such as the sensor settings 258a of the sensor 252 of FIG. 2A. In addition, the location, time, date, battery, brightness, and other settings of the software application and the computing device operating the software application may be viewed and/or changed in the setting tab 399. The location, for example, may change the recommended golf clubs in the driver models tab 390, the iron models tab 389, and the set make up tab 387, in addition to the balls in the ball tab 386 to only display golf clubs and balls that are available in that location.

The user tab 375, when selected, is configured to open another display of the software application for viewing and/or changing the user data. The user data, such as the user data 235 of FIG. 2A, can be changed and viewed in the user tab 375. For example, if the user of the software application updates the data of the user of the reference golf club, such as the reference golf club 250 in FIG. 2A, the updated user data can be transmitted to the sensor, such as sensor 252 of FIG. 2A, in order to calculate more accurate results.

The swing analyzer tab 391, when clicked, is configured to open the display 300a on the computing device, such as the computing device 110 of FIG. 1.

The display 300a includes the reference golf club 395 that includes the type of golf club having the attached sensor, such as reference golf club 250 and sensor 252 of FIG. 2A. The software application may include any number of available options for the reference golf club 395, and each of the reference golf clubs 395 may include any number of characteristics. For example, when a user of the software application selects the reference golf club 395, the software application may transmit the characteristics of the reference golf club 395 to the sensor attached to the reference golf club, such as one of sensors 152 attached to the reference golf club 150 in FIG. 1.

The display 300a further includes the skill value display 382. The skill value display 382 is configured to display the skill value, such as the skill value 237 based on the algorithm 236 of FIG. 2A. The skill value may be normalized to fall within a specified range, as described in more detail above with respect to FIG. 2A. In the illustrated display 300a of FIG. 3A, the skill value display 382 includes the skill value of 5.2 which is a rounded average of the max velocity and length ratio displayed in the max velocity display 383 and the length ratio display 384, respectively.

The display 300a further includes the max velocity display 383. The max velocity display 383 is configured to display the maximum velocity, such as the maximum velocity from the swing parameters 233 of FIG. 2A. The maximum velocity may be normalized to fall within a specified range, as described in more detail above with respect to FIG. 2A.

The display 300a further includes the length ratio display 384. The length ratio display 384 is configured to display the length ratio, such as the length ratio from the swing parameters 233 of FIG. 2A. The length ratio may be normalized to fall within a specified range, as described in more detail above with respect to FIG. 2A.

It should be noted that although the display 300a includes only the max velocity display 383 and the length ratio display 384, any other swing parameters and/or data, such as the swing parameters 233 and data 224 of FIG. 2A, may also be included in the display 300a. For example, in some implementations, the swing parameters and data used in calculating the skill value may be the swing parameters and data displayed on display 300a.

The display 300a includes the swing path 396 having the backswing segment 397 and the downswing segment 398. The swing path 396 is generated from tracking the orientation, location, and velocity in 2D and/or 3D space of a location on the reference golf club throughout a swing of the reference golf club, such as reference golf club 150 of FIG. 1. Visualizing the swing path 396 on the display allows the user of the software application to analyze the swing, and also provides visual feedback to the user of the reference golf club as to the swing parameter values, including the length ratio and the maximum velocity, for example, and ultimately feedback on the calculated skill value.

The display 300a also includes the swing view 309 that when selected is configured to allow the user of the software application to view the swing path 396 in different orientations and dimensions. For example, the swing view 309 may allow the user to select between 2D and 3D, viewing of the swing path 396, or to change the orientation to a rear, side, top, or front view of the swing path 396.

The swing path 396 may also be illustrated in an environment that provides depth and clarity for analyzing the swing path 396, such as in a clean room type environment, as illustrated in FIG. 3A. The depth and clarity of the environment allow the user to more noticeably identify the characteristics of the swing path 396, especially when displayed in 3D space, on the display.

The software application is further enabled to allow a user to manually manipulate the swing path 396 by zooming in, zooming out, and rotating the swing path 396, for example, using an input device such as a mouse or keyboard, or by using finger gestures on a touch-screen display of the device operating the software application, such as the display 238 of the computing device 210 in FIG. 2A.

The display 300a further includes the swing view playback 385 configured to allow user control of playback, fast-forward, rewind, stop, and pause the swing path 396 on the display. For example, in FIG. 3A the entire swing path 396 is shown, including the backswing segment 397 and the downswing segment 398, but the swing view playback 385 is configured to display the swing path 396 as it was/is created during a swing of the reference golf club, such as reference golf club 150 of FIG. 1. The swing view playback 385 includes selectable locations in the swing path 396 including the ¼ swing location, the ½ swing location, and the top swing location, for example. The ¼ swing location is when the reference golf club shafts longitudinal axis is substantially parallel to the ground plane during the backswing segment 397, the ½ swing location is when the reference golf club shafts longitudinal axis is substantially perpendicular to the ground plane, and the top swing location is when the reference golf club reverses direction. As such, the user of the software application is able to quickly navigate to the specific locations within the swing path 396 for analysis.

Now referring to FIG. 3B, FIG. 3B is an illustration of another display of the software application for analyzing a sporting apparatus of FIG. 3A, according to one implementation of the present disclosure. The display 300b of FIG. 3B includes the swing value tab 379, swing analyzer tab 391, driver models tab 390, iron models tab 389, set make up tab 387, ball tab 386, settings tab 399, user tab 375, skill value display 382, max velocity display 383, length ratio display 384, model 377a, model 377b, model 377c (hereinafter referred to collectively as models 377), and recommended golf club 376. It should be noted that the swing value tab 379, swing analyzer tab 391, driver models tab 390, iron models tab 389, set make up tab 387, ball tab 386, settings tab 399, user tab 375, skill value display 382, max velocity display 383, length ratio display 384 of FIG. 3B correspond respectively to the swing value tab 379, swing analyzer tab 391, driver models tab 390, iron models tab 389, set make up tab 387, ball tab 386, settings tab 399, user tab 375, skill value display 382, max velocity display 383, length ratio display 384 of FIG. 3A.

The length ratio display 384 and the max velocity display 383 of display 300b include a scale, where each of the triangles represent the length ratio and the maximum velocity for each swing, and the displayed value is an average of the all of the swings. The scale may range between the normalized values of the length ratio and the maximum velocity, from 0-10, as an example. In one example, a first swing may be taken with the reference golf club, such as reference golf club 150 of FIG. 1, and the length ratio and the maximum velocity may be calculated and normalized and then indicated in display 300b with a white triangle. A second swing may then be taken, with the maximum velocity and the length ratio indicated in display 300b by black triangles, and so on. In some implementations, the most recent swing may be indicated by a black triangle, while all prior swings are indicated by triangles of like color, such as white, for example. For each additional swing, the average value of the length ratio and the maximum velocity is dynamically updated in the length ratio display 384 and the max velocity display 383, respectively. As a result, the skill value display 382 reflects the updated average of the maximum velocity and the length ratio after each swing.

The display 300b further includes the models 377. The models 377 may include all available models for the user of the reference golf club, or may include only the models having golf club skill values closest to the skill value calculated by a swing of the reference golf club by the user. For example, if the user is looking to find a recommended driver, and they are right handed, and located in the United States, the software application may only display the models 377 that are available to the user and display the models, such as illustrated in display 300b. Once the user takes a swing, or a plurality of swings, with the reference golf club, the skill value updates and the model with the closest golf club skill value to the updated skill value is recommended. The recommendation may be displayed by, for example, bolding, highlighting, italicizing, enlarging, or otherwise alternating the appearance of the name of the model in comparison to the other listed models, and/or by displaying the model on the screen. The display 300b provides an example illustrating the model 377b as bolded and enlarged relative to models 377a, 377c, and by displaying the recommended golf club 376.

After a number of swings, the skill value may update, and the recommended golf club 376 may change, and the change is then reflected on the display similar to above. For example, the skill value after two swings may be 5.3, and the model 377b may be recommended based on its golf club skill value range being between 5 and 6.9. After fifteen swings, the skill value may change to 3.9, and as a result the model 377a may be recommended based on its golf club skill value of 3 to 4.9. As such, the display 300b is configured to dynamically update with each new swing of the reference golf club.

Now referring to FIG. 3C, FIG. 3C is an illustration of another display of the software application for analyzing a sporting apparatus of FIGS. 3A and 3B, according to one implementation of the present disclosure. The display 300c of FIG. 3C includes the swing value tab 379, swing analyzer tab 391, driver models tab 390, iron models tab 389, set make up tab 387, ball tab 386, settings tab 399, user tab 375, skill value display 382, model 377b, recommended golf club 376, shaft properties 378, and loft 321. It should be noted that the swing value tab 379, swing analyzer tab 391, driver models tab 390, iron models tab 389, set make up tab 387, ball tab 386, settings tab 399, user tab 375, skill value display 382, recommended golf club 376, and model 377b of FIG. 3C. correspond respectively to the swing value tab 379, swing analyzer tab 391, driver models tab 390, iron models tab 389, set make up tab 387, ball tab 386, settings tab 399, user tab 375, skill value display 382, recommended golf club 376, and model 377b of FIG. 3B.

Once the model 377b and the recommended golf club 376 are determined, the shaft properties 378 and the loft 321 can further be displayed, along with other club head properties. The shaft properties 378 may include the flex, the flex profile, the length, the balance point, the kick point, the model, or the manufacturer. The shaft properties 378 are recommended based on the swing parameters, the sensor data, and the recommended golf club, as discussed in further detail above with respect to the FIG. 2A.

The loft 321 is displayed in FIG. 3C, but other club head properties that may be displayed include lie, weight adjustability, and/or other features relating to the club head of the recommended golf club 376.

It should be noted with respect to FIG. 3B and FIG. 3C that more than one golf club and/or model, shaft, ball, shaft properties 378, and/or club head properties can be recommended in addition to loft 321.

Figure 3D:
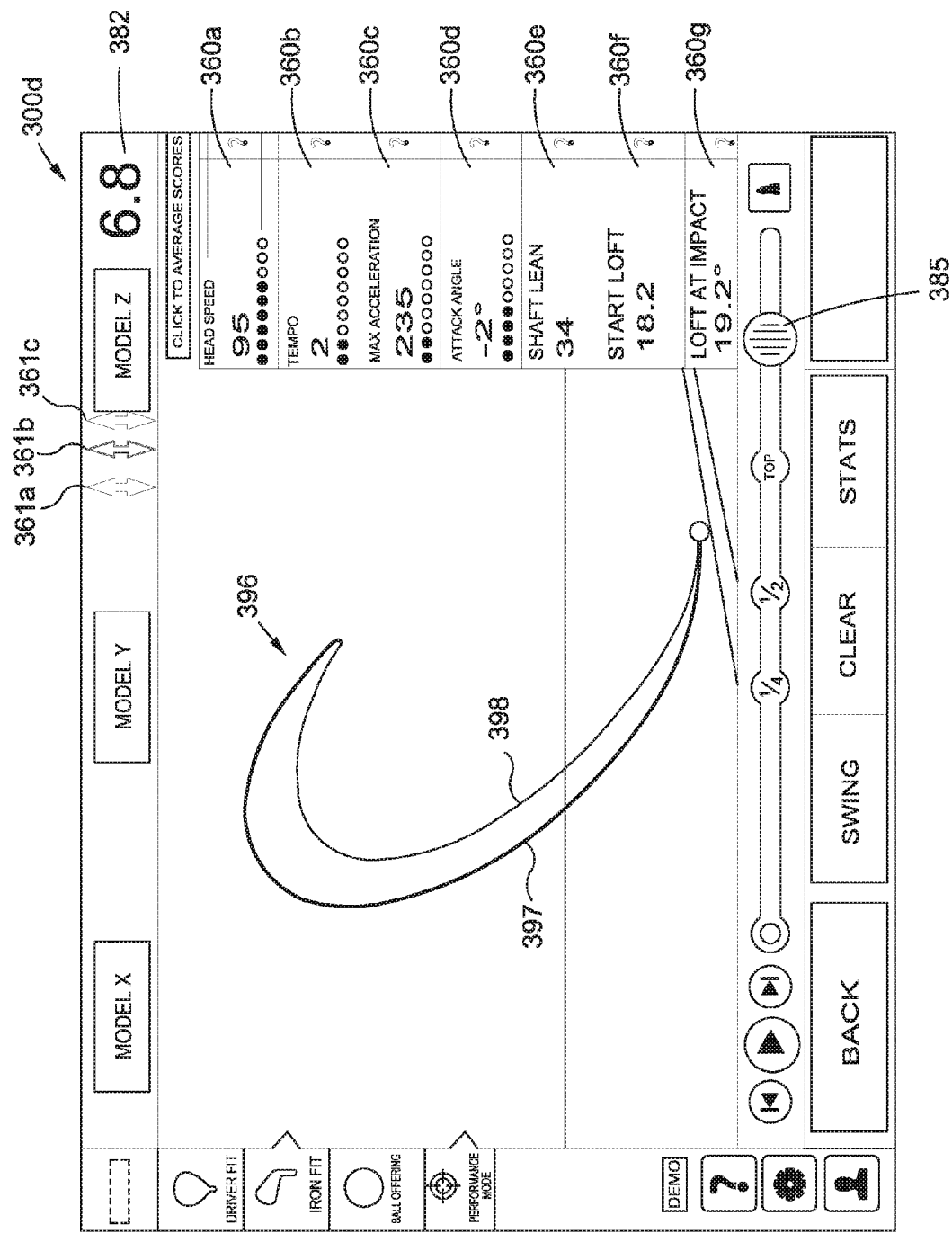
FIG. 3D is an illustration of another display of the software application for analyzing a sporting apparatus of FIGS. 3A-3C, according to one implementation of the present disclosure.

FIG. 3D is an illustration of another display of the software application for analyzing a sporting apparatus of FIGS. 3A-3C, according to one implementation of the present disclosure. Display 300d of FIG. 3D includes a display of a plurality of swing parameter 233, including the maximum club head speed 360a, the tempo 360b, the maximum tangential acceleration 360c, the attack angle 360d, the shaft lean 360e, the initial loft 360f, and the impact loft 360g. Each of these swing parameter 233 is described above. Displaying the swing parameters 233 allows the fitter and the user to see what factors are being considered in recommending the skill value score, the shaft recommendation, and the lie fit recommendation, for example.

The display 300d also includes the skill value display 382. Next to the skill value display 382 is a swing identification bar that includes three swings, 361a, 361b, and 361c as examples of where the skill value score lines up on the swing identification bar. The swing identification bar also includes a listing of the available golf club models that are being fitted for, in this case, Model X, Model Y, and Model Z. Each swing is located on the swing identification bar according to the skill value score. In display 300d, for example, the three swings, 361a, 361b, and 361c average out to 6.8, and thus are closer to the Model Z, which is recommended to players having a skill value score closer to 7, for example. If the user had a skill value score closer to 3, the user may be recommended Model X, for example, and the users swings would show up on the swing identification bar closer to Model X.

Figure 3E:
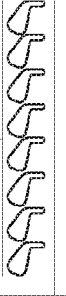
FIG. 3E is an illustration of another display of the software application for analyzing a sporting apparatus of FIGS. 3A-3D, according to one implementation of the present disclosure.

FIG. 3E is an illustration of another display of the software application for analyzing a sporting apparatus of FIGS. 3A-3D, according to one implementation of the present disclosure. Display 300e of FIG. 3E includes the skill value display 382, loft display 321, which is a recommendation of the loft of the recommended club. This is most relevant to drivers, which are generally lofted between 7.5° and 12.5°.

A lie fit recommendation 322 is also included in display 300e. The lie fit recommendation 322, as described above with respect to FIGS. 2A-2C, is the recommended lie angle adjustment for the recommended golf club. In the display 300e, the lie fit recommendation 322 is 1°, meaning that the recommended club should be bent 1° to fit the recommended lie angle.

The display 300e also includes the model 365. The model 364 is the recommended club model. As previously stated, the model may be Model A, Model B, or Model C, for example. In the display 300e, the models 364 are the Z565 driver and the Z765 irons, made by Srixon™.

The display 300e also includes the IFC 363. The IFC 363 is the IFC recommendation for the shaft, which is only for graphite type shafts, primarily for drivers and woods. The IFC calculation is described above.

The display 300e also includes the shaft recommendation 362. The shaft recommendation 362 is the shaft recommended based on the swings of the reference golf club, such as reference golf club 250 of FIGS. 2A-2C. The shaft recommendation 362 is generated by the shaft algorithm 238 explained above with respect to FIGS. 2A-2C.

The display 300e also includes the set makeup recommendation 365, which, based on the swings of the user, is generated to recommend the types of clubs recommended for a full set for that type of golfer, with that skill level. This is similar what may be displayed by selecting the set make up tab 387 of FIG. 3B.

Figure 3F:
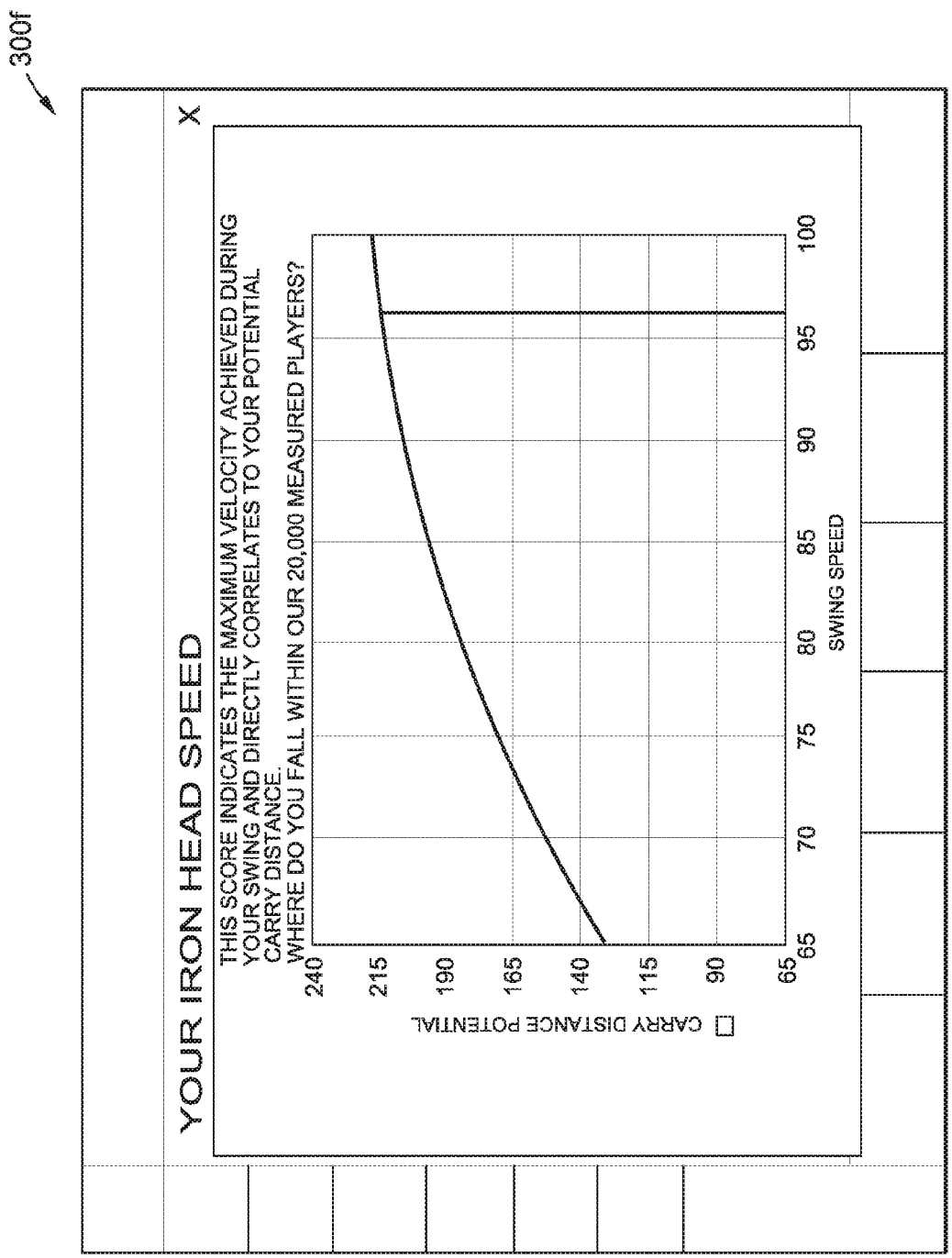
FIG. 3F is an illustration of another display of the software application for analyzing a sporting apparatus of FIGS. 3A-3E, according to one implementation of the present disclosure.

FIG. 3F is an illustration of another display of the software application for analyzing a sporting apparatus of FIGS. 3A-3E, according to one implementation of the present disclosure. Display 300f of FIG. 3F displays a chart of estimated carry distance vs. swing speed. The sensor, such as sensor 152, measures the swing speed of the golfer, and based on player testing and data, the software application predicts the carry distance potential for that golfer, as indicated by the vertical line between the 95 and 100 swing speed values. This particular chart is for an iron, but can also be scaled for drivers, or any other club in the set.

Figure 3G:
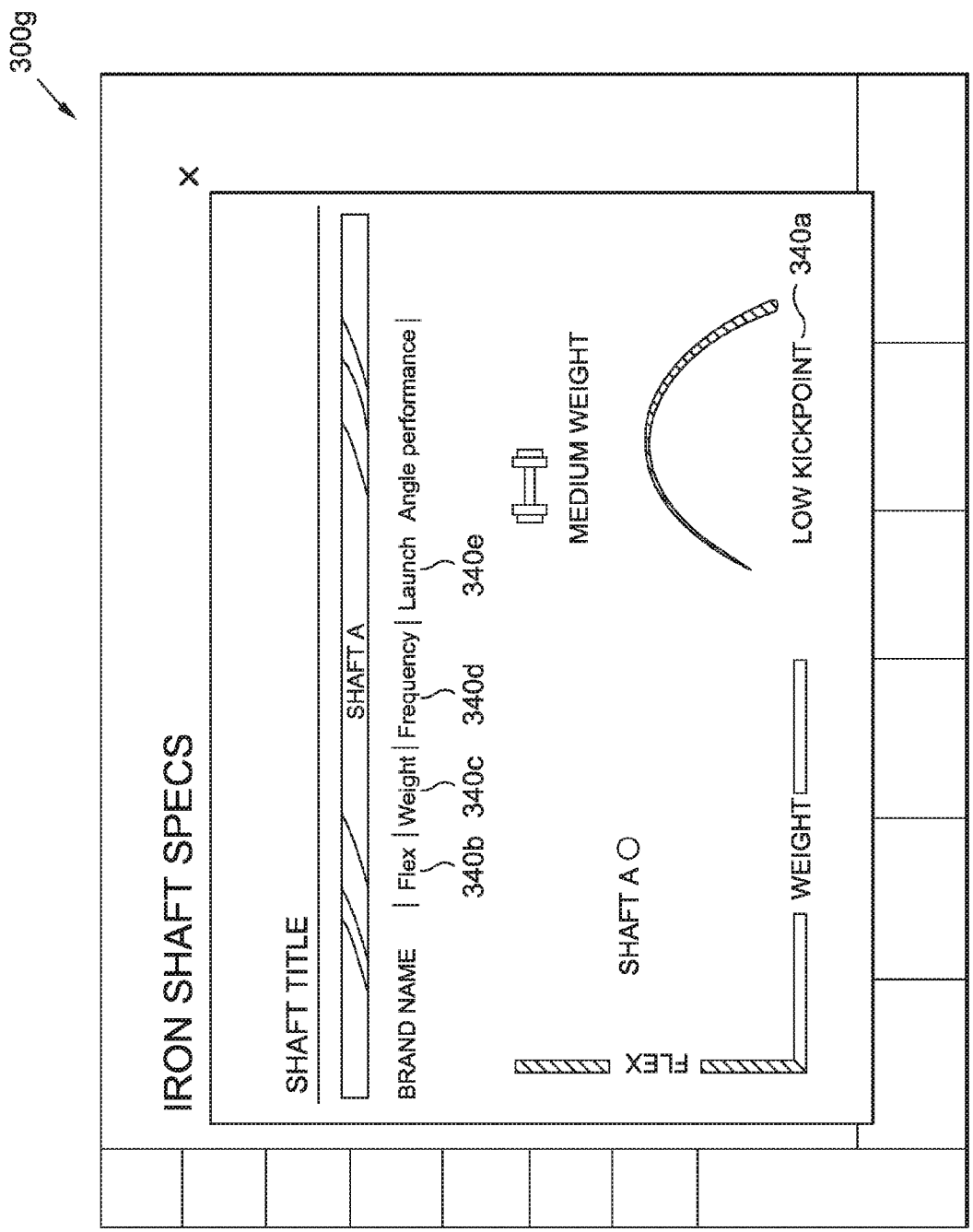
FIG. 3G is an illustration of another display of the software application for analyzing a sporting apparatus of FIGS. 3A-3F, according to one implementation of the present disclosure.

FIG. 3G is an illustration of another display of the software application for analyzing a sporting apparatus of FIGS. 3A-3F, according to one implementation of the present disclosure. Display 300g of FIG. 3G includes a plurality of shaft parameters 340, including shaft kick point 340a, shaft flex 340b, shaft weight 340c, shaft frequency 340d, and shaft launch angle performance 340e. Any shaft parameters may be displayed here, including each of the shaft parameters 240 described above with respect to FIGS. 2A-2C. The display 300g also includes an image of the shaft and the shaft model, including brand name and specific model within the brand. The display 300g further includes a chart comparing the shaft weight to the shaft flex, which is a comparison between two shaft parameters to provide an overall idea of the shaft characteristics in view of shaft flex and shaft weight. However, other shaft parameters could be analyzed in comparison to each other, such as shaft weight and shaft kick point, for example, to give a visual display of the shaft parameters and a general indication of the overall shaft feel and performance for a given golfer.

Figure 3H:
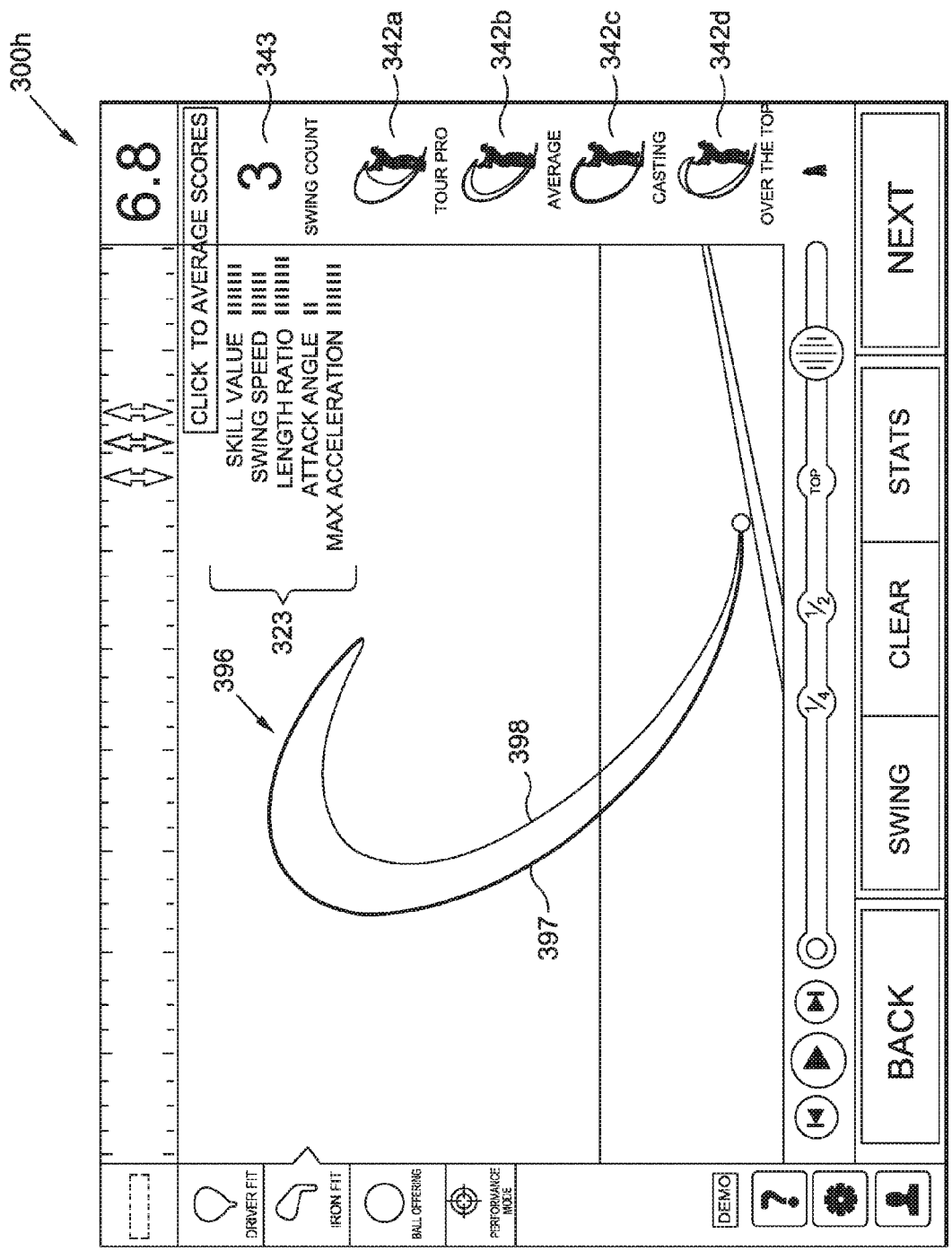
FIG. 3H is an illustration of another display of the software application for analyzing a sporting apparatus of FIGS. 3A-3G, according to one implementation of the present disclosure.

FIG. 3H is an illustration of another display of the software application for analyzing a sporting apparatus of FIGS. 3A-3G, according to one implementation of the present disclosure. Display 300h of FIG. 3H includes a comparative display 323 of the skill value score and swing parameters and corresponding measures of how the skill value score and the swing parameters compare to other golfers, on a scale from bad to good. In the display of 300h, the skill value score, the swing speed, the length ratio, and the maximum acceleration are all relatively high, meaning compared to the hundreds or thousands of swings recorded, the user is near the top. However, the attack angle is low, meaning, compared to the hundreds or thousands of swing recorded, the user has an attack angle that is indicative of a less than ideal attack angle. For each user of the software application, these comparative displays will change depending on the swing.

The display 300h also includes the swing count 343. This is the number of swings that the user has taken that are being used as inputs to calculate the data. The data is then averaged, and output in the comparative display 323.

The display 300h also includes the swing indicators 342, including the tour pro swing indicator 342a, the average swing indicator 342b, the casting swing indicator 342c, and the over the top swing indicator 342d. The swing indicators 342, when selected, display individually or overlay a swing path corresponding to that type of swing into the display. If overlaid, the swing path is overplayed onto the users swing path 396 so the user can visualize what is good or bad about their swing in view of the swing indicator.

For example, if the tour pro swing indicator 342*a* is selected, a swing path of a tour pro is displayed and/or overlaid in the display 300*h*. This allows the user to visualize what a tour pros swing looks like either standing alone, or in view of their swing path 396. The same process is used for the other swing indicators 342.

Figure 3I:
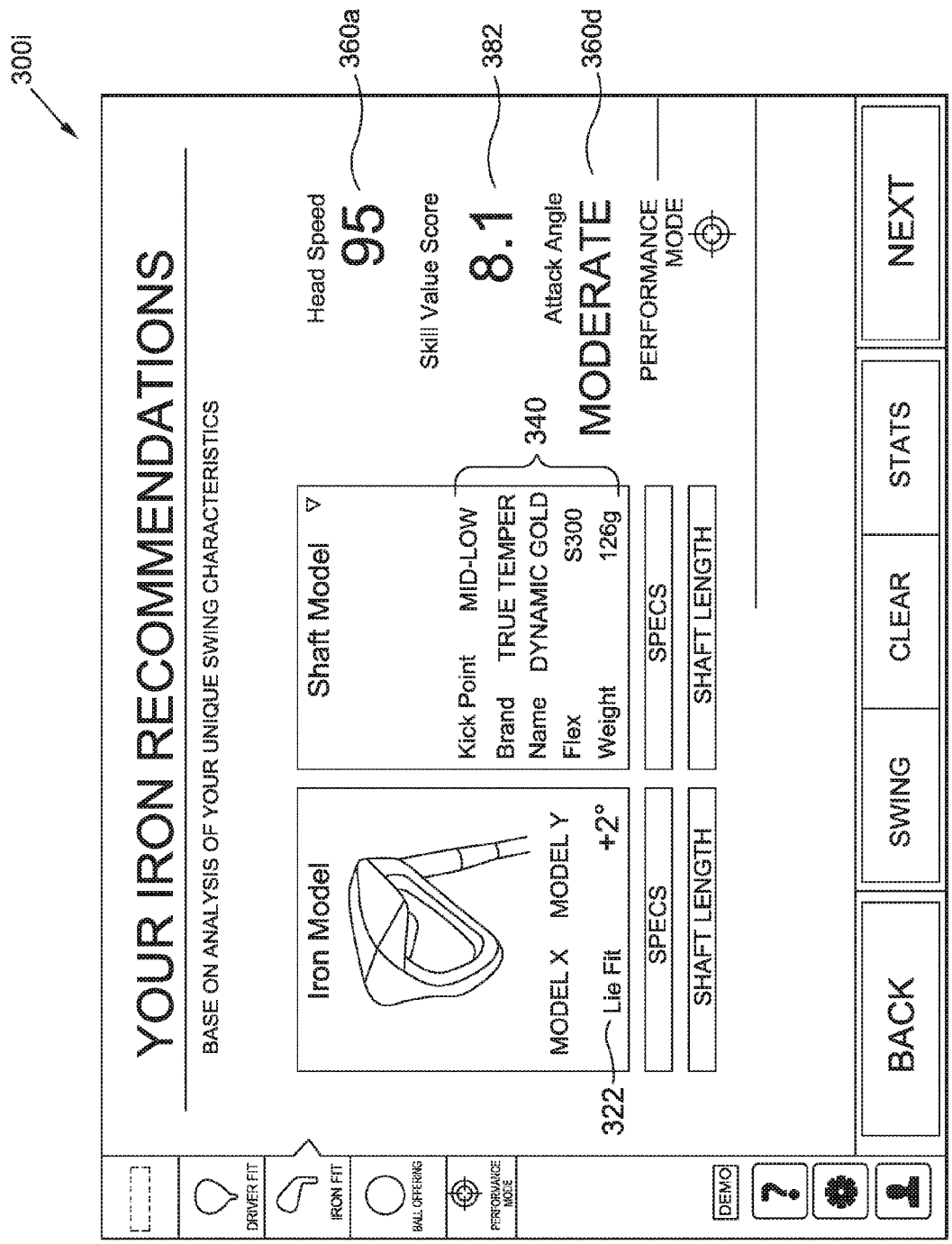
FIG. 3I is an illustration of another display of the software application for analyzing a sporting apparatus of FIGS. 3A-3H, according to one implementation of the present disclosure.

FIG. 3I is an illustration of another display of the software application for analyzing a sporting apparatus of FIGS. 3A-3H, according to one implementation of the present disclosure. Display 300*i* of FIG. 3I includes an overview of the recommendations for the user. In order to generate this overview, the algorithm 236, the shaft algorithm 238, and the lie algorithm 243, as described above with reference to FIGS. 2A-2C, generate the results using the sensor data 256 from the users swing(s). For example, the display 300*i* includes the iron model, which is output by the algorithm 236. The iron model includes a lie fit recommendation 322 which is output by the lie algorithm 243. And the shaft model is displayed along with a plurality of shaft parameters 340 which are generated by the shaft algorithm 238. The overview of display 300*i* also includes swing parameters 233 generated by the algorithm 236, such as head speed 360*a* and attack angle 360*d*, in addition to the output of the skill value score 382. This overview give a full view of the recommendations made by the software application in view of the users swing(s) side by side with important swing parameters generated in response to the users swing(s).

Now referring to FIG. 4, FIG. 4 is a flowchart diagram illustrating a method for use by systems and apparatus of the present disclosure. The approach and technique indicated by flowchart 400 are sufficient to describe at least one implementation of the present disclosure, however, other implementations of the disclosure may utilize approaches and techniques different from those shown in flowchart 400. Furthermore, while flowchart 400 is described with respect to FIGS. 2A-2B, the disclosed inventive concepts are not intended to be limited by specific features shown and described with respect to FIGS. 2A-2C. Furthermore, with respect to the method illustrated in FIG. 4, it is noted that certain details and features have been left out of flowchart 400 in order not to obscure the discussion of inventive features in the present application.

Flowchart 400 will be described with respect to two implementations, implementation A and B. This is in no way to provide limitation, but only to explain two possible implementations of the present disclosure. Implementation A does not include the use of the server 270, while implementation B includes the use of the server 270.

Flowchart 400 (at 410) includes receiving data generated in response to a motion of a sporting apparatus. For example, with regards to implementation A, the computing device 210 may receive the sensor data 256*a* and the sensor settings 258*a* from the sensor 252 across the network 290, such as a Bluetooth™ network, in response to a swing of the reference golf club 250.

For another example, with regards to implementation B, the server 270 may receive the sensor data 256*a* and the sensor settings 258*a* from the sensor 252 over the network 290, such as a WAN, in response to a swing of the reference golf club 250. However, in some implementations, the computing device 210 may first receive the sensor data 256*a* and the sensor settings 258*a* from the sensor 252 over the network 290, such as a ZigBee™ network, and then transmit the sensor data 256*b* and the sensor settings 258*b* to the server 270 over the network 290, such as a WAN.

Referring again to flowchart 400, flowchart 400 (at 420) includes analyzing the data to determine a skill value. For example, with regard to implementation A, the software application 220*b* may first utilize the sensor data 256*b* and the sensor settings 258*b* to calculate the swing parameters 233, such as length ratio and maximum velocity. The software application 220*b* may then be configured to normalize the computed swing parameters 233, and input the swing parameters 233 into the algorithm 236 to determine the skill value 237.

Another example, with regard to implementation B, includes the software application 220*c* on the server 270 first utilizing the sensor data 256*b* and the sensor settings 258*b* to calculate the swing parameters 233, such as length ratio and maximum velocity. The software application 220*b* may then be configured to normalize the computed swing parameters 233, and input the swing parameters 233 into the algorithm 236 to determine the skill value 237. However, in some implementations, the computing device 210 may first utilize the sensor data 256*b* and the sensor settings 258*b* to calculate the swing parameters 233 and ultimately the skill value 237, and then transmit the skill value 237 to the server 270 for use in the next step of determining a recommended sporting apparatus.

Flowchart 400 continues (at 430) with determining a recommended sporting apparatus from a group of at least two sporting apparatuses based on the skill value. For example, with regards to implementation A, the recommendation engine 225 may determine at least one of the golf clubs 228, the shafts 231, and the balls 233 from the database 226 based on a match between the skill value 237 and the golf club skill value 227. However, the recommendation engine 225 may utilize any of the skill value 237, the swing parameters 233, or the sensor data 256*b* to determine the recommended golf clubs 228, shafts 231, and balls 233, in addition to the models 229 and properties 230 of the golf clubs 228, as well as the properties 232 of the shafts 231.

For another example, according to implementation B, the recommendation engine 225 on the server 270 may determine at least one of the golf clubs 228, the shafts 231, and the balls 233 from the database 226 based on a match between the skill value 237 and the golf club skill value 227. However, the recommendation engine 225 may utilize any of the skill value 237, the swing parameters 233, or the sensor data 256*b* to determine the recommended golf clubs 228, shafts 231, and balls 233, in addition to the models 229 and properties 230 of the golf clubs 228, as well as the properties 232 of the shafts 231. Once the server 270 has determined the recommended golf clubs 228, shafts 231, and balls 233, the recommendation engine 225 on the computing device 210 may further filter the recommendations based on the user data 235 and/or the additional data 235, including location data, for example.

Referring again to flowchart 400, flowchart 400 (at 440) includes transmitting information relating to the recommended sporting apparatus. For example, in regards to implementation A, the computing device 210 may transmit the information relating to the recommended golf club to the display 238 of the computing device 210. The information pertaining to the recommended golf club may include the model and loft, in addition to the shaft model and flex, for example.

For another example, in regards to implementation B, the server 270 may transmit the information pertaining to the recommended golf club over the network 290 to the computing device 210, for rendering on the display 238 of the computing device 210.

The present disclosure describes a system and method for analyzing the swing of a user for determining a recommended sporting apparatus for that user. Modern recommendation engines primarily utilize launch conditions of a ball that are the result of a swing, but do not analyze the swing itself. The launch conditions provided by these modern recommendation engines can only provide limited information about the actual swing of the user, especially because most launch conditions are tested on hard mats at driving ranges or indoor fitting areas, which do not adequately reflect real world impact conditions of the users swing. However, by analyzing the physical swing of the user, utilizing the swing parameters, more information about the skill level of the user is collected in comparison to only testing the launch conditions of the ball because the swing of the user itself remains more consistent throughout varying turf conditions and locations where the swing is recorded. Ultimately, the above described implementations provide a more accurate representation of the skill level of the user, and as a result the system described provides more accurate recommendations of sporting apparatuses.

In describing preferred implementations of the subject matter of the present disclosure, as illustrated in the Figures, specific terminology is employed for the sake of clarity. The claimed subject matter, however, is not intended to be limited to the specific terminology so selected, and it is to be understood that each specific element includes all technical equivalents that operate in a similar manner to accomplish a similar purpose.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. In a system implementing a reference golf club, one or more sensors associated with the reference golf club, and a computing device, a method comprising:
   (a) receiving from the one or more sensors, by the computing device, swing data relating to a swing of the reference golf club;
   (b) analyzing, by the computing device, the swing data to determine recommended shaft parameter values for each of a plurality of shaft parameters using an algorithm;
   (c) accessing, by the computing device, a shaft database comprising actual shaft parameter values corresponding to each of the plurality of shaft parameters for each of a plurality of shafts;
   (d) selecting, by the computing device, at least one shaft from the plurality of shafts based, at least in part, on a comparison between the recommended shaft parameter values and the actual shaft parameter values;
   (e) transmitting, by the computing device, information relating to the at least one shaft; and
   (f) displaying, by the computing device, the information on a display of the computing device.

2. The method of claim 1, wherein the swing data includes a head speed, an acceleration, and an attack angle of the reference golf club.

3. The method of claim 2, wherein the acceleration of the reference golf club includes the maximum tangential acceleration.

4. The method of claim 2, wherein the plurality of shaft parameters comprise shaft weight, shaft frequency, and shaft kick point.

5. The method of claim 4, wherein the recommended shaft parameter values for the shaft weight are determined utilizing the head speed, the recommended shaft parameter values for the shaft frequency are determined utilizing the acceleration, and the recommended shaft parameter values for the shaft kick point are determined utilizing the head speed and the attack angle.

6. The method of claim 1, wherein the use of the algorithm in step (b) comprises:
   determining which of a plurality of swing parameters correspond to each of the shaft parameters of the plurality of shaft parameters;
   calculating, based on the determination, the plurality of swing parameters from the swing data; and
   calculating the recommended shaft parameter values for each of the plurality of shaft parameters from the plurality of swing parameters based on empirical data, the algorithm using the empirical data to generate conversions between the swing parameters and the recommended shaft parameter values.

7. The method of claim 1, wherein, prior to step (a), the method further comprises:
   capturing, by the one or more sensors, the swing data during the swing of the reference golf club; and
   transmitting, by the one or more sensors, to the computing device, the swing data.

8. The method of claim 7, wherein the one or more sensors are attached to one of a grip, a shaft, and a club head of the reference golf club during the swing.

9. The method of claim 1, wherein the swing data is generated based on a three dimensional vector projected onto a location on the reference golf club during the swing of the reference golf club.

10. In a system implementing a reference golf club, one or more sensors associated with the reference golf club, a server, and a computing device, a method comprising:
   (a) receiving from the one or more sensors, by the computing device, swing data relating to a swing of the reference golf club;
   (b) analyzing, by the computing device, the swing data to determine recommended shaft parameter values corresponding to each of a plurality of shaft parameters using an algorithm;
   (c) accessing, by the computing device, a shaft database on the server comprising actual shaft parameter values for each of the plurality of shaft parameters for each of a plurality of shafts;
   (d) transmitting, by the computing device, to the server, the recommended shaft parameter values;
   (d) determining, by the server, at least one shaft from the plurality of shafts based, at least in part, on a comparison between the recommended shaft parameter values and the actual shaft parameter values;
   (e) transmitting, by the server, to the computing device, information relating to the at least one shaft; and
   (f) displaying, by the computing device, the information on a display of the computing device.

11. The method of claim 10, wherein the swing data includes a head speed, an acceleration, and an attack angle of the reference golf club.

12. The method of claim 11, wherein the acceleration of the reference golf club includes the maximum tangential acceleration.

13. The method of claim 11, wherein step (f) further comprises:
displaying a recommended golf club in combination with the information relating to the at least one shaft.

14. The method of claim 11, wherein the plurality of shaft parameters comprise shaft weight, shaft frequency, and shaft kick point.

15. The method of claim 14, wherein the recommended shaft parameter values for the shaft weight are determined utilizing the head speed, the recommended shaft parameter values for the shaft frequency are determined utilizing the acceleration, and the recommended shaft parameter values for the shaft kick point are determined utilizing the head speed and the attack angle.

16. The method of claim 10, wherein the use of the algorithm in step (b) comprises:
determining which of a plurality of swing parameters correspond to each of the shaft parameters of the plurality of shaft parameters;
calculating, based on the determination, the plurality of swing parameters from the swing data; and
calculating the recommended shaft parameter values for each of the plurality of shaft parameters from the plurality of swing parameters based on empirical data, the algorithm using the empirical data to generate conversions between the swing parameters and the recommended shaft parameter values.

17. In a system implementing a reference golf club, one or more sensors associated with the reference golf club, and a computing device, a method comprising:
(a) receiving from the one or more sensors, by the computing device, swing data of the reference golf club in response to a swing of the reference golf club;
(b) analyzing, by the computing device, using an algorithm, head speed to determine a recommended shaft weight value, acceleration to determine a recommended shaft frequency value, and a combination of the head speed and attack angle to determine a recommended shaft kick point value;
(c) accessing, by the computing device, a shaft database comprising actual shaft weight values, actual shaft frequency values, and actual shaft kick point values for each of a plurality of shafts;
(d) determining, by the computing device, using the algorithm, at least one shaft from the plurality of shafts based, at least in part, on a comparison between the recommended shaft weight value and the actual shaft weight value, the recommended shaft frequency value and the actual shaft frequency value, and the recommended kick point value and the actual kick point value;
(e) transmitting, by the computing device, information relating to the at least one shaft; and
(f) displaying, by the computing device, the information on a display of the computing device.

18. The method of claim 17, wherein the use of the algorithm in step (b) comprises:
calculating the head speed, the acceleration, and the attack angle from the swing data; and
calculating the recommended shaft weight value, the recommended shaft frequency value, and the recommended shaft kick point value based on empirical data, the algorithm using the empirical data to generate conversions between the head speed and the recommended shaft weight value, the acceleration and the recommended shaft frequency value, and the head speed and the attack angle and the recommended shaft kick point value.

19. The method of claim 17, wherein step (d) further comprises:
plotting, for each of the plurality of shafts, the actual shaft weight value on a first axis, the actual shaft frequency value on a second axis, and the actual shaft kick point value on a third axis;
plotting the recommended shaft weight value on the first axis, the recommended shaft frequency value on the second axis, and the recommended shaft kick point value on the third axis;
calculating, for each of the plurality of shafts, a three-dimensional distance between the recommended shaft weight value and the actual shaft weight value, the recommended shaft frequency value and the actual shaft weight value, and the recommended shaft kick point value and the actual shaft kick point value; and
selecting the at least one shaft from the plurality of shafts that has the shortest three-dimensional distance.

20. A system comprising:
a reference golf club having a club head, a shaft, and a grip;
a sensing device associated with at least one of the club head, the shaft, and the grip, the sensing device comprising:
one or more sensors configured to generate swing data in response to a swing of the reference golf club; and
a transmitter configured to transmit the swing data; and
a computing device comprising:
a non-transitory computer readable medium configured to store instructions; and
a processor configured to execute the instructions to:
(a) receive the swing data from the sensing device, the swing data relating to the swing of the reference golf club;
(b) determine which of a plurality of swing parameters correspond to each of a plurality of shaft parameters;
(c) calculate, based on the determination, the plurality of swing parameters from the swing data;
(d) calculate recommended shaft parameter values for each of the plurality of shaft parameters from the plurality of swing parameters based on empirical data, the empirical data utilized to generate conversions between the swing parameters and the recommended shaft parameter values;
(e) access a shaft database comprising actual shaft parameter values for each of the plurality of shaft parameters for each of a plurality of shafts;
(f) determine at least one shaft from the plurality of shafts based, at least in part, on a comparison between the recommended shaft parameter values and the actual shaft parameter values;
(g) transmit information relating to the at least one shaft; and
(h) display the information.

* * * * *